United States Patent
O'Connell et al.

(10) Patent No.: US 10,969,393 B2
(45) Date of Patent: Apr. 6, 2021

(54) COMPLEXES BETWEEN ANTI-TNF ANTIBODIES, TRIMERIC TNF PROTEINS AND ORGANIC MOLECULES BINDING THEM

(71) Applicant: UCB Biopharma SRL, Brussels (BE)

(72) Inventors: James Philip O'Connell, Slough (GB); John Robert Porter, Slough (GB); Alastair Lawson, Slough (GB); Daniel John Lightwood, Slough (GB); Rebecca Jayne Munro, Slough (GB)

(73) Assignee: UCB Biopharma SRL, Brussels (BE)

( * ) Notice: Subject to any disclaimer, the term of this patent is extended or adjusted under 35 U.S.C. 154(b) by 0 days.

(21) Appl. No.: 15/736,535

(22) PCT Filed: Oct. 22, 2015

(86) PCT No.: PCT/EP2015/074527
§ 371 (c)(1),
(2) Date: Dec. 14, 2017

(87) PCT Pub. No.: WO2016/202414
PCT Pub. Date: Dec. 22, 2016

(65) Prior Publication Data
US 2018/0171008 A1    Jun. 21, 2018

(30) Foreign Application Priority Data
Jun. 18, 2015 (GB) .................................... 1510758

(51) Int. Cl.
| | |
|---|---|
| *C07D 401/14* | (2006.01) |
| *C07K 14/525* | (2006.01) |
| *C07D 471/00* | (2006.01) |
| *C07K 14/705* | (2006.01) |
| *C07K 16/24* | (2006.01) |
| *C07D 213/72* | (2006.01) |
| *C07D 235/04* | (2006.01) |
| *C07D 239/26* | (2006.01) |
| *C07D 471/04* | (2006.01) |
| *A61K 47/64* | (2017.01) |
| *A61P 37/00* | (2006.01) |
| *A61P 35/00* | (2006.01) |
| *G01N 33/68* | (2006.01) |

(52) U.S. Cl.
CPC ..... *G01N 33/6845* (2013.01); *A61K 47/6425* (2017.08); *A61P 35/00* (2018.01); *A61P 37/00* (2018.01); *C07D 213/72* (2013.01); *C07D 235/04* (2013.01); *C07D 239/26* (2013.01); *C07D 401/14* (2013.01); *C07D 471/00* (2013.01); *C07D 471/04* (2013.01); *C07K 14/525* (2013.01); *C07K 14/70575* (2013.01); *C07K 16/241* (2013.01); *G01N 33/6854* (2013.01); *G01N 33/6863* (2013.01); *C07K 2317/55* (2013.01); *C07K 2317/92* (2013.01); *G01N 2333/525* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 4,908,372 | A | 3/1990 | Carr et al. |
| 5,597,899 | A | 1/1997 | Banner et al. |
| 7,691,815 | B2 | 4/2010 | Liang |
| 7,993,636 | B2 | 8/2011 | Mayumi et al. |
| 8,377,441 | B2 | 2/2013 | Chang |
| 9,908,944 | B2 | 3/2018 | Padkjaer et al. |
| 10,428,148 | B2 | 10/2019 | Katagiri et al. |
| 10,705,094 | B2 | 7/2020 | O'Connell et al. |
| 10,775,385 | B2 | 9/2020 | O'Connell et al. |
| 10,883,996 | B2 | 1/2021 | O'Connell et al. |
| 2001/0018507 | A1 | 8/2001 | Rathjen et al. |
| 2002/0110868 | A1 | 8/2002 | Dahiyat et al. |
| 2003/0060461 | A1 | 3/2003 | Kodama et al. |
| 2004/0067982 | A1 | 4/2004 | Zheng et al. |
| 2006/0222624 | A1 | 10/2006 | Bratt et al. |
| 2007/0117755 | A1 | 5/2007 | Liang |
| 2009/0022659 | A1 | 1/2009 | Olson et al. |
| 2009/0269357 | A1 | 10/2009 | Ke et al. |
| 2010/0266613 | A1 | 10/2010 | Harding et al. |
| 2010/0297111 | A1 | 11/2010 | Beirnaert |
| 2011/0250130 | A1 | 10/2011 | Benatuil et al. |
| 2013/0018105 | A1 | 1/2013 | Carroll et al. |
| 2014/0112929 | A1 | 4/2014 | Batuwangala et al. |
| 2014/0165223 | A1 | 6/2014 | Ntouni et al. |

FOREIGN PATENT DOCUMENTS

| | | |
|---|---|---|
| CA | 2005053 A1 | 6/1990 |
| CN | 1204320 A | 1/1999 |
| CN | 1099802 C | 1/2003 |
| CN | 1700930 A | 11/2005 |
| EP | 0288088 A2 | 10/1988 |
| EP | 0492448 A1 | 3/2000 |

(Continued)

OTHER PUBLICATIONS

Alzani et al., Biochemistry 34:6344-6350 (1995).
Andersen et al., Protein Science 15:2558-2567 (2006).
Baldwin et al., PNAS 93:1021-1026 (1996).
Eck et al., Journal of Biological Chemistry 264:17595-17605 (1989).
Ganesan et al., Pharmazie 67:374-379 (2012).

(Continued)

*Primary Examiner* — Elly-Gerald Stoica
(74) *Attorney, Agent, or Firm* — Medler Ferro Woodhouse & Mills PLLC

(57) ABSTRACT

It has been demonstrated that certain compounds bind to TNF and stabilise a conformation of trimeric TNF that binds to the TNF receptor. Antibodies which selectively bind to complexes of such compounds with TNF superfamily members are disclosed. These antibodies may be used to detect further compounds with the same activity, and as target engagement biomarker.

Figure 1:
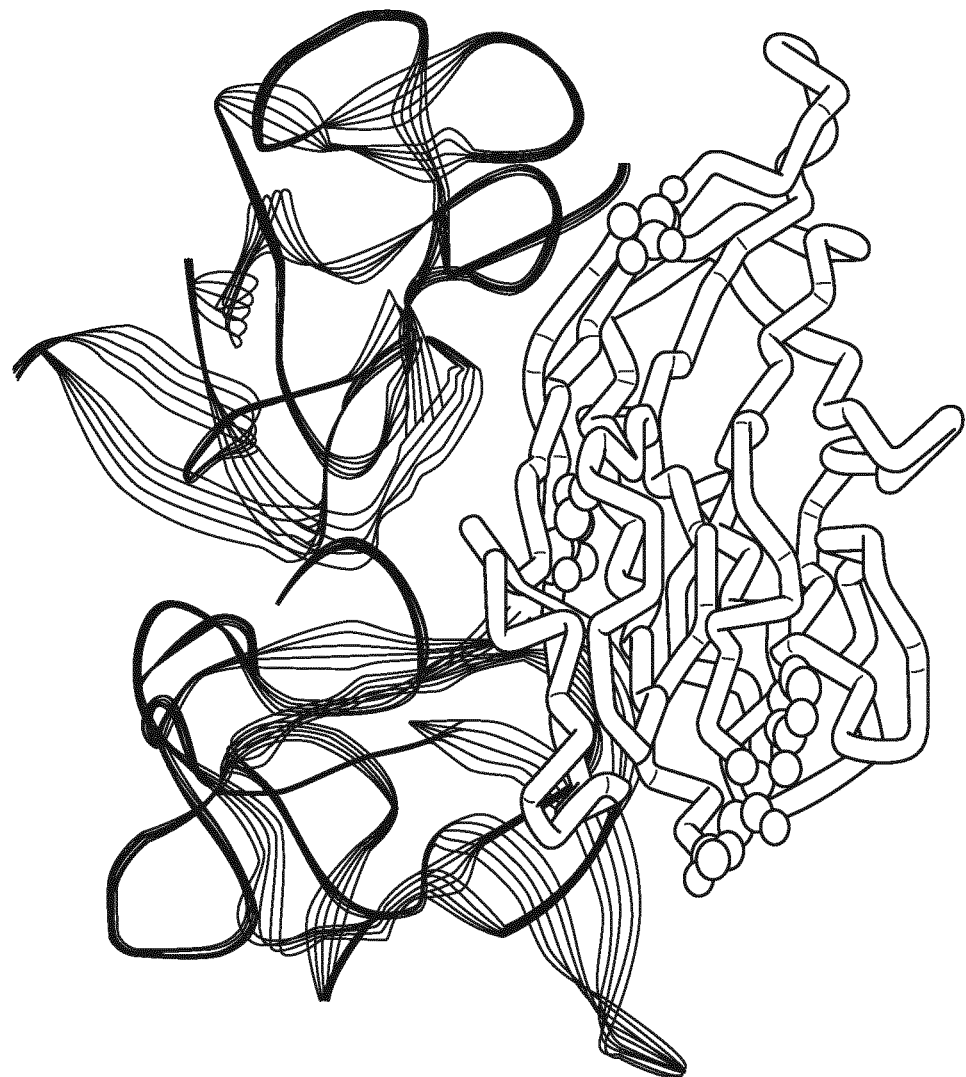

11 Claims, 11 Drawing Sheets
Specification includes a Sequence Listing.

(56) References Cited

FOREIGN PATENT DOCUMENTS

| | | |
|---|---|---|
| JP | H0596 A | 1/1993 |
| JP | 2003-040888 A | 2/2003 |
| JP | 2008-539772 A | 11/2008 |
| JP | 2010-172307 A | 8/2010 |
| JP | 2011-519836 A | 7/2011 |
| JP | 2012-509312 A | 4/2012 |
| WO | WO 93/06489 A1 | 4/1993 |
| WO | WO 93/14083 A1 | 7/1993 |
| WO | 1994/18325 A1 | 8/1994 |
| WO | 97/22587 A | 6/1997 |
| WO | WO 02/098869 A2 | 12/2002 |
| WO | 2004012673 A | 2/2004 |
| WO | 2006/122786 A2 | 11/2006 |
| WO | 2007/060411 A1 | 5/2007 |
| WO | 2009020848 A2 | 8/2008 |
| WO | 2008/144757 A1 | 11/2008 |
| WO | WO 2008/144753 A2 | 11/2008 |
| WO | 2009/132037 A1 | 10/2009 |
| WO | WO 2009/155723 A2 | 12/2009 |
| WO | 2010/058419 A1 | 5/2010 |
| WO | WO 2010/118404 A2 | 10/2010 |
| WO | WO 2012/078878 A2 | 6/2012 |
| WO | WO 2013/024040 A2 | 2/2013 |
| WO | WO 2013/186229 A1 | 12/2013 |
| WO | WO 2014/001557 A1 | 1/2014 |
| WO | WO 2014/009295 A1 | 1/2014 |
| WO | WO 2014/009296 A1 | 1/2014 |
| WO | WO 2014/040076 A1 | 3/2014 |
| WO | WO 2014/123696 A1 | 8/2014 |
| WO | WO 2014/165223 A1 | 10/2014 |
| WO | WO 2015/086496 A1 | 6/2015 |
| WO | WO 2015/086498 A1 | 6/2015 |
| WO | WO 2015/086499 A1 | 6/2015 |
| WO | WO 2015/086500 A1 | 6/2015 |
| WO | WO 2015/086501 A1 | 6/2015 |
| WO | WO 2015/086502 A1 | 6/2015 |
| WO | WO 2015/086503 A1 | 6/2015 |
| WO | WO 2015/086504 A1 | 6/2015 |
| WO | WO 2015/086505 A1 | 6/2015 |
| WO | WO 2015/086506 A1 | 6/2015 |
| WO | WO 2015/086507 A1 | 6/2015 |
| WO | WO 2015/086508 A1 | 6/2015 |
| WO | WO 2015/086509 A1 | 6/2015 |
| WO | WO 2015/086511 A1 | 6/2015 |
| WO | WO 2015/086512 A1 | 6/2015 |
| WO | WO 2015/086513 A1 | 6/2015 |
| WO | WO 2015/086519 A1 | 6/2015 |
| WO | WO 2015/086520 A1 | 6/2015 |
| WO | WO 2015/086521 A1 | 6/2015 |
| WO | WO 2015/086523 A1 | 6/2015 |
| WO | WO 2015/086525 A1 | 6/2015 |
| WO | WO 2015/086526 A1 | 6/2015 |
| WO | WO 2015/086527 A1 | 6/2015 |
| WO | WO 2016/050975 A1 | 4/2016 |
| WO | WO 2016/149436 A1 | 9/2016 |
| WO | WO 2016/149437 A1 | 9/2016 |
| WO | WO 2016/149439 A1 | 9/2016 |
| WO | WO 2016/168633 A1 | 10/2016 |
| WO | WO 2016/168638 A1 | 10/2016 |
| WO | WO 2016/168641 A1 | 10/2016 |
| WO | WO 2016/198398 A1 | 12/2016 |
| WO | WO 2016/198400 A1 | 12/2016 |
| WO | WO 2016/198401 A1 | 12/2016 |
| WO | WO 2016/202411 A1 | 12/2016 |
| WO | WO 2016/202412 A1 | 12/2016 |
| WO | WO 2016/202413 A1 | 12/2016 |
| WO | WO 2016/202415 A1 | 12/2016 |
| WO | WO 2017/023902 A1 | 2/2017 |
| WO | WO 2017/023905 A1 | 2/2017 |
| WO | WO 2017/167993 A1 | 10/2017 |
| WO | WO 2017/167994 A1 | 10/2017 |
| WO | WO 2017/167995 A1 | 10/2017 |
| WO | WO 2017/167996 A1 | 10/2017 |

OTHER PUBLICATIONS

Garcia et al. in: D. Wallach et al. (eds), Advances in TNF Family Research, Advances in Experimental Medicine and Biology 691:187-201 (2011), DOI 10.1007/978-1-4419-6612-4_20.
Grell et al., Cell 83:793-802 (1995).
He et al., Science 310:1022-1025 (2005).
Hoffmann et al., PLOS One 7:e31298 (2012).
Hu et al., Journal of Biological Chemistry 288:27059-27067 (2013).
Jones et al., Journal of Cell Science S13:11-18 (1990).
Kim et al., Journal of Molecular Biology 374:1374-1388 (2007).
Liang et al., Journal of Biological Chemistry 288:13799-13807 (2013).
Loetscher et al., Journal of Biological Chemistry 266:18324-18329 (1991).
Ma et al., Journal of Biological Chemistry 289:12457-12466 (2014).
Mascarenhas et al., BMC Structural Biology 12:8 (2012).
Nesbitt et al., Inflammatory Bowel Diseases 13:1323-1332 (2007).
Silvian et al., ACS Chemical Biology 6:636-647 (2011).
Simon et al., Nature Chemical Biology 9:200-205 (2013).
Sudhamsu et al., PNAS 110:19896-19901 (2013).
Tracey et al., Pharmacology & Therapeutics 117:244-279 (2007).
Zalevsky et al., Journal of Immunology 179:1872-1883 (2007).
Zhu et al., Immunology Letters 102:177-183 (2006).
Cha et al., "High Resolution Crystal Structure of a Human Tumor Necrosis Factor-α Mutant with Low Systemic Toxicity," The Journal of Biological Chemistry 273(4):2153-2160 (1998).
Mukai et al., "Solution of the Structure of the TNF-TNFR2 Complex," Biochemistry 3(148):1-11 (2010).
China National Intellectual Property Administration Search Report, dated Aug. 20, 2019.
Fang et al., "TNF: a structure and function relationship," Foreign Medical Immunology, vol. 26, No. 2. (2003). [Machine translation of Biographic information].
Non-Final Office Action issued in U.S. Appl. No. 15/736,520, dated Feb. 28, 2019.
Non-Final Office Action issued in U.S. Appl. No. 15/736,336, dated Apr. 24, 2019.
Non-Final Office Action issued in U.S. Appl. No. 15/736,558 dated Apr. 26, 2019.
Lloyd et al., "Modelling the human immune response: performance of a 10" human antibody repertoire against a broad panel of therapeutically relevant antigens," Protein Engineering, Design & Selection 22(3):159-168 (2009).
Sedger et al., "TNF and TNF-receptors: From Mediators of Cell Death and Inflammation to Therapeutic Giants—Past, Present, and Future," Cytokine & Growth Factor Reviews, 25:453-473 (2014).
Shibata et al., "Creation and X-ray Structure Analysis of the Tumor Necrosis Factor Receptor-1-selective Mutant of a Tumor Necrosis Factor-α Antagonist," J. Biol. Chem 283(2): 998-1007 (2008).
Office Action issued in U.S. Appl. No. 15/736,336 dated Oct. 3, 2019.
Office Action issued in U.S. Appl. No. 15/736,520 dated Oct. 7, 2019.
Office Action issued in U.S. Appl. No. 15/736,558 dated Nov. 8, 2019.
Office Action issued in U.S. Appl. No. 15/736,614 dated Aug. 29, 2019.
Notice of Allowance in U.S. Appl. No. 15/736,520 dated Feb. 26, 2020.
Notice of Allowance in U.S. Appl. No. 15/736,614 dated Apr. 6, 2020.
Non-final Office Action in U.S. Appl. No. 15/736,558 dated Apr. 21, 2020.
Notice of Allowance in U.S. Appl. No. 15/736,336 dated Jun. 4, 2020.
Non-final Office Action in U.S. Appl. No. 16/470,999 dated Sep. 10, 2020.
Final Office Action in U.S. Appl. No. 15/736,558 dated Oct. 8, 2020.

Fig. 8

| | |
|---|---|
| File: 13090601T | File: 13090601T |
| Item: 1974 cyno TNF control 1 | Item: 1974 cyno TNF control 2 |
| Ligand: CA185_1974 | Ligand: CA185_1974 |
| Curve: Fe=2-1 | Curve: Fe=2-1 |
| Sample: cyno | Sample: cyno |
| Temperature 25 °C | Temperature 25 °C |

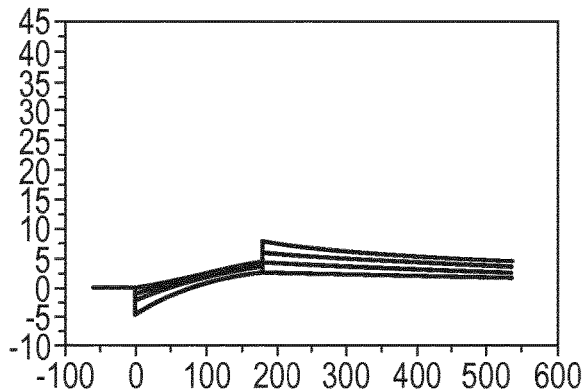 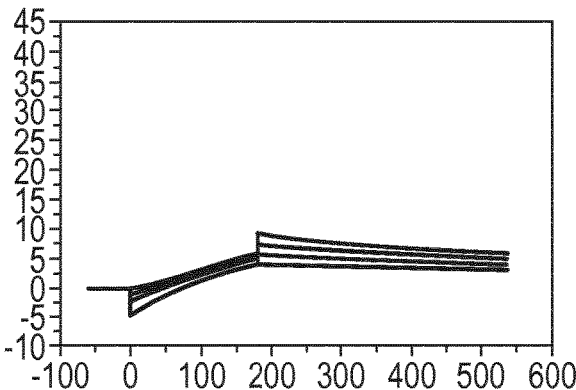

| | |
|---|---|
| Fit: 1:1: Binding | Fit: 1:1: Binding |
| Ka(1/Ms): 1.025E+5 | Ka(1/Ms): 1.253E+5 |
| Kd (1/s): 0.001872 | Kd (1/s): 0.001923 |

| | |
|---|---|
| File: 13090601T | File: 13090601T |
| Item: 1974 cyno TNF+2080 1 | Item: 1974 cyno TNF+2080 2 |
| Ligand: CA185_1974 | Ligand: CA185_1974 |
| Curve: Fe=2-1 | Curve: Fe=2-1 |
| Sample: cyno+NCE | Sample: cyno+NCE |
| Temperature 25 °C | Temperature 25 °C |

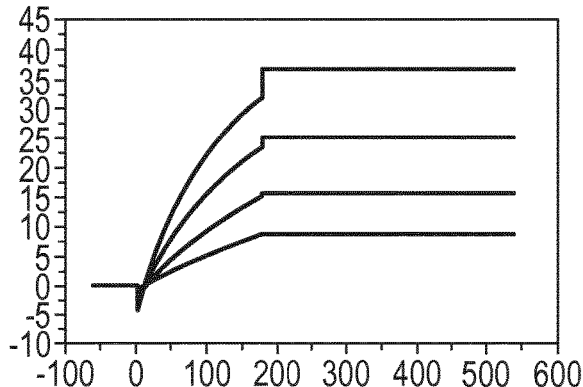 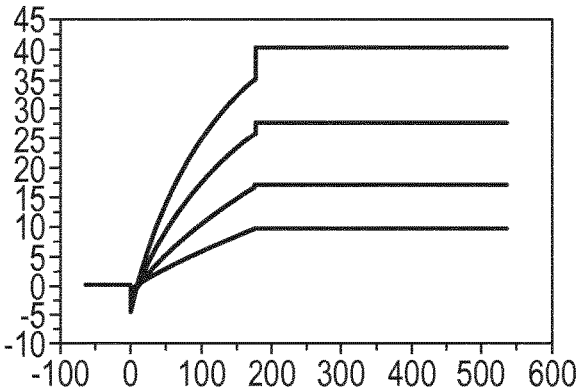

| | |
|---|---|
| Fit: 1:1: Binding | Fit: 1:1: Binding |
| Ka(1/Ms): 1.842E+5 | Ka(1/Ms): 2.008E+5 |
| Kd (1/s): 1.457E-5 | Kd (1/s): 2.053E-5 |

Fig. 9

| | | | |
|---|---|---|---|
| File: | 13090601T | File: | 13090601T |
| Item: | 1974 human TNF control 1 | Item: | 1974 human TNF control 2 |
| Ligand: | CA185_1974 | Ligand: | CA185_1974 |
| Curve: | Fe=4-3 | Curve: | Fe=4-3 |
| Sample: | human | Sample: | human |
| Temperature | 25 °C | Temperature | 25 °C |

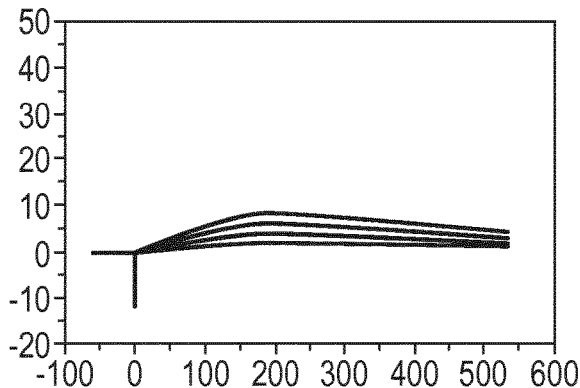 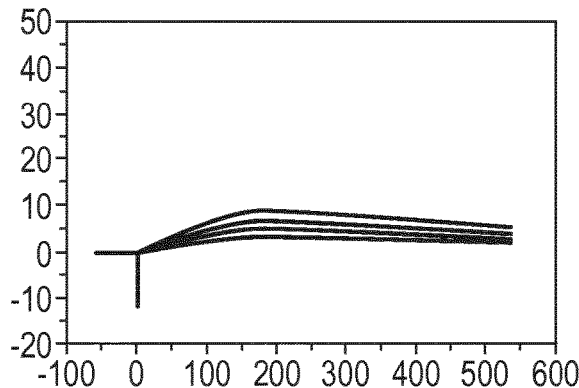

| | | | |
|---|---|---|---|
| Fit: | 1:1: Binding | Fit: | 1:1: Binding |
| Ka(1/Ms): | 8.023E+4 | Ka(1/Ms): | 1.051E+5 |
| Kd (1/s): | 0.001773 | Kd (1/s): | 0.001671 |

| | | | |
|---|---|---|---|
| File: | 13090601T | File: | 13090601T |
| Item: | 1974 human TNF+2080 1 | Item: | 1974 human TNF+2080 2 |
| Ligand: | CA185_1974 | Ligand: | CA185_1974 |
| Curve: | Fe=4-3 | Curve: | Fe=4-3 |
| Sample: | human+NCE | Sample: | human+NCE |
| Temperature | 25 °C | Temperature | 25 °C |

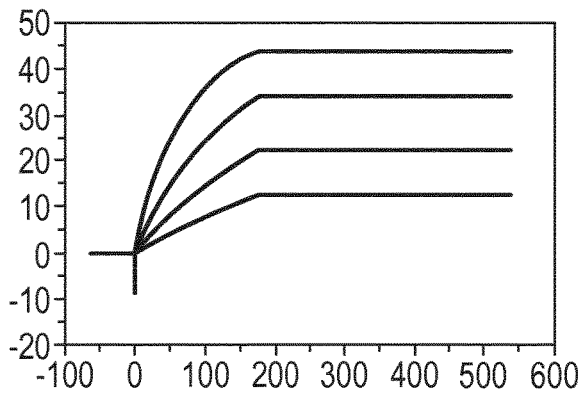 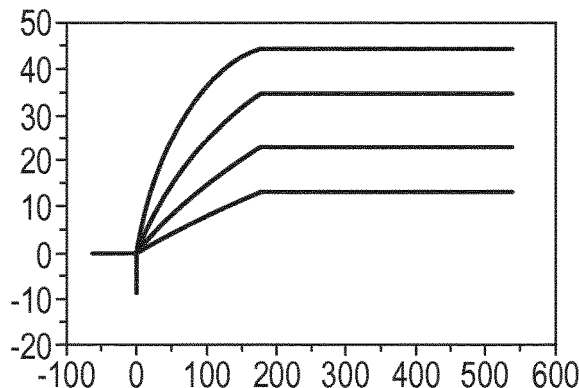

| | | | |
|---|---|---|---|
| Fit: | 1:1: Binding | Fit: | 1:1: Binding |
| Ka(1/Ms): | 3.053E+5 | Ka(1/Ms): | 3.069E+5 |
| Kd (1/s): | 1.477E-7 | Kd (1/s): | 2.726E-5 |

Fig. 10

| Compound | Structure |
|---|---|
| 1 | |
| 2 | |
| 3 | |
| 4 | |

Fig. 10 (Cont.)

| Compound | Structure |
|---|---|
| 5 | |
| 6 | |

```
                        SEQUENCE LISTING

<160> NUMBER OF SEQ ID NOS: 36

<210> SEQ ID NO 1
    <211> LENGTH: 8
    <212> TYPE: PRT
    <213> ORGANISM: Artificial Sequence
    <220> FEATURE:
    <223> OTHER INFORMATION: LCDR1 of 1974/1979

<400> SEQUENCE: 1

Gln Ala Ser Gln Asp Ile Gly Asn
    1               5

<210> SEQ ID NO 2
    <211> LENGTH: 7
    <212> TYPE: PRT
    <213> ORGANISM: Artificial Sequence
    <220> FEATURE:
    <223> OTHER INFORMATION: LCDR2 of 1974

<400> SEQUENCE: 2

Gly Ala Thr Ser Leu Ala Asp
    1               5

<210> SEQ ID NO 3
    <211> LENGTH: 9
    <212> TYPE: PRT
    <213> ORGANISM: Artificial Sequence
    <220> FEATURE:
    <223> OTHER INFORMATION: LCDR3 of 1974

<400> SEQUENCE: 3

Leu Gln Gly Gln Ser Thr Pro Tyr Thr
    1               5

<210> SEQ ID NO 4
    <211> LENGTH: 5
    <212> TYPE: PRT
    <213> ORGANISM: Artificial Sequence
    <220> FEATURE:
    <223> OTHER INFORMATION: HCDR1 of 1974

<400> SEQUENCE: 4

Ala Tyr Tyr Met Ala
    1               5
```

-continued

```
<210> SEQ ID NO 5
<211> LENGTH: 18
<212> TYPE: PRT
<213> ORGANISM: Artificial Sequence
<220> FEATURE:
<223> OTHER INFORMATION: HCDR2 of 1974

<400> SEQUENCE: 5

Ala Ser Ile Asn Tyr Asp Gly Ala Asn Thr Phe Tyr Arg Asp Ser Val
1               5                   10                  15

Lys Gly

<210> SEQ ID NO 6
<211> LENGTH: 12
<212> TYPE: PRT
<213> ORGANISM: Artificial Sequence
<220> FEATURE:
<223> OTHER INFORMATION: HCDR3 of 1974

<400> SEQUENCE: 6

Glu Ala Tyr Gly Tyr Asn Ser Asn Trp Phe Gly Tyr
1               5                   10

<210> SEQ ID NO 7
<211> LENGTH: 107
<212> TYPE: PRT
<213> ORGANISM: Artificial Sequence
<220> FEATURE:
<223> OTHER INFORMATION: LCVR of 1974

<400> SEQUENCE: 7

Asp Ile Gln Met Thr Gln Ser Pro Ala Ser Leu Pro Ala Ser Pro Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Ala
    50                  55                  60

Ser Arg Ser Gly Thr Gln Tyr Ser Leu Lys Ile Ser Arg Leu Gln Val
65                  70                  75                  80

Glu Asp Phe Gly Ile Phe Tyr Cys Leu Gln Gly Gln Ser Thr Pro Tyr
                85                  90                  95

Thr Phe Gly Ala Gly Thr Lys Leu Glu Leu Lys
            100                 105

<210> SEQ ID NO 8
<211> LENGTH: 121
<212> TYPE: PRT
<213> ORGANISM: Artificial Sequence
<220> FEATURE:
<223> OTHER INFORMATION: HCVR of 1974

<400> SEQUENCE: 8

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
            20                  25                  30

Tyr Met Ala Trp Val Arg Gln Ala Pro Thr Lys Gly Leu Glu Trp Val
        35                  40                  45

Ala Ser Ile Asn Tyr Asp Gly Ala Asn Thr Phe Tyr Arg Asp Ser Val
    50                  55                  60
```

Lys Gly Arg Phe Thr Val Ser Arg Asp Asn Ala Arg Ser Ser Leu Tyr
 65                  70                  75                  80

Leu Gln Met Asp Ser Leu Arg Ser Glu Asp Thr Ala Thr Tyr Tyr Cys
                 85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ser
        115                 120

<210> SEQ ID NO 9
<211> LENGTH: 321
<212> TYPE: DNA
<213> ORGANISM: Artificial Sequence
<220> FEATURE:
<223> OTHER INFORMATION: LCVR DNA of 1974

<400> SEQUENCE: 9
gacatccaga tgacccagtc tcctgcctcc ctgcctgcat ccccggaaga aattgtcacc        60
atcacatgcc aggcaagcca ggacattggt aattggttat catggtatca gcagaaacca      120
gggaaatcgc ctcagctcct gatctatggt gcaaccagct tggcagatgg ggtcccatca      180
aggttcagcg ccagtagatc tggcacacag tactctctta agatcagcag actgcaggtt      240
gaagattttg gaatctttta ctgtctacag ggtcaaagta ctccgtacac gtttggagct      300
gggaccaagc tggaactgaa a                                                321

<210> SEQ ID NO 10
<211> LENGTH: 363
<212> TYPE: DNA
<213> ORGANISM: Artificial Sequence
<220> FEATURE:
<223> OTHER INFORMATION: HCVR DNA of 1974

<400> SEQUENCE: 10
gacgtgcagc tggtggaatc tggaggaggc ttagtgcagc ctggaaggtc cctgaaactc        60
tcctgtgcag cctcaggatt cactttcagt gcctattaca tggcctgggt ccgccaggct      120
ccaacgaagg gtctggagtg gtcgcatcc attaattatg atggtgctaa cactttctat       180
cgcgactccg tgaagggccg attcactgtc tccagagata tgcaagaag cagcctatac       240 ctacaaatgg acagtctgag gtctgaggac acggccactt attactgtac aacagaggct      300
tacggatata actcaaattg gtttggttac tggggccaag gcactctggt cactgtctcg      360
agc                                                                    363

<210> SEQ ID NO 11
<211> LENGTH: 214
<212> TYPE: PRT
<213> ORGANISM: Artificial Sequence
<220> FEATURE:
<223> OTHER INFORMATION: 1974 LC kappa full

<400> SEQUENCE: 11

Asp Ile Gln Met Thr Gln Ser Pro Ala Ser Leu Pro Ala Ser Pro Glu
  1               5                  10                  15

Glu Ile Val Thr Ile Thr Cys Gln Ala Ser Gln Asp Ile Gly Asn Trp
                 20                  25                  30

Leu Ser Trp Tyr Gln Gln Lys Pro Gly Lys Ser Pro Gln Leu Leu Ile
             35                  40                  45

Tyr Gly Ala Thr Ser Leu Ala Asp Gly Val Pro Ser Arg Phe Ser Ala
 50                  55                  60

```
Ser Arg Ser Gly Thr Gln Tyr Ser Leu Lys Ile Ser Arg Leu Gln Val
 65                  70                  75                  80

Glu Asp Phe Gly Ile Phe Tyr Cys Leu Gln Gly Gln Ser Thr Pro Tyr
                 85                  90                  95

Thr Phe Gly Ala Gly Thr Lys Leu Glu Leu Lys Arg Thr Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 12
<211> LENGTH: 445
<212> TYPE: PRT
<213> ORGANISM: Artificial Sequence
<220> FEATURE:
<223> OTHER INFORMATION: 1974 HC mIgG1 full

<400> SEQUENCE: 12

Asp Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Phe Ser Ala Tyr
             20                  25                  30

Tyr Met Ala Trp Val Arg Gln Ala Pro Thr Lys Gly Leu Glu Trp Val
         35                  40                  45

Ala Ser Ile Asn Tyr Asp Gly Ala Asn Thr Phe Tyr Arg Asp Ser Val
     50                  55                  60

Lys Gly Arg Phe Thr Val Ser Arg Asp Asn Ala Arg Ser Ser Leu Tyr
 65                  70                  75                  80

Leu Gln Met Asp Ser Leu Arg Ser Glu Asp Thr Ala Thr Tyr Tyr Cys
                 85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ala Lys Thr Thr Pro Pro Ser
        115                 120                 125

Val Tyr Pro Leu Ala Pro Gly Ser Ala Ala Gln Thr Asn Ser Met Val
130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205
```

```
Ala Ser Ser Thr Lys Val Asp Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
                260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
        290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 13
<211> LENGTH: 223
<212> TYPE: PRT
<213> ORGANISM: Artificial Sequence
<220> FEATURE:
<223> OTHER INFORMATION: 1974 HC mFabno hinge full

<400> SEQUENCE: 13

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
            20                  25                  30

Tyr Met Ala Trp Val Arg Gln Ala Pro Thr Lys Gly Leu Glu Trp Val
        35                  40                  45

Ala Ser Ile Asn Tyr Asp Gly Ala Asn Thr Phe Tyr Arg Asp Ser Val
    50                  55                  60

Lys Gly Arg Phe Thr Val Ser Arg Asp Asn Ala Arg Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ser Ala Lys Thr Thr Pro Pro Ser
        115                 120                 125
```

| | | | | | | | | | | | | | | |
|---|---|---|---|---|---|---|---|---|---|---|---|---|---|---|
|Val|Tyr|Pro|Leu|Ala|Pro|Gly|Ser|Ala|Ala|Gln|Thr|Asn|Ser|Met|Val|
| |130| | | |135| | | |140| | | | | |

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Ser Val Thr Val Pro
                180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys
    210                 215                 220

<210> SEQ ID NO 14
<211> LENGTH: 642
<212> TYPE: DNA
<213> ORGANISM: Artificial Sequence
<220> FEATURE:
<223> OTHER INFORMATION: 1974 LC DNA kappa full

<400> SEQUENCE: 14

```
gacatccaga tgacccagtc tcctgcctcc ctgcctgcat ccccggaaga aattgtcacc    60
atcacatgcc aggcaagcca ggacattggt aattggttat catggtatca gcagaaacca   120
gggaaatcgc ctcagctcct gatctatggt gcaaccagct ggcagatggg gtcccatca   180
aggttcagcg ccagtagatc tggcacacag tactctctta agatcagcag actgcaggtt   240
gaagattttg gaatctttta ctgtctacag ggtcaaagta ctccgtacac gtttggagct   300
gggaccaagc tggaactgaa acgtacggat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag cccctcacg   540
ttgaccaagg acgagtatga cgacataaac agctatacct gtgaggccac tcacaagaca   600
tcaacttcac ccattgtcaa gagcttcaac aggaatgagt gt                      642
```

<210> SEQ ID NO 15
<211> LENGTH: 1335
<212> TYPE: DNA
<213> ORGANISM: Artificial Sequence
<220> FEATURE:
<223> OTHER INFORMATION: 1974 HC DNA mIgG1 full

<400> SEQUENCE: 15

```
gacgtgcagc tggtggaatc tggaggaggc ttagtgcagc ctggaaggtc cctgaaactc    60
tcctgtgcag cctcaggatt cactttcagt gcctattaca tggcctgggt ccgccaggct   120
ccaacgaagg gtctggagtg ggtcgcatcc attaattatg atggtgctaa cacttttctat   180
cgcgactccg tgaagggccg attcactgtc tccagagata atgcaagaag cagcctatac   240
ctacaaatgg acagtctgag gtctgaggac acggccactt attactgtac aacagaggct   300
tacggatata actcaaattg gtttggttac tggggccaag gcactctggt cactgtctcg   360
agtgccaaaa cgacaccccc atctgtctat ccactggccc ctggatctgc tgcccaaact   420
aactccatgg tgaccctggg atgcctggtc aagggctatt ccctgagcc agtgacagtg   480
acctggaact ctgcatccct gtccagcggt gtgcacacct tcccagctgt cctgcagtct   540
gacctctaca ctctgagcag ctcagtgact gtcccctcca gcacctggcc cagcgagacc   600
```

```
gtcacctgca acgttgccca cccggccagc agcaccaagg tggacaagaa aattgtgccc      660
agggattgtg gttgtaagcc ttgcatatgt acagtcccag aagtatcatc tgtcttcatc      720
ttccccccaa agcccaagga tgtgctcacc attactctga ctcctaaggt cacgtgtgtt      780
gtggtagaca tcagcaagga tgatcccgag gtccagttca gctggtttgt agatgatgtg      840
gaggtgcaca cagctcagac gcaacccgg gaggagcagt tcaacagcac tttccgctca       900
gtcagtgaac ttcccatcat gcaccaggac tggctcaatg gcaaggagtt caaatgcagg      960
gtcaacagtg cagctttccc tgcccccatc gagaaaacca tctccaaaac caaaggcaga     1020
ccgaaggctc cacaggtgta caccattcca cctcccaagg agcagatggc aaggataaaa     1080
gtcagtctga cctgcatgat aacagacttc ttccctgaag acattactgt ggagtggcag     1140
tggaatgggc agccagcgga gaactacaag aacactcagc ccatcatgga cacagatggc     1200
tcttacttcg tctacagcaa gctcaatgtg cagagagca actgggaggc aggaaatact      1260
ttcacctgct ctgtgttaca tgagggcctg cacaaccacc atactgagaa gagcctctcc     1320
cactctcctg gtaaa                                                       1335

<210> SEQ ID NO 16
<211> LENGTH: 669
<212> TYPE: DNA
<213> ORGANISM: Artificial Sequence
<220> FEATURE:
<223> OTHER INFORMATION: 1974 HC DNA mFabno hinge full

<400> SEQUENCE: 16
gacgtgcagc tggtggaatc tggaggaggc ttagtgcagc ctggaaggtc cctgaaactc       60
tcctgtgcag cctcaggatt cactttcagt gcctattaca tggcctgggt ccgccaggct      120
ccaacgaagg gtctggagtg ggtcgcatcc attaattatg atggtgctaa cacttttctat     180 cgcgactccg tgaagggccg attcactgtc tccagagata tgcaagaag cagcctatac      240 ctacaaatgg acagtctgag gtctgaggac acggccactt attactgtac aacagaggct      300
tacggatata actcaaattg gtttggttac tggggccaag gcactctggt cactgtctcg      360
agtgccaaaa cgacaccccc atctgtctat ccactggccc ctggatctgc tgcccaaact      420
aactccatgg tgaccctggg atgcctggtc aagggctatt tccctgagcc agtgacagtg      480
acctggaact ctggatccct gtccagcggt gtgcacacct tcccggctgt cctgcaatct     540
gacctctaca ctctgagcag ctcagtgact gtcccctcca gcacctggcc cagcgagacc      600
gtcacctgca acgttgccca cccggccagc agcaccaagg tggacaagaa aattgtgccc      660
agggattgt                                                              669

<210> SEQ ID NO 17
<211> LENGTH: 7
<212> TYPE: PRT
<213> ORGANISM: Artificial Sequence
<220> FEATURE:
<223> OTHER INFORMATION: LCDR2 of 1979

<400> SEQUENCE: 17

Gly Thr Thr Ser Leu Ala Asp
1               5

<210> SEQ ID NO 18
<211> LENGTH: 10
<212> TYPE: PRT
<213> ORGANISM: Artificial Sequence
```

```
<220> FEATURE:
<223> OTHER INFORMATION: LCDR3 of 1979

<400> SEQUENCE: 18

Leu Gln Ala Tyr Ser Thr Pro Phe Thr Phe
1               5                   10

<210> SEQ ID NO 19
<211> LENGTH: 5
<212> TYPE: PRT
<213> ORGANISM: Artificial Sequence
<220> FEATURE:
<223> OTHER INFORMATION: HCDR1 of 1979

<400> SEQUENCE: 19

Asn Ser Tyr Trp Asp
1               5

<210> SEQ ID NO 20
<211> LENGTH: 16
<212> TYPE: PRT
<213> ORGANISM: Artificial Sequence
<220> FEATURE:
<223> OTHER INFORMATION: HCDR2 of 1979

<400> SEQUENCE: 20

Tyr Ile Asn Tyr Ser Gly Ser Thr Gly Tyr Asn Pro Ser Leu Lys Ser
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: HCDR3 of 1979

<400> SEQUENCE: 21

Gly Thr Tyr Gly Tyr Asn Ala Tyr His Phe Asp Tyr
1               5                   10

<210> SEQ ID NO 22
<211> LENGTH: 107
<212> TYPE: PRT
<213> ORGANISM: Artificial Sequence
<220> FEATURE:
<223> OTHER INFORMATION:
      DIQMTQSPASLSASLEEIVTITCQASQDIGNWLSWYQQKPGKSPHLLIYGTTSLADGVPSRFSGS
      RSGTQYSLKISGLQVADIGIYVCLQAYSTPFTFGSGTKLEIK

<400> SEQUENCE: 22

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
                20                  25                  30

Leu Ser Trp Tyr Gln Gln Lys Pro Gly Lys Ser Pro His Leu Leu Ile
            35                  40                  45

Tyr Gly Thr Thr Ser Leu Ala Asp Gly Val Pro Ser Arg Phe Ser Gly
        50                  55                  60

Ser Arg Ser Gly Thr Gln Tyr Ser Leu Lys Ile Ser Gly Leu Gln Val
65                  70                  75                  80

Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys
            100                 105
```

<210> SEQ ID NO 23
<211> LENGTH: 120
<212> TYPE: PRT
<213> ORGANISM: Artificial Sequence
<220> FEATURE:
<223> OTHER INFORMATION: HCVR of 1979

<400> SEQUENCE: 23

```
Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
            20                  25                  30

Tyr Trp Asp Trp Ile Arg Lys Phe Pro Gly Asn Lys Met Glu Trp Met
        35                  40                  45

Gly Tyr Ile Asn Tyr Ser Gly Ser Thr Gly Tyr Asn Pro Ser Leu Lys
    50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
            100                 105                 110

Gly Val Met Val Thr Val Ser Ser
        115                 120
```

<210> SEQ ID NO 24
<211> LENGTH: 321
<212> TYPE: DNA
<213> ORGANISM: Artificial Sequence
<220> FEATURE:
<223> OTHER INFORMATION: LCVR DNA of 1979

<400> SEQUENCE: 24

```
gacatccaaa tgacacagtc tcctgcctcc ctgtctgcat ctctggaaga aattgtcacc        60
attacatgcc aggcaagcca ggacattggt aattggttat catggtatca gcagaaacca       120
gggaaatctc ctcacctcct gatctatggt accaccagct ggcagatgg ggtcccatca        180 aggttcagcg gcagtagatc tggtacacag tattctctta agatcagcgg actacaggtt       240
gcagatattg gaatctatgt ctgtctacag gcttatagta ctccattcac gttcggctca       300
gggacaaagc tggaaataaa a                                                 321
```

<210> SEQ ID NO 25
<211> LENGTH: 360
<212> TYPE: DNA
<213> ORGANISM: Artificial Sequence
<220> FEATURE:
<223> OTHER INFORMATION: HCVR DNA of 1979

<400> SEQUENCE: 25

```
gaggtgcacc tggtggagtc tggacctggc cttgtgaaac cctcacagtc actctccctc        60
acctgttctg tcactggtta ctccatcact aatagttact gggactggat ccggaagttc       120
ccaggaaata aaatggagtg gatgggatac ataaactaca gtggtagcac tggctacaac       180
ccatctctca aaagtcgaat ctccattagt agagacacat cgaacaatca gttcttcctg       240
cagctgaact ctataactac tgaggacaca gccacatatt actgtgcacg agggacctat       300
gggtataacg cctaccactt tgattactgg ggccgaggag tcatggtcac agtctcgagc       360
```

```
<210> SEQ ID NO 26
<211> LENGTH: 214
<212> TYPE: PRT
<213> ORGANISM: Artificial Sequence
<220> FEATURE:
<223> OTHER INFORMATION: 1979 LC Kappa full

<400> SEQUENCE: 26

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro His Leu Leu Ile
        35                  40                  45

Tyr Gly Thr Thr Ser Leu Ala Asp Gly Val Pro Ser Arg Phe Ser Gly
    50                  55                  60

Ser Arg Ser Gly Thr Gln Tyr Ser Leu Lys Ile Ser Gly Leu Gln Val
65                  70                  75                  80

Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys Arg Thr Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 27
<211> LENGTH: 444
<212> TYPE: PRT
<213> ORGANISM: Artificial Sequence
<220> FEATURE:
<223> OTHER INFORMATION: 1979 HC mIgG1 full

<400> SEQUENCE: 27

Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
            20                  25                  30

Tyr Trp Asp Trp Ile Arg Lys Phe Pro Gly Asn Lys Met Glu Trp Met
        35                  40                  45

Gly Tyr Ile Asn Tyr Ser Gly Ser Thr Gly Tyr Asn Pro Ser Leu Lys
    50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
                85                  90                  95
```

```
Arg Gly Thr Tyr Gly Tyr Asn Ala Tyr His Phe Asp Tyr Trp Gly Arg
            100                 105                 110

Gly Val Met Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Thr Val Pro Ser
        180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
                260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
                340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
        435                 440

<210> SEQ ID NO 28
<211> LENGTH: 222
<212> TYPE: PRT
<213> ORGANISM: Artificial Sequence
<220> FEATURE:
<223> OTHER INFORMATION: 1979 HC mFabno hinge full
```

<400> SEQUENCE: 28

| | | | | | | | | | | | | | | | |
|---|---|---|---|---|---|---|---|---|---|---|---|---|---|---|---|
| Glu | Val | His | Leu | Val | Glu | Ser | Gly | Pro | Gly | Leu | Val | Lys | Pro | Ser | Gln |
| 1 | | | | 5 | | | | | 10 | | | | | 15 | |

Ser Leu Ser Leu Thr Cys Ser Val Thr Gly Tyr Ser Ile Thr Asn Ser
            20                  25                  30

Tyr Trp Asp Trp Ile Arg Lys Phe Pro Gly Asn Lys Met Glu Trp Met
        35                  40                  45

Gly Tyr Ile Asn Tyr Ser Gly Ser Thr Gly Tyr Asn Pro Ser Leu Lys
    50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
            100                 105                 110

Gly Val Met Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys
    210                 215                 220

<210> SEQ ID NO 29
<211> LENGTH: 642
<212> TYPE: DNA
<213> ORGANISM: Artificial Sequence
<220> FEATURE:
<223> OTHER INFORMATION: 1979 LC DNA Kappa full

<400> SEQUENCE: 29

```
gacatccaaa tgacacagtc tcctgcctcc ctgtctgcat ctctggaaga aattgtcacc      60
attacatgcc aggcaagcca ggacattggt aattggttat catggtatca gcagaaacca     120
gggaaatctc ctcacctcct gatctatggt accaccagct ggcagatggg gtcccatca     180
aggttcagcg gcagtagatc tggtacacag tattctctta agatcagcgg actacaggtt     240
gcagatattg gaatctatgt ctgtctacag gcttatagta ctccattcac gttcggctca     300
gggacaaagc tggaaataaa acgtacggat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag cacccctcacg     540
ttgaccaagg acgagtatga acgacataac agctatacct gtgaggccac tcacaagaca     600
tcaacttcac ccattgtcaa gagcttcaac aggaatgagt gt                        642
```

<210> SEQ ID NO 30
<211> LENGTH: 1332
<212> TYPE: DNA
<213> ORGANISM: Artificial Sequence
<220> FEATURE:
<223> OTHER INFORMATION: 1979 HC DNA mIgG1 full

<400> SEQUENCE: 30

| | | | | | |
|---|---|---|---|---|---|
| gaggtgcacc | tggtggagtc | tggacctggc | cttgtgaaac | cctcacagtc | actctccctc | 60 |
| acctgttctg | tcactggtta | ctccatcact | aatagttact | gggactggat | ccggaagttc | 120 |
| ccaggaaata | aaatggagtg | gatgggatac | ataaactaca | gtggtagcac | tggctacaac | 180 |
| ccatctctca | aaagtcgaat | ctccattagt | agagacacat | cgaacaatca | gttcttcctg | 240 |
| cagctgaact | ctataactac | tgaggacaca | gccacatatt | actgtgcacg | agggacctat | 300 |
| gggtataacg | cctaccactt | tgattactgg | ggccgaggag | tcatggtcac | agtctcgagt | 360 |
| gccaaaacga | cacccccatc | tgtctatcca | ctggcccctg | gatctgctgc | ccaaactaac | 420 |
| tccatggtga | ccctgggatg | cctggtcaag | ggctatttcc | ctgagccagt | gacagtgacc | 480 |
| tggaactctg | gatccctgtc | cagcggtgtg | cacaccttcc | cagctgtcct | gcagtctgac | 540 |
| ctctacactc | tgagcagctc | agtgactgtc | cctccagca | cctggcccag | cgagaccgtc | 600 |
| acctgcaacg | ttgcccaccc | ggccagcagc | accaaggtgg | acaagaaaat | tgtgcccagg | 660 |
| gattgtggtt | gtaagccttg | catatgtaca | gtcccagaag | tatcatctgt | cttcatcttc | 720 |
| cccccaaagc | ccaaggatgt | gctcaccatt | actctgactc | ctaaggtcac | gtgtgttgtg | 780 |
| gtagacatca | gcaaggatga | tcccgaggtc | cagttcagct | ggtttgtaga | tgatgtggag | 840 |
| gtgcacacag | ctcagacgca | accccgggag | gagcagttca | acagcacttt | ccgctcagtc | 900 |
| agtgaacttc | ccatcatgca | ccaggactgg | ctcaatggca | aggagttcaa | atgcagggtc | 960 |
| aacagtgcag | ctttccctgc | ccccatcgag | aaaaccatct | ccaaaaccaa | aggcagaccg | 1020 |
| aaggctccac | aggtgtacac | cattccacct | cccaaggagc | agatggccaa | ggataaagtc | 1080 |
| agtctgacct | gcatgataac | agacttcttc | cctgaagaca | ttactgtgga | gtggcagtgg | 1140 |
| aatgggcagc | cagcggagaa | ctacaagaac | actcagccca | tcatggacac | agatggctct | 1200 |
| tacttcgtct | acagcaagct | caatgtgcag | aagagcaact | gggaggcagg | aaatactttc | 1260 |
| acctgctctg | tgttacatga | gggcctgcac | aaccaccata | ctgagaagag | cctctcccac | 1320 |
| tctcctggta | aa | | | | | 1332 |

<210> SEQ ID NO 31
<211> LENGTH: 666
<212> TYPE: DNA
<213> ORGANISM: Artificial Sequence
<220> FEATURE:
<223> OTHER INFORMATION: 1979 HC DNA mFabno hinge full

<400> SEQUENCE: 31

| | | | | | |
|---|---|---|---|---|---|
| gaggtgcacc | tggtggagtc | tggacctggc | cttgtgaaac | cctcacagtc | actctccctc | 60 |
| acctgttctg | tcactggtta | ctccatcact | aatagttact | gggactggat | ccggaagttc | 120 |
| ccaggaaata | aaatggagtg | gatgggatac | ataaactaca | gtggtagcac | tggctacaac | 180 |
| ccatctctca | aaagtcgaat | ctccattagt | agagacacat | cgaacaatca | gttcttcctg | 240 |
| cagctgaact | ctataactac | tgaggacaca | gccacatatt | actgtgcacg | agggacctat | 300 |
| gggtataacg | cctaccactt | tgattactgg | ggcgaggag | tcatggtcac | agtctcgagt | 360 |
| gccaaaacga | cacccccatc | tgtctatcca | ctggcccctg | gatctgctgc | ccaaactaac | 420 |

```
tccatggtga ccctgggatg cctggtcaag ggctatttcc ctgagccagt gacagtgacc      480
tggaactctg atccctgtc cagcggtgtg cacaccttcc cggctgtcct gcaatctgac       540
ctctacactc tgagcagctc agtgactgtc ccctccagca cctggcccag cgagaccgtc      600
acctgcaacg ttgcccaccc ggccagcagc accaaggtgg acaagaaaat tgtgcccagg      660
gattgt                                                                 666
```

<210> SEQ ID NO 32
<211> LENGTH: 235
<212> TYPE: PRT
<213> ORGANISM: Rattus norvegicus

<400> SEQUENCE: 32

```
Met Ser Thr Glu Ser Met Ile Arg Asp Val Glu Leu Ala Glu Glu Ala
1               5                   10                  15

Leu Pro Lys Lys Met Gly Gly Leu Gln Asn Ser Arg Arg Cys Leu Cys
                20                  25                  30

Leu Ser Leu Phe Ser Phe Leu Leu Val Ala Gly Ala Thr Thr Leu Phe
            35                  40                  45

Cys Leu Leu Asn Phe Gly Val Ile Gly Pro Asn Lys Glu Glu Lys Phe
        50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95

Ala Asn His Gln Ala Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
        115                 120                 125

Val Pro Ala Asp Gly Leu Tyr Leu Ile Tyr Ser Gln Val Leu Phe Lys
130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Ser Leu Leu Ser Ala Ile Lys
                165                 170                 175

Ser Pro Cys Pro Lys Asp Thr Pro Glu Gly Ala Glu Leu Lys Pro Trp
            180                 185                 190

Tyr Glu Pro Met Tyr Leu Gly Gly Val Phe Gln Leu Glu Lys Gly Asp
        195                 200                 205

Leu Leu Ser Ala Glu Val Asn Leu Pro Lys Tyr Leu Asp Ile Thr Glu
    210                 215                 220

Ser Gly Gln Val Tyr Phe Gly Val Ile Ala Leu
225                 230                 235
```

<210> SEQ ID NO 33
<211> LENGTH: 235
<212> TYPE: PRT
<213> ORGANISM: Mus musculus

<400> SEQUENCE: 33

```
Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
                20                  25                  30

Leu Ser Leu Phe Ser Phe Leu Leu Val Ala Gly Ala Thr Thr Leu Phe
            35                  40                  45
```

```
Cys Leu Leu Asn Phe Gly Val Ile Gly Pro Gln Arg Asp Glu Lys Phe
 50                  55                  60

Pro Asn Gly Leu Pro Leu Ile Ser Ser Met Ala Gln Thr Leu Thr Leu
 65                  70                  75                  80

Arg Ser Ser Ser Gln Asn Ser Ser Asp Lys Pro Val Ala His Val Val
                 85                  90                  95

Ala Asn His Gln Val Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
        115                 120                 125

Val Pro Ala Asp Gly Leu Tyr Leu Val Tyr Ser Gln Val Leu Phe Lys
130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205

Gln Leu Ser Ala Glu Val Asn Leu Pro Lys Tyr Leu Asp Phe Ala Glu
210                 215                 220

Ser Gly Gln Val Tyr Phe Gly Val Ile Ala Leu
225                 230                 235

<210> SEQ ID NO 34
<211> LENGTH: 233
<212> TYPE: PRT
<213> ORGANISM: Homo sapiens

<400> SEQUENCE: 34

Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
             20                  25                  30

Leu Ser Leu Phe Ser Phe Leu Ile Val Ala Gly Ala Thr Thr Leu Phe
         35                  40                  45

Cys Leu Leu His Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190
```

```
Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 35
<211> LENGTH: 158
<212> TYPE: PRT
<213> ORGANISM: Homo sapiens

<400> SEQUENCE: 35

Ser Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155

<210> SEQ ID NO 36
<211> LENGTH: 157
<212> TYPE: PRT
<213> ORGANISM: Homo sapiens

<400> SEQUENCE: 36

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125
```

-continued

```
Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

COMPLEXES BETWEEN ANTI-TNF ANTIBODIES, TRIMERIC TNF PROTEINS AND ORGANIC MOLECULES BINDING THEM

REFERENCE TO AN ELECTRONIC SEQUENCE LISTING

The contents of the electronic sequence listing (00890005US1seqlist.txt; Size: 41,937 bytes; and Date of Creation Dec. 13, 2017) is herein incorporated by reference in its entirety.

FIELD OF THE INVENTION

This invention relates to antibodies which may be used to screen for small molecule modulators of the TNF superfamily that form complexes with TNF superfamily members. In particular, the invention relates to antibodies which selectively bind to such complexes, and uses of such antibodies. The present invention also relates to assays for identifying new modulators of the TNF superfamily using said antibodies.

BACKGROUND OF THE INVENTION

The Tumour Necrosis Factor (TNF) superfamily is a family of proteins that share a primary function of regulating cell survival and cell death. Members of the TNF superfamily share a common core motif, which consists of two antiparallel β-pleated sheets with antiparallel β-strands, forming a "jelly roll" β-structure. Another common feature shared by members of the TNF superfamily is the formation of homo- or heterotrimeric complexes. It is these trimeric forms of the TNF superfamily members that bind to, and activate, specific TNF superfamily receptors.

TNFα is the archetypal member of the TNF superfamily. Dysregulation of TNFα production has been implicated in a number of pathological conditions of significant medical importance. For example, TNFα has been implicated in rheumatoid arthritis, inflammatory bowel diseases (including Crohn's disease), psoriasis, Alzheimer's disease (AD), Parkinson's disease (PD), pain, epilepsy, osteoporosis, asthma, systemic lupus erythematosus (SLE) and multiple sclerosis (MS). Other members of the TNF superfamily have also been implicated in pathological conditions, including autoimmune disease.

Conventional antagonists of TNF superfamily members are macromolecular and act by inhibiting the binding of the TNF superfamily member to its receptor. Examples of conventional antagonists include anti-TNFα antibodies, particularly monoclonal antibodies, such as infliximab (Remicade®), adalimumab (Humira®) and certolizumab pegol (Cimzia®), or soluble TNFα receptor fusion proteins, such as etanercept (Enbrel®).

SUMMARY OF THE INVENTION

The present inventors have identified classes of small molecular entities (SME) that modulate TNFα. These compounds act by binding to the homotrimeric form of TNFα, and inducing and/or stabilising a conformational change in the homotrimer of TNFα. For example, homotrimers of TNFα with the compound bound can bind to TNFα receptors, but are less able, or unable, to initiate signalling downstream of the TNFα receptor. These compounds can be used in the treatment of conditions mediated by TNFα.

The present inventors have developed antibodies that bind selectively to complexes comprising such compounds and a TNF superfamily member. These antibodies may be used to identify further compounds that are capable of inhibiting TNFα in this manner, and may also be used as target engagement biomarkers.

Accordingly, the present invention provides an antibody that selectively binds to a complex comprising (i) a trimeric protein that is a TNF superfamily member and (ii) a compound that is capable of binding to a trimeric protein that is a TNF superfamily member, whereby the compound-trimer complex binds to the requisite TNF superfamily receptor and modulates the signalling induced by the trimer through the receptor.

The present invention also provides an antibody that selectively binds to a complex comprising (i) a human TNFα and (ii) a compound selected from the group consisting of compounds (1)-(6), or salts or solvates thereof.

The invention further provides

An antibody which competes for binding to TNFα with, or binds to the same epitope on TNFα as, other antibodies of the invention.

An isolated polynucleotide encoding an antibody of the invention.

An antibody of the invention for use in a method of treatment of the human or animal body by therapy.

A pharmaceutical composition comprising an antibody of the invention and a pharmaceutically acceptable adjuvant and/or carrier.

Use of an antibody of the invention as a target engagement biomarker for the detection of a compound-trimer complex in a sample obtained from a subject; wherein said antibody is detectable and said complex comprises a trimeric protein that is a TNF superfamily member and a compound that is capable of binding to a trimeric protein that is a TNF superfamily member, whereby the compound-trimer complex binds to the requisite TNF superfamily receptor and modulates the signalling induced by the trimer through the receptor.

A method of detecting target engagement of a compound to a trimeric TNF superfamily member, whereby the compound-trimer complex binds to the requisite receptor and modulates the signalling induced by the trimer through the receptor, said method comprising:
(a) obtaining a sample from a subject administered said compound;
(b) contacting an antibody of the invention to said sample and a control sample, wherein said antibody is detectable;
(c) determining the amount of binding of said detectable antibody to said sample and said control sample, wherein binding of said detectable antibody to said sample greater than binding of said detectable antibody to said control sample indicates target engagement of said compound to said trimeric TNF superfamily member.

Use of an antibody of the invention in screening for a compound that elicits a conformational change in a trimeric TNF superfamily member, wherein said conformational change modulates the signalling of the requisite TNF superfamily receptor on binding of the trimeric TNF superfamily member.

A complex comprising a trimeric protein that is a TNF superfamily member and a compound that is bound thereto, whereby the compound-trimer complex binds to the requisite TNF superfamily receptor and modulates the signalling induced by the trimer through the receptor, wherein said complex binds to an antibody of the invention with a $K_{D\text{-}ab}$ of 1 nM or less.

A TNFα trimer, said TNFα trimer being able to bind TNFR1, but wherein signalling from said bound TNFR1 is attenuated or antagonised, wherein said TNFα trimer binds to either or both of the following antibodies with a $K_{D\text{-}ab}$ of 1 nM or less:
(i) an antibody with a heavy chain of SEQ ID NO: 27 and a light chain of SEQ ID NO: 26; or
(ii) an antibody with a heavy chain of SEQ ID NO: 12 and a light chain of SEQ ID NO: 11.

A compound that is capable of binding to a trimeric protein that is a TNF superfamily member to form a complex, whereby the compound-trimer complex binds to the requisite TNF superfamily receptor and modulates the signalling induced by the trimer through the receptor, wherein the compound-trimer complex binds to an antibody of the invention with a $K_{D\text{-}ab}$ of 1 nM or less.

A complex as defined above, a trimer as defined above, or a compound according as defined above for use in a method of therapy practiced on the human or animal body.

A method of identifying a compound that is capable of binding to a trimeric protein that is a TNF superfamily member and modulating signalling of the trimeric protein through the receptor, comprising the steps of:

(a) performing a binding assay to measure the binding affinity of a test compound-trimer complex comprising a trimeric protein that is a TNF superfamily member and a test compound to an antibody that selectively binds to said complex;

(b) comparing the binding affinity as measured in step (a) with the binding affinity of a different compound-trimer complex known to bind with high affinity to the antibody referred to in step (a); and (c) selecting the compound present in the compound-trimer complex of step (a) if its measured binding affinity is acceptable when considered in the light of the comparison referred to in step (b).

BRIEF DESCRIPTION OF THE FIGURES

FIG. 1 highlights residues N168, I194, F220 and A221 on the crystal structure of human TNFα.

FIG. 2 shows results of HPLC experiments with the CA185_01974 mFab and compound (1). Peaks corresponding to excess Fab appear at a 1.5× and 2.0× excess. The stoichiometry was therefore determined to be 1 Fab: 1 TNFα trimer.

FIG. 3 shows results of HPLC experiments with the CA185_01979 mFab and compound (1). Again, peaks corresponding to excess Fab appear at a 1.5× and 2.0× excess. The stoichiometry was therefore also determined to be 1 Fab: 1 TNFα trimer.

FIG. 4 presents results of total TNFα ELISA with compounds (3), (4) and (5) using a commercial anti-TNFα polyclonal antibody.

FIG. 5 presents results of conformation specific TNFα ELISA with CA185_01974.0 and compounds (3), (4) and (5). Apo TNFα gave no signal in this assay, demonstrating the specific nature of the binding of antibody CA185_01974 to compound-bound TNFα.

FIG. 6 shows FACS histogram plots of staining with CA185_01974 and CA185_01979 at 1 and 10 μg/ml. These plots demonstrate that the antibodies only recognise TNFα which has been pre-incubated with compound (1). There is no staining with the DMSO control.

FIG. 7 shows FACS histogram plots of staining with CA185_01974 for a parental NS0 cell line and an engineered NS0 cell line, which overexpresses membrane TNFα. Cells were incubated with compound (1) or DMSO and stained with the antibody Fab fragment. Again, results indicate no staining for the DMSO control (for either the parental or engineered cell line). In the presence of compound (1) staining is, however, observed for the engineered cell line.

FIG. 8 shows sensograms for the determination of affinity values for CA185_01974 using cynomolgus TNFα. Controls (top panels) contained cynomolgus TNFα and DMSO. The bottom panels then present duplicated experiments for cynomolgus TNFα complexed with compound (4).

FIG. 9 shows sensograms for the determination of affinity values for CA185_01974 using human TNFα. Controls (top panels) contained human TNFα and DMSO. The bottom panels then present duplicated experiments for human TNFα complexed with compound (4).

Figure 10:
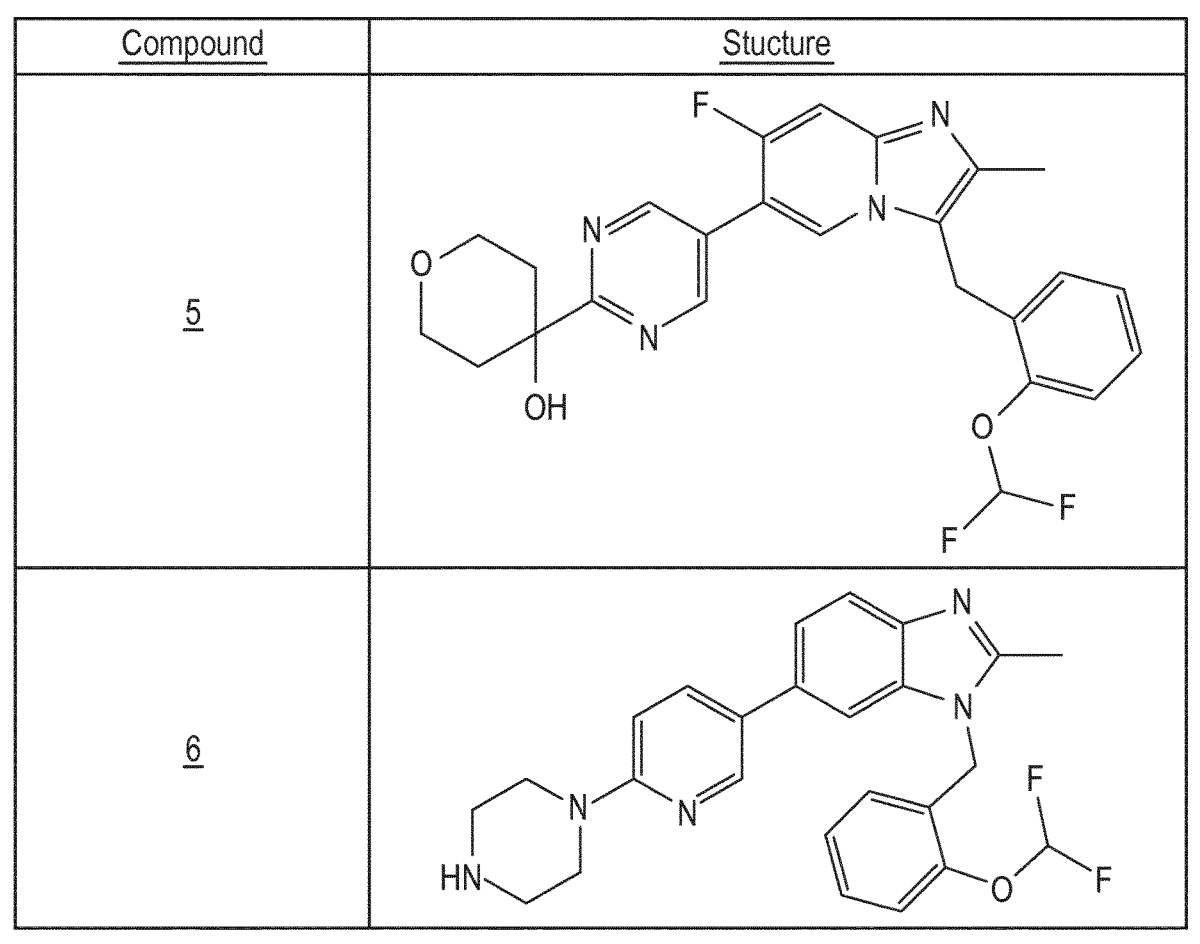

FIG. 10 shows the structures of compounds (1)-(6).

BRIEF DESCRIPTION OF THE SEQUENCE LISTING

SEQ ID NO: 1 shows the LCDR1 of CA185_01974.0.

SEQ ID NO: 2 shows the LCDR2 of CA185_01974.0.

SEQ ID NO: 3 shows the LCDR3 of CA185_01974.0.

SEQ ID NO: 4 shows the HCDR1 of CA185_01974.0.

SEQ ID NO: 5 shows the HCDR2 of CA185_01974.0.

SEQ ID NO: 6 shows the HCDR3 of CA185_01974.0.

SEQ ID NO: 7 shows the amino acid sequence of the LCVR of CA185_01974.0.

SEQ ID NO: 8 shows the amino acid sequence of the HCVR of CA185_01974.0.

SEQ ID NO: 9 shows the DNA sequence of the LCVR of CA185_01974.0.

SEQ ID NO: 10 shows the DNA sequence of the HCVR of CA185_01974.0.

SEQ ID NO: 11 shows the amino acid sequence of the kappa light chain of CA185_01974.0.

SEQ ID NO: 12 shows the amino acid sequence of the mIgG1 heavy chain of CA185_01974.0.

SEQ ID NO: 13 shows the amino acid sequence of the mFab (no hinge) heavy chain of CA185_01974.0.

SEQ ID NO: 14 shows the DNA sequence of the kappa light chain of CA185_01974.0.

SEQ ID NO: 15 shows the DNA sequence of the mIgG1 heavy chain of CA185_01974.0.

SEQ ID NO: 16 shows the DNA sequence of the mFab (no hinge) heavy chain of CA185_01974.0.

SEQ ID NO: 17 shows the LCDR2 of CA185_01979.0.

SEQ ID NO: 18 shows the LCDR3 of CA185_01979.0.

SEQ ID NO: 19 shows the HCDR1 of CA185_01979.0.

SEQ ID NO: 20 shows the HCDR2 of CA185_01979.0.

SEQ ID NO: 21 shows the HCDR3 of CA185_01979.0.

SEQ ID NO: 22 shows the amino acid sequence of the LCVR of CA185_01979.0.

SEQ ID NO: 23 shows the amino acid sequence of the HCVR of CA185_01979.0.

SEQ ID NO: 24 shows the DNA sequence of the LCVR of CA185_01979.0.

SEQ ID NO: 25 shows the DNA sequence of the HCVR of CA185_01979.0.

SEQ ID NO: 26 shows the amino acid sequence of the kappa light chain of CA185_01979.0.

SEQ ID NO: 27 shows the amino acid sequence of the mIgG1 heavy chain of CA185_01979.0.

SEQ ID NO: 28 shows the amino acid sequence of the mFab (no hinge) heavy chain of CA185_01979.0.

SEQ ID NO: 29 shows the DNA sequence of the kappa light chain of CA185_01979.0.

SEQ ID NO: 30 shows the DNA sequence of the mIgG1 heavy chain of CA185_01979.0.

SEQ ID NO: 31 shows the DNA sequence of the mFab (no hinge) heavy chain of CA185_01979.0.

SEQ ID NO: 32 shows the amino acid sequence of rat TNFα.

SEQ ID NO: 33 shows the amino acid sequence of mouse TNFα.

SEQ ID NO: 34 shows the amino acid sequence of human TNFα.

SEQ ID NO: 35 shows the amino acid sequence of the soluble form of human TNFα.

SEQ ID NO: 36 shows the amino acid sequence of the soluble form of human TNFα, but without the initial "S" (which is a cloning artefact in SEQ ID NO: 35)

DETAILED DESCRIPTION OF THE INVENTION

Modulators of TNF Superfamily Members

The present inventors have identified test compounds that bind to trimeric forms of the TNF superfamily members. These compounds are small molecular entities (SMEs) that have a molecular weight of 1000 Da or less, generally 750 Da or less, more suitably 600 Da or less. The molecular weight may be in the range of about 50-about 1000 Da, or about 100-about 1000 Da. These compounds stabilise a conformation of the trimeric TNF superfamily member that binds to the requisite TNF superfamily receptor and modulate the signalling of the receptor. Examples of such compounds include compounds of formulae (1)-(6).

The stabilising effect of compounds of the invention on trimeric forms of TNF superfamily members may be quantified by measuring the thermal transition midpoint (Tm) of the trimers in the presence and absence of the compound. Tm signifies the temperature at which 50% of the biomolecules are unfolded. Compounds which stabilise TNF superfamily member trimers will increase the Tm of the trimers. Tm may be determined using any appropriate technique known in the art, for example using differential scanning calorimetry (DSC) or fluorescence probed thermal denaturation assays.

The compounds may bind inside the central space present within the TNF superfamily member trimer (i.e. the core of the trimer).

These compounds may turn the TNF superfamily member into a TNF superfamily receptor antagonist. These compounds are therefore capable of blocking the TNF superfamily member signalling without having to compete with the high affinity interaction between the TNF superfamily member and its receptor.

Alternatively, the compounds may stabilise a conformation of the trimeric TNF superfamily member that binds to the requisite TNF superfamily receptor and enhances the signalling of the receptor. These compounds are therefore capable of increasing the TNF superfamily member signalling without having to compete with the high affinity interaction between the TNF superfamily member and its receptor.

Where herein the compounds are described as antagonists, it will be understood that the compounds may equally be agonists and increase signalling by a TNF superfamily receptor that is bound to a complex of a TNF superfamily member trimer and such an agonist compound. Similarly, where other disclosure refers to antagonistic compounds, methods of identifying such compounds and uses of such compounds, this disclosure may refer equally to agonist compounds.

The compounds described herein are allosteric modulators that bind to the natural agonists of the TNF superfamily receptors, i.e. to trimeric forms of TNF superfamily members and drive these trimers to adopt a conformation that still binds to the requisite TNF superfamily receptor and modulates signalling by the receptor. By modulating, it will be understood that the compound may have an antagonistic effect and so decrease signalling by a TNF superfamily receptor, or else a stimulatory effect and so increase or enhance signalling by a TNF superfamily receptor.

These compounds may convert the natural TNF superfamily member agonists into antagonists. In contrast, conventional TNF superfamily member antagonists bind to the TNF superfamily member or the TNF superfamily receptor and prevent the binding of the TNF superfamily member to the requisite receptor. In the alternative, the compounds may increase signalling by a TNF superfamily receptor when the TNF superfamily member is bound compared to the level of signalling by the TNF superfamily receptor when the TNF superfamily member is bound in the absence of the compound. The compounds may therefore convert the natural TNF superfamily member agonists into so-called "superagonists". The compounds may therefore also be known as allosteric modulators of ligand activity (AMLAs).

The compounds are not limited in terms of their chemical formula or structure, provided that they bind to at least one TNF superfamily member and stabilise a conformation of the trimeric TNF superfamily member that binds to the requisite TNF superfamily receptor and modulate the signalling of the TNF superfamily receptor. The compounds can therefore be identified using the antibodies and methods described herein. The compounds may comprise a benzimidazole moiety or an isostere thereof.

The compounds may increase the binding affinity of TNF superfamily members (in the form of a compound-trimer complex) to the requisite receptor compared to the binding affinity of the TNF superfamily members to the requisite receptor in the absence of the compounds.

The compounds bind to the trimeric forms of TNF superfamily members. Such compounds may bind specifically (or selectively) to the trimeric forms of one or more TNF superfamily members. A compound may bind specifically (or selectively) to only one of the TNF superfamily members, but not to any other TNF superfamily members. A compound may also bind specifically to two, three, four or up to all of the TNF superfamily members. By specific (or selective), it will be understood that the compounds bind to the molecule or molecules of interest, in this case the trimeric form of the TNF superfamily member, with no significant cross-reactivity to any other molecule, which may include other members of the TNF superfamily. Cross-reactivity may be assessed by any suitable method, for example surface plasmon resonance. Cross-reactivity of a compound for the trimeric form of a TNF superfamily member with a molecule other than the trimeric form of that particular TNF superfamily member may be considered significant if the compound binds to the other molecule at least about 5%, 10%, 15%, 20%, 25%, 30%, 35%, 40%, 45%, 50%, 55%, 60%, 65%, 70%, 75%, 80%, 85%, 90% or 100% as strongly as it binds to the trimeric form of the TNF superfamily member of interest. For example, cross reactivity may be considered significant if the compound binds to the other molecule about 5%-about 100%, typically about 20%-about 100%, or about 50%-about 100% as strongly as it binds to the trimeric form of the TNF superfamily member of interest. A compound that is specific (or selective) for the trimeric form of a TNF superfamily member may bind to another molecule at less than about 90%, 85%, 80%, 75%, 70%, 65%, 60%, 55%, 50%, 45%, 40%, 35%, 30%, 25% or 20% the strength that it binds to the trimeric form of the TNF superfamily member (down to zero binding). The compound suitably binds to the other molecule at less than about 20%, less than about 15%, less than about 10% or less than about 5%, less than about 2% or less than about 1% the strength that it binds to the trimeric form of the TNF superfamily member (down to zero binding).

The rates at which a test compound binds to a TNF superfamily member is referred to herein as the "on" rate" $k_{on-c}$ and the rate at which the test compound dissociates from the TNF superfamily member is referred to herein as the "off" rate or $k_{off-c}$. As used herein, the symbol "$K_{D-c}$" denotes the binding affinity (dissociation constant) of a test compound for a TNF superfamily member. $K_{D-c}$ is defined as $k_{off-c}/k_{on-c}$. Test compounds may have slow "on" rates, which can be measured in minutes by mass spectral analysis of the TNF superfamily member and compound-trimer complex peak intensities. $K_{D-c}$ values for a test compound can be estimated by repeating this measurement at different TNF superfamily member: compound-trimer complex ratios. Typically, binding of compounds of the invention to TNF superfamily trimers is characterized by fast "on" rates, ideally about $10^7$ $M^{-1}s^{-1}$, with slow "off" rate, for example values typically of $10^{-3}$ $s^{-1}$, $10^{-4}$ $s^{-1}$, or no measurable "off" rate.

As used herein, the symbol "$k_{on-r}$" denotes the rate (the "on" rate) at which a compound-trimer complex binds to a TNF superfamily receptor. As used herein, the symbol "$k_{off-r}$" denotes the rate (the "off" rate) at which a compound-trimer complex dissociates from a TNF superfamily receptor. As used herein, the symbol "$K_{D-r}$" denotes the binding affinity (dissociation constant) of a compound-trimer complex for a superfamily receptor. $K_{D-r}$ is defined as $k_{off-r}/k_{on-r}$.

The $K_{D-r}$ value of the TNF superfamily member for binding to its receptor in the presence of the test compound (i.e. in the form of a compound-trimer complex) may be at least about 1.5 times, 2 times, 3 times, 4 times, 5 times, 10 times, 20 times, 30 times, 40 times, 50 times, 60 times, 70 times, 80 times, 90 times, 100 times lower than the $K_{D-r}$ value of the TNF superfamily member for binding to its receptor in the absence of the test compound. The $K_{D-r}$ value of the compound-trimer complex for binding to the TNF superfamily member may be decreased at least about 1.5 times, generally at least about 3 times, more suitably at least about 4 times the $K_{D-r}$ value of the TNF superfamily trimer binding to the TNF superfamily receptor in the absence of the test compound, i.e. the binding affinity of the compound-trimer complex for the TNF superfamily may be increased at least about 1.5-fold, generally at least about three-fold, more suitably at least about four-fold compared to the binding affinity of the TNF superfamily trimer to the TNF superfamily receptor in the absence of test compound.

A compound described herein may increase the binding affinity of the TNF superfamily member to its receptor by about 2 times, 3 times, 4 times, 5 times, 10 times, 20 times, 30 times, 40 times, 50 times, 60 times, 70 times, 80 times, 90 times, 100 times or more compared to the binding affinity of the TNF superfamily member to its receptor in the absence of the compound.

The binding affinity may be given in terms of binding affinities ($K_{D-r}$) and may be given in any appropriate units, such as µM, nM or pM. The smaller the $K_{D-r}$ value, the larger the binding affinity of the TNF superfamily member to its receptor.

The $K_{D-r}$ value of the TNF superfamily member for binding to its receptor in the presence of the compound may be at least about 1.5 times, 2 times, 3 times, 4 times, 5 times, 10 times, 20 times, 30 times, 40 times, 50 times, 60 times, 70 times, 80 times, 90 times, 100 times lower than the $K_{D-r}$ value of the TNF superfamily member for binding to its receptor in the absence of the test compound.

The decrease in the $K_{D-r}$ value of the compound-trimer complex for binding to the TNF superfamily receptor compared to the $K_{D-r}$ value of the TNF superfamily trimer alone binding to the TNF superfamily receptor may result from an increase in the on rate ($k_{on-r}$) of the compound-trimer complex binding to the TNF superfamily receptor compared to the TNF superfamily trimer alone, and/or a decrease in the off rate ($k_{off-r}$) compared to the TNF superfamily trimer alone. The on rate ($k_{on-r}$) of the compound-trimer complex binding to the TNF superfamily receptor is generally increased compared to the TNF superfamily trimer alone. The off rate ($k_{off-r}$) of the compound-trimer complex binding to the TNF superfamily receptor is generally decreased compared to the TNF superfamily trimer alone. Most suitably, the on rate ($k_{on-r}$) of the compound-trimer complex binding to the TNF superfamily receptor is increased, and the off-rate ($k_{off-r}$) of the compound-trimer complex binding to the TNF superfamily receptor is decreased, compared to the TNF superfamily trimer alone. The $k_{on-r}$ value of the compound-trimer complex to the requisite TNF superfamily receptor may be increased by at least about 1.5-fold or at least about two-fold and suitably at least about three fold compared to the $k_{on-r}$ value of the TNF superfamily trimer binding to its receptor in the absence of the compound and/or the $k_{off-r}$ value of the compound-trimer complex to the requisite TNF superfamily receptor may be decreased by at least about 1.2-fold, at least about 1.6-fold, at least about two-fold, more suitably at least about 2.4-fold compared to the $k_{off-r}$ value of the TNF superfamily trimer binding to its receptor in the absence of the compound.

The on-rate for compound binding to TNF superfamily trimer ($k_{on-c}$) is typically faster than the on-rate for compound-trimer complex binding to TNF superfamily receptor ($k_{on-r}$). The off-rate for compound-trimer complex binding to TNF superfamily receptor ($k_{off-r}$) is also typically faster than the off-rate for compound binding to TNF superfamily trimer ($k_{off-c}$). Most suitably, the on-rate for compound binding to TNF superfamily trimer ($k_{on-c}$) is faster than the on-rate for compound-trimer complex binding to TNF superfamily receptor ($k_{on-r}$), and the off-rate for compound-trimer complex binding to TNF superfamily receptor ($k_{off-r}$) is faster than the off-rate for compound binding to TNF superfamily trimer ($k_{off-c}$). The $K_{D-c}$ value of the compound for binding to TNF superfamily trimer is generally lower than the $K_{D-r}$ value of the compound-trimer complex for binding to TNF superfamily receptor, i.e. the compound has a higher affinity for the trimer than the compound-trimer complex has for the receptor.

The $k_{on-r}$, $k_{off-r}$, and $K_{D-r}$ values for both the compound-trimer complex and the TNF superfamily trimer to the requisite TNF superfamily receptor may be determined using any appropriate technique, for example surface plasmon resonance, mass spectrometry and isothermal calorimetry. The $K_{D-r}$ value of the TNF superfamily member for binding to its receptor in the presence of the test compound may be 1 µM, 100 nM, 10 nM, 5 nM, 1 nM, 100 pM, 10 pM or less (typically down to a lower value of about 1 pM). The $K_{D-r}$ value of the TNF superfamily member for binding to its receptor in the presence of the test compound (i.e. in a compound-trimer complex) may be 1 nM or less. The $K_{D-r}$ value of a compound-trimer complex for binding to the requisite TNF superfamily receptor may be less than 600 pM, more preferably less than 500 pM, less than 400 pM, less than 300 pM, less than 200 pM, less than 100 pM or less than 50 pM (again down to a lower value of about 1 pM). The $K_{D-r}$ value of a compound-trimer complex for binding to the requisite TNF superfamily receptor may be less than about 200 pM (to about 1 pM).

Compounds may be identified by an assay which comprises determining the $K_{D-r}$ of the trimeric form of the TNF superfamily member in a sample of the TNF superfamily member and the compound; comparing the $K_{D-r}$ of the trimeric form of the TNF superfamily member in the sample with a control sample; and selecting a compound.

The compounds stabilise the trimeric form of the TNF superfamily member. Stabilisation is considered to occur if a test compound increases the proportion of trimer compared to the amount of trimer observed for a sample containing the TNF superfamily member and the destabilising agent in the absence of the test compound. The test compound may increase the amount of trimer by about 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of trimer present in a sample containing the TNF superfamily member and the destabilising agent in the absence of the test compound.

The test compound may also increase the amount of trimer compared to that observed for a sample of the TNF superfamily member in the absence of both the destabilising agent and the test compound. The test compound may increase the amount of trimer by about 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of trimer present in a sample containing the TNF superfamily member in the absence of both the destabilising agent and the test compound.

The test compound may increase the amount of the TNF superfamily member bound to its receptor by about 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of the TNF superfamily member bound to its receptor in a sample containing the TNF superfamily member in the absence of the test compound.

The test compounds may enhance the stability of the trimeric form of the TNF superfamily member. Enhanced stability of the trimeric form of the TNF superfamily member is considered to occur if a test compound increases the thermal transition midpoint ($T_m$) of the trimeric form of the TNF superfamily member compared to the $T_m$ of the trimeric form of the TNF superfamily member observed for a sample containing the TNF superfamily member and the destabilising agent in the absence of the test compound. The $T_m$ of the trimeric form of the TNF superfamily member is the temperature at which 50% of the biomolecules are unfolded. The $T_m$ of the trimeric form of the TNF superfamily member in the presence and/or absence of the test compound may be measured using any appropriate technique known in the art, for example using differential scanning calorimetry (DSC) or fluorescence probed thermal denaturation assays.

The test compound may increase the $T_m$ of the trimeric form of the TNF superfamily member by at least 1° C., at least 2° C., at least 5° C., at least 10° C., at least 15° C., at least 20° C. or more compared to the $T_m$ of the trimeric form of the TNF superfamily member in a sample containing the TNF superfamily member in the absence of the test compound. The test compound may increase the $T_m$ of the trimeric form of the TNF superfamily member by at least 1° C., typically by at least 10° C. and more suitably by between 10° C. and 20° C.

The compounds may completely or partially inhibit signalling through a TNF receptor when a TNF superfamily member in the form of a compound-trimer complex binds to the receptor. The compound may act to reduce signalling through a TNF superfamily receptor by at least about 10%, 20%, 30%, 40%, 50%, 60%, 70%, 80%, 90% or 100%. Alternatively, the compounds may increase signalling through a TNF receptor when a TNF superfamily member in the form of a compound-trimer complex binds to the receptor. The compound may act to increase signalling through a TNF superfamily receptor by at least about 10%, 20%, 30%, 40%, 50%, 60%, 70%, 80%, 90%, 100% or 200%. Any change in the level of signalling may be measured by any appropriate technique, including measuring reporter gene activity by alkaline phosphatase or luciferase, NF-κB translocation using machines such as the Cellomics Arrayscan, phosphorylation of downstream effectors, recruitment of signalling molecules, or cell death.

The compounds may modulate at least one of the downstream effects of signalling through a TNF receptor when a TNF superfamily member in the form of a compound-trimer complex binds to the receptor. Such effects are discussed herein and include TNF superfamily-induced IL-8, IL17A/F, IL2 and VCAM production, TNF superfamily-induced NF-κB activation and neutrophil recruitment. Standard techniques are known in the art for measuring the downstream effects of TNF superfamily members. The compounds may modulate at least 1, 2, 3, 4, 5, 10 or up to all of the downstream effects of signalling through a TNF receptor.

The activity of the compounds may be quantified using standard terminology, such as $IC_{50}$ or half maximal effective concentration ($EC_{50}$) values. $IC_{50}$ values represent the concentration of a compound that is required for 50% inhibition of a specified biological or biochemical function. $EC_{50}$ values represent the concentration of a compound that is required for 50% of its maximal effect. The compounds may have $IC_{50}$ or $EC_{50}$ values of 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 100 pM or less (down to a lower value of about 10 pM or 1 pM). $IC_{50}$ and $EC_{50}$ values may be measured using any appropriate technique, for example cytokine production can be quantified using ELISA. $IC_{50}$ and $EC_{50}$ values can then be generated using a standard 4-parameter logistic model also known as the sigmoidal dose response model.

As mentioned above, examples of compounds which are capable of binding to TNF and modulating signalling are compounds of formulae (1)-(6).

Modulator-TNF Superfamily Member Complexes

The present inventors have found that binding of the compounds described herein to trimeric forms of TNF superfamily members results in a conformational change in the TNF superfamily trimer. In particular, the TNF superfamily member trimer takes on a deformed or distorted conformation when bound by a compound as disclosed herein.

For example, when compounds (1)-(6) are bound the soluble domain of human TNFα the TNF retains its trimeric structure but the A and C subunits move away from each other and C rotates to generate a cleft between these subunits.

Without being bound by theory, it is believed that, in the absence of a compound, trimeric TNF superfamily members, including trimeric TNFα, are capable of binding to three separate dimeric TNF superfamily member receptors. Each of the dimeric TNF superfamily member receptors is capable of binding to two separate TNF superfamily trimers. This results in the aggregation of multiple TNF superfamily member trimers and TNF superfamily member receptor dimers, creating signalling rafts that initiate downstream signalling.

When trimeric TNFα is bound to the compound, the conformation of the resulting complex is deformed. Accordingly, without being bound by theory, it is believed that, in the presence of a compound as disclosed herein, trimeric TNF superfamily members, including trimeric TNFα, are only capable of binding to two separate dimeric TNF superfamily member receptors. The fact that only two, rather than three, separate dimeric TNF superfamily member receptors bind to the trimeric TNF superfamily member reduces or inhibiting the aggregation of multiple TNF superfamily member trimers and TNF superfamily member receptor dimers. This reduces or inhibits the formation of signalling rafts and so reduces or inhibits downstream signalling.

The antibodies of the invention may be used to detect TNF superfamily members with a distorted conformation as a result of the binding of a compound as disclosed herein. Typically the TNF superfamily member with a distorted or deformed conformation is a trimeric TNF superfamily member. However, antibodies of the invention may also bind to other forms of the TNF superfamily member. For example, antibodies of the invention may bind to TNF superfamily monomers.

The TNF superfamily member is typically TNFα, and may be trimeric TNFα (particularly $TNF\alpha_s$).

Accordingly, the invention provides a complex comprising a trimeric protein that is a TNF superfamily member and a compound that is bound thereto, whereby the compound-trimer complex binds to the requisite TNF superfamily receptor and modulates the signalling induced by the trimer through the receptor, wherein said complex binds to an antibody of the invention with an affinity of at least 1 nM (i.e. 1 nM or less, down to about 1 pM). The TNF superfamily member is typically TNFα, more particularly $TNF\alpha_s$.

Furthermore, the antibody generally binds to the complex with an affinity of that is at least about 100 times lower (the affinity is improved at least about 100 times), suitably about 200 times lower, relative to the affinity for binding to the compound in the absence of the TNF timer and/or for binding to the TNF trimer in the absence of compound.

The present invention further provides a compound that is capable of binding to a trimeric protein that is a TNF superfamily member to form a complex, whereby the compound-trimer complex binds to the requisite TNF superfamily receptor and modulates the signalling induced by the trimer through the receptor, wherein the compound-trimer complex binds to an antibody of the invention with a $K_{D-ab}$ of 1 nM or less (down to about 1 pM). The TNF superfamily member is typically TNFα, most particularly $TNF\alpha_s$.

The antibody typically binds to the complex with an affinity of that is at least about 100 times lower (the affinity is improved at least about 100 times), more suitably about 200 times lower, relative to the affinity for binding to the compound in the absence of the TNF timer and/or for binding to the TNF trimer in the absence of compound.

The compound-trimer complex may bind to any antibody of the invention. Particularly, the compound-trimer complex may bind to an antibody comprising the amino acid sequences disclosed herein.

A compound or complex described herein may be used in the treatment and/or prophylaxis of a pathological condition. Accordingly, provided is a compound or complex of the invention for use in a method of therapy practiced on the human or animal body. The invention also provides a method of therapy comprising the administration of a compound or complex of the invention to a subject. The compound or complex of the invention may be used in any therapeutic indication and/or pharmaceutical composition described herein.

Antibodies

The invention provides antibodies that selectively bind to at least one compound-trimer complex comprising at least one compound disclosed herein and a trimeric TNF superfamily member.

Typically, selective binding of an antibody of the invention to a compound-(trimer) complex is measured relative to the binding of the antibody to the compound in the absence of the TNF superfamily member, or to the TNF superfamily member in the absence of the compound or to other (different) compound-(trimer) complexes.

In particular, the invention provides an antibody that selectively binds to a complex comprising (i) a trimeric protein that is a TNF superfamily member and (ii) a compound that is capable of binding to a trimeric protein that is a TNF superfamily member, whereby the compound-trimer complex binds to the requisite TNF superfamily receptor and modulates the signalling induced by the trimer through the receptor. Typically said antibody binds selectively to said complex relative to its binding to the TNF superfamily member in the absence of the compound or to the compound in the absence of the TNF superfamily member.

The compound may be any compound described above, including compounds (1)-(6) (or salts or solvates thereof). As discussed further below, the TNF superfamily member may be any of the superfamily members, but is typically TNFα. More particularly, the TNFα is human TNFα, especially soluble TNFα ($TNF\alpha_s$). The $TNF\alpha_s$ may have the sequence of SEQ ID NO: 35 or SEQ ID NO: 36, or may be a variant of SEQ ID NO: 35 or SEQ ID NO: 36. Such variants typically retain at least about 60%, 70%, 80%, 90%, 91%, 92%, 93%, 94% or 95% identity to SEQ ID NO: 35 or SEQ ID NO: 36 (or even about 96%, 97%, 98% or 99% identity). In other words, such variants may retain about 60%-about 99% identity to SEQ ID NO:35 or SEQ ID NO:36, suitably about 80%-about 99% identity to SEQ ID NO:35 or SEQ ID NO:36, more suitably about 90%-about 99% identity to SEQ ID NO:35 or SEQ ID NO:36 and most suitably about 95%-about 99% identity to SEQ ID NO:35 or SEQ ID NO:36. Variants are described further below.

The term "corresponding sequence" indicates that the TNFα may have the wild-type amino sequence of any known animal or human TNFα, in particular human TNFα, for instance SEQ ID NO: 36. It may be soluble TNFα (sTNFα) or membrane-bound TNFα, or both. Soluble homotrimeric TNFα (sTNF) is released from membrane-bound homotrimeric TNFα (mTNF) via proteolytic cleavage by the metalloprotease TNF alpha converting enzyme (TACE/ADAM17; though other proteinases can also release sTNF such as ADAM10, ADAM19, matrix metalloproteinase 7 and proteinase 3 which may yield corresponding soluble TNFα sequences that may be extended or truncated by 1, 2, 3, 4, or 5 amino acids relative to a TACE cleaved sTNFα such as SEQ ID NO: 36). The soluble 52 kDa trimeric sTNF takes on a triangular pyramid shape. A human sequence encompassed by the term mTNF is shown in SEQ ID NO: 34, and a human sequence encompassed by the term sTNF (the product of the action of TACE on SEQ ID NO: 34) is shown in SEQ ID NO: 36. Corresponding sequences of rat and mouse mTNFα are presented in SEQ ID NO:32 and 33, respectively. Corresponding sequences of TNFα from other animals (or known variants of the human sequence) may be readily overlaid with the SEQ ID NO:36 sequence and given the same amino acid numbering as for SEQ ID NO:36 (used in the numbering of TNFα amino acids herein). For instance, the sequence from various animals may be found within the Uniprot database (www.uniprot.org) including human sequences P01375 and Q5STB3. The corresponding sTNFα sequences may be the 157 amino acid C-terminal end of the mTNFα sequence (as SEQ ID NO:36) or may be longer or shorter by one, two or three amino acids (the rat and mouse sequences being 156 amino acids). The corresponding sTNFα sequence may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid substitutions relative to SEQ ID NO:36. The corresponding sTNFα sequence may have 80, 90, 95, 96, 97, 98, or 99% amino acid sequence identity to SEQ ID NO:36 over the length of SEQ ID NO:36.

As discussed above, although the present disclosure generally relates to binding of antibodies of the invention to TNF superfamily member trimers, antibodies of the invention may also bind to other forms of the TNF superfamily member. To illustrate, the Examples of the present application demonstrate that the CA185_0179 antibody binds to trimeric TNF. However, as shown in FIG. 1 (crystal structure of the CA185_0179 antibody bound to a TNFα monomer in the presence of compound (1)) the antibody also appears to bind to monomeric TNFα. Without being bound by theory, in the presence of the compound it is believed that the soluble domain of the TNF retains its trimeric structure. However, the A and C subunits move away from each other (and the C subunit rotates) to generate a cleft between these two subunits. Thus although antibodies of the invention bind to distorted trimers, it is also possible that the antibodies can still bind if the trimeric structure is forced apart into monomers.

With regards to the "A" and "C" subunits, when looking at a crystal structure of a TNFα trimer from the side it is approximately shaped like a pyramid/cone. When you look down the trimer axis with the N- and C-termini of the monomer ends pointing towards you then you are looking at the "fat" end of the trimer. In the distorted structure with compound, a cleft opens between A and C subunits in which, without being bound by theory, the Ab of the invention binds.

Which chain is A, B or C may be ascertained by measuring three distances between three C-alpha atoms of three identical residues—e.g. P117 in each chain (G121 is also appropriate).

The three distances form a triangle which is equilateral in apo TNF but distorted when compound is bound. The shortest distance is between BC and the longest between AC (for instance AC=13.8 Å, AB=12.3 Å, BC=10.2 Å); thus looking down through the axis of the molecule with N/C termini pointing towards you the longest distance defines C then A chains going anti-clockwise, then B and C again continuing anti-clockwise.

The invention therefore also provides antibodies that selectively bind to a complex comprising human TNFα and a compound selected from the group consisting of compounds (1)-(6), or salts or solvates thereof. The human TNFα is typically soluble TNFα (TNFα$_s$). The TNFα$_s$ may comprise the sequence of SEQ ID NO: 35 or SEQ ID NO: 36, or a variant thereof. Such variants may retain at least about 60%, 70%, 80%, 90%, 91%, 92%, 93%, 94%, 95%, 96%, 97%, 98% or 99% identity to SEQ ID NO:35 or SEQ ID NO: 36 (see above and methods of identifying variants are described below). The TNFα may be trimeric.

The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as HCVR or $V_H$) and a heavy chain constant region. Each light chain is comprised of a light chain variable region (abbreviated herein as LCVR or $V_L$) and a light chain constant region. The variable regions of the heavy and light chains contain a binding domain that interacts with an antigen. The $V_H$ and $V_L$ regions can be further subdivided into regions of hypervariability, termed complementarity determining regions (CDR), interspersed with regions that are more conserved, termed framework regions (FR).

The constant regions of the antibodies may mediate the binding of the immunoglobulin to host tissues or factors, including various cells of the immune system (e.g., effector cells) and the first component (Clq) of the classical complement system.

An antibody of the invention may be a monoclonal antibody or a polyclonal antibody, and will typically be a monoclonal antibody. An antibody of the invention may be a chimeric antibody, a CDR-grafted antibody, a nanobody, a human or humanised antibody or an antigen-binding portion of any thereof. For the production of both monoclonal and polyclonal antibodies, the experimental animal is typically a non-human mammal such as a goat, rabbit, rat or mouse but the antibody may also be raised in other species.

Polyclonal antibodies may be produced by routine methods such as immunisation of a suitable animal, with the antigen of interest. Blood may be subsequently removed from the animal and the IgG fraction purified.

Antibodies generated against compound-trimer complexes of the invention may be obtained, where immunisation of an animal is necessary, by administering the polypeptides to an animal, e.g. a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies of the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and WO2004/106377.

The antibodies of the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, but not necessarily from the same antibody. Examples of fully human antibodies may include antibodies produced, for example by the phage display methods described above and antibodies produced by mice in which the murine immunoglobulin variable and optionally the constant region genes have been replaced by their human counterparts e.g. as described in general terms in EP 0546073, U.S. Pat. Nos. 5,545,806, 5,569,825, 5,625,126, 5,633,425, 5,661,016, 5,770,429, EP 0438474 and EP 0463151.

Alternatively, an antibody according to the invention may be produced by a method comprising: immunizing a non-human mammal with an immunogen comprising a compound-trimer complex of a trimeric TNF superfamily member and a compound disclosed herein; obtaining an antibody preparation from said mammal; deriving therefrom monoclonal antibodies that selectively recognise said complex and screening the population of monoclonal antibodies for monoclonal antibodies that bind to the TNF superfamily member only in the presence of the compound.

The antibody molecules of the present invention may comprise a complete antibody molecule having full length heavy and light chains or a fragment or antigen-binding portion thereof. The term "antigen-binding portion" of an antibody refers to one or more fragments of an antibody that retain the ability to selectively bind to an antigen. It has been shown that the antigen-binding function of an antibody can be performed by fragments of a full-length antibody. The antibodies and fragments and antigen binding portions thereof may be, but are not limited to Fab, modified Fab, Fab', modified Fab', F(ab')$_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9): 1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO 2005/003169, WO 2005/003170 and WO 2005/003171 and Fab-dAb fragments described in International patent application WO2009/040562. Multi-valent antibodies may comprise multiple specificities or may be monospecific (see for example WO 92/22853 and WO 05/113605). These antibody fragments may be obtained using conventional techniques known to those of skill in the art, and the fragments may be screened for utility in the same manner as intact antibodies.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

An antibody of the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma that includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to CDR-grafted antibody molecules in which CDR sequences derived from the germline of another mammalian species, such as a mouse, have been grafted onto human framework sequences. Additional framework region modifications may be made within the human framework sequences.

As used herein, the term 'CDR-grafted antibody molecule' refers to an antibody molecule wherein the heavy and/or light chain contains one or more CDRs (including, if desired, one or more modified CDRs) from a donor antibody (e.g. a murine or rat monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the CDR-grafted antibody according to the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available for example at: http://www.vbase2.org/ (see Retter et al, Nucl. Acids Res. (2005) 33 (supplement 1), D671-D674).

In a CDR-grafted antibody of the present invention, the acceptor heavy and light chains do not necessarily need to be derived from the same antibody and may, if desired, comprise composite chains having framework regions derived from different chains.

Also, in a CDR-grafted antibody of the present invention, the framework regions need not have exactly the same sequence as those of the acceptor antibody. For instance, unusual residues may be changed to more frequently occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995).

In one embodiment the antibody heavy chain comprises a CH1 domain and the antibody light chain comprises a CL domain, either kappa or lambda.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or surface carries no net electrical charge. In one embodiment the antibody or fragment according to the present disclosure has an isoelectric point (pI) of at least 7. In one embodiment the antibody or fragment has an isoelectric point of at least 8, such as 8.5, 8.6, 8.7, 8.8 or 9. In one embodiment the pI of the antibody is 8. Programs such as ** ExPASY http://www.expasy.ch/tools/pi_tool.html (see Walker, The Proteomics Protocols Handbook, Humana Press (2005), 571-607), may be used to predict the isoelectric point of the antibody or fragment.

The antibody of the invention may comprise at least one, at least two or all three heavy chain CDR sequences of SEQ ID NOS: 4 to 6 (HCDR1/HCDR2/HCDR3 respectively). These are the HCDR1/HCDR2/HCDR3 sequences of the CA185_01974 antibody of the Examples.

Furthermore, the antibody of the invention may comprise at least one, at least two or all three light chain CDR sequences of SEQ ID NOS: 1 to 3 (LCDR1/LCDR2/LCDR3 respectively). These are the LCDR1/LCDR2/LCDR3 sequences of the CA185_01974 antibody of the Examples.

The antibody of the invention suitably comprises at least a HCDR3 sequence of SEQ ID NO: 6.

Typically, the antibody of the invention comprises at least one heavy chain CDR sequence selected from SEQ ID NOS: 4 to 6 and at least one light chain CDR sequence selected from SEQ ID NOS 1 to 3. The antibody of the invention may comprise at least two heavy chain CDR sequences selected from SEQ ID NOS: 4 to 6 and at least two light chain CDR sequences selected from SEQ ID NOS: 1 to 3. The antibody of the invention typically comprises all three heavy chain CDR sequences of SEQ ID NOS: 4 to 6 (HCDR1/HCDR2/HCDR3 respectively) and all three light chain CDR sequences SEQ ID NOS: 1 to 3 (LCDR1/LCDR2/LCDR3 respectively). The antibodies may be chimeric, human or humanised antibodies.

The antibody of the invention may also comprise at least one, at least two or all three heavy chain CDR sequences of SEQ ID NOS: 19 to 21 (HCDR1/HCDR2/HCDR3 respectively). These are the HCDR1/HCDR2/HCDR3 sequences of the CA185_01979 antibody of the Examples.

The antibody typically comprises a HCDR3 sequence of SEQ ID NO: 21.

The antibody of the invention may also comprise at least one, at least two or all three light chain CDR sequences of SEQ ID NOS: 1, 17, 18 (LCDR1/LCDR2/LCDR3 respectively). These are the LCDR1/LCDR2/LCDR3 sequences of the CA185_01979 antibody of the Examples Typically, the antibody of the invention comprises at least one heavy chain CDR sequence selected from SEQ ID NOS: 19 to 21 and at least one light chain CDR sequence selected from SEQ ID NOS: 1, 17, 18. The antibody of the invention may comprise at least two heavy chain CDR sequences selected from SEQ ID NOS: 19 to 21 and at least two light chain CDR sequences selected from SEQ ID NOS: 1, 17, 18.

The antibody of the invention typically comprises all three heavy chain CDR sequences of SEQ ID NOS: 19 to 21 (HCDR1/HCDR2/HCDR3 respectively) and all three light chain CDR sequences SEQ ID NOS: 1, 17, 18 (LCDR1/LCDR2/LCDR3 respectively). The antibodies may be chimeric, human or humanised antibodies.

The antibody of the invention may comprise any combination of CDR sequences of the CA185_01974 antibody and the CA185_01979 antibody. In particular, the antibody of the invention may comprise least one HCDR sequence selected from SEQ ID NOs: 4-6 and 19-21 and/or at least one LCDR sequence selected from SEQ ID NOs: 1-3, 17 and 18.

The antibody may comprise:
a HCDR1 selected from SEQ ID NOs: 4 and 19; and/or
a HCDR2 selected from SEQ ID NOs: 5 and 20; and/or
a HCDR3 selected from SEQ ID NOs: 6 and 21; and/or
a LCDR1 of SEQ ID NO: 1; and/or
a LCDR2 selected from SEQ ID NOs: 2 and 17; and/or
a LCDR3 selected from SEQ ID NOs: 3 and 18.

The antibody of the invention may comprise a heavy chain variable region (HCVR) sequence of SEQ ID NO: 8 (the HCVR of CA185_01974). The antibody of the invention may comprise a light chain variable region (LCVR) sequence of SEQ ID NO: 7 (the LCVR of CA185_01974). The antibody of the invention suitably comprises the heavy chain variable region sequence of SEQ ID NO: 8 and the light chain variable region sequence of SEQ ID NO: 7.

The antibody of the invention may also comprise a heavy chain variable region (HCVR) sequence of SEQ ID NO: 23 (the HCVR of CA185_01979). The antibody of the invention may comprise a light chain variable region (LCVR) sequence of SEQ ID NO: 22 (the LCVR of CA185_01979). The antibody of the invention suitably comprises the heavy chain variable region sequence of SEQ ID NO: 23 and the light chain variable region sequence of SEQ ID NO: 22.

Again, the antibody of the invention may comprise a combination of heavy and light chain variable regions from the CA185_01974 and CA185_01979 antibodies. In other words, the antibody of the invention may comprise a heavy chain variable region of SEQ ID NO: 8 or 23 and/or a light chain variable region of SEQ ID NO: 7 or 22.

The antibody of the invention may comprise a heavy chain (H-chain) sequence of SEQ ID NO: 12 (CA185_01974 mIgG1) or 13 (CA185_01974 mFab (no hinge)). The antibody of the invention may comprise a light chain (L-chain) sequence of SEQ ID NO: 11 (CA185_01974 kappa light chain). The antibody of the invention typically comprises the heavy chain sequence of SEQ ID NO: 12/13 and the light chain sequence of SEQ ID NO: 11. The antibodies may be chimeric, human or humanised antibodies.

The antibody of the invention may comprise a heavy chain sequence of SEQ ID NO: 27 (CA185_01979 mIgG1) or 28 (CA185_01979 mFab (no hinge)). The antibody of the invention may comprise a light chain sequence of SEQ ID NO: 26 (CA185_01979 kappa light chain). Generally, the antibody of the invention comprises the heavy chain sequence of SEQ ID NO: 27/28 and the light chain sequence of SEQ ID NO: 26. The antibodies may be chimeric, human or humanised antibodies. Again, sequences from CA185_01974 and CA185_01979 may be combined.

The antibody may alternatively be or may comprise a variant of one of the specific sequences recited above. For example, a variant may be a substitution, deletion or addition variant of any of the above amino acid sequences.

A variant antibody may comprise 1, 2, 3, 4, 5, up to 10, up to 20 or more (typically up to a maximum of 50) amino acid substitutions and/or deletions from the specific sequences discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants typically involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

"Derivatives" or "variants" generally include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Variant antibodies may have an amino acid sequence which has more than about 60%, or more than about 70%, e.g. 75 or 80%, preferably more than about 85%, e.g. more than about 90 or 95% amino acid identity to the amino acid sequences disclosed herein (particularly the HCVR/LCVR sequences and the H- and L-chain sequences). Furthermore, the antibody may be a variant which has more than about 60%, or more than about 70%, e.g. about 75 or 80%, typically more than about 85%, e.g. more than about 90 or 95% amino acid identity to the HCVR/LCVR sequences and the H- and L-chain sequences disclosed herein, whilst retaining the exact CDRs disclosed for these sequences. Variants may retain at least about 90%, 91%, 92%, 93%, 94%, 95%, 96%, 97%, 98% or 99% identity to the HCVR/LCVR sequences and to the H- and L-chain sequences disclosed herein (in some circumstances whilst retaining the exact CDRs).

Variants typically retain about 60%-about 99% identity, about 80%-about 99% identity, about 90%-about 99% identity or about 95%-about 99% identity. This level of amino acid identity may be seen across the full length of the relevant SEQ ID NO sequence or over a part of the sequence, such as across about 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

The present invention thus provides antibodies having specific sequences and variants which maintain the function or activity of these chains.

The present invention also provides an isolated DNA sequence encoding the heavy and/or light chain variable regions(s) of an antibody molecule of the present invention. Thus, the present invention provides an isolated DNA sequence of SEQ ID NO: 10, which encodes the heavy chain variable region of SEQ ID NO: 8. The invention also provides an isolated DNA sequence of SEQ ID NO: 9, which encodes the light chain variable region of SEQ ID NO: 7.

The present invention also provides an isolated DNA sequence of SEQ ID NO: 25, which encodes the heavy chain variable region of SEQ ID NO: 23. The invention also provides an isolated DNA sequence of SEQ ID NO: 24, which encodes the light chain variable region of SEQ ID NO: 22.

The present invention also provides an isolated DNA sequence encoding the heavy and/or light chain(s) of an antibody molecule of the present invention. Suitably, the DNA sequence encodes the heavy or the light chain of an antibody molecule of the present invention. Thus, the present invention provides an isolated DNA sequence of SEQ ID NO: 15 or 16, which encode the heavy chains of SEQ ID NOs: 12 and 13 respectively. The invention also provides an isolated DNA sequence of SEQ ID NO: 14, which encodes the light chain of SEQ ID NO: 11.

The present invention also provides an isolated DNA sequence of SEQ ID NO: 30 or 31, which encode the heavy chains of SEQ ID NOs: 27 and 28 respectively. The invention also provides an isolated DNA sequence of SEQ ID NO: 29, which encodes the light chain of SEQ ID NO: 26.

A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing. Generally, a variant has 1-20, 1-50, 1-75 or 1-100 substitutions and/or deletions.

Suitable variants may be at least about 70% homologous to a polynucleotide of any one of nucleic acid sequences disclosed herein, typically at least about 80 or 90% and more suitably at least about 95%, 97% or 99% homologous thereto. Variants may retain at least about 90%, 91%, 92%, 93%, 94%, 95%, 96%, 97%, 98% or 99% identity. Variants typically retain about 60%-about 99% identity, about 80%-about 99% identity, about 90%-about 99% identity or about 95%-about 99% identity. Homology and identity at these levels is generally present at least with respect to the coding regions of the polynucleotides. Methods of measuring homology are well known in the art and it will be understood by those of skill in the art that in the present context, homology is calculated on the basis of nucleic acid identity. Such homology may exist over a region of at least about 15, at least about 30, for instance at least about 40, 60, 100, 200 or more contiguous nucleotides (depending on the length). Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, typically less than about 0.1, suitably less than about 0.01, and most suitably less than about 0.001. For example, the smallest sum probability may be in the range of about 1-about 0.001, often about 0.01-about 0.001.

The homologue may differ from a sequence in the relevant polynucleotide by less than about 3, 5, 10, 15, 20 or more mutations (each of which may be a substitution, deletion or insertion). For example, the homologue may differ by 3-50 mutations, often 3-20 mutations. These mutations may be measured over a region of at least 30, for instance at least about 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

Screening methods as described herein may be used to identify suitable antibodies that are capable of binding to a compound-trimer complex. Thus, the screening methods described herein may be carried out to test antibodies of interest.

Antibodies of the invention can be tested for binding to a compound-trimer complex by, for example, standard ELISA or Western blotting. An ELISA assay can also be used to screen for hybridomas that show positive reactivity with the target protein. The binding selectivity of an antibody may also be determined by monitoring binding of the antibody to cells expressing the target protein, for example by flow cytometry. Thus, a screening method of the invention may comprise the step of identifying an antibody that is capable of binding a compound-trimer complex by carrying out an ELISA or Western blot or by flow cytometry.

Antibodies of the invention selectively (or specifically) recognise at least one compound-trimer complex, i.e. epitopes within a compound-trimer complex. An antibody, or other compound, "selectively binds" or "selectively recognises" a protein when it binds with preferential or high affinity to the protein for which it is selective but does not substantially bind, or binds with low affinity, to other proteins. The selectivity of an antibody of the invention for a target a compound-trimer complex may be further studied by determining whether or not the antibody binds to other related compound-trimer complexes as discussed above or whether it discriminates between them.

An antibody of the invention may bind specifically (or selectively) to compound-trimer complexes comprising the trimeric forms of one or more TNF superfamily members. For example, an antibody may bind to compound-trimer complexes comprising TNFα, compound-trimer complexes comprising TNFβ and compound-trimer complexes comprising CD40L. Alternatively, an antibody may bind specifically (or selectively) to compound-trimer complexes comprising only one of the TNF superfamily members, but not to compound-trimer complexes comprising any other TNF superfamily members. For example, an antibody may bind to compound-trimer complexes comprising TNFα, but not to compound-trimer complexes comprising TNFβ or compound-trimer complexes comprising CD40L. An antibody may bind specifically (or selectively) to compound-trimer complexes comprising up to two, three, four or up to all of the TNF superfamily members.

By specific (or selective), it will be understood that the antibody binds to the compound-trimer complexes of interest with no significant cross-reactivity to any other molecule, which may include test compounds in the absence of a TNF superfamily trimer or TNF superfamily member trimers in the absence of a test compound. Cross-reactivity may be assessed by any suitable method described herein. Cross-reactivity of an antibody for a compound-trimer complex with a molecule other than the compound-trimer complex may be considered significant if the antibody binds to the other molecule at least about 5%, 10%, 15%, 20%, 25%, 30%, 35%, 40%, 45%, 50%, 55%, 60%, 65%, 70%, 75%, 80%, 85%, 90% or 100% as strongly as it binds to the compound-trimer complex of interest. An antibody that is specific (or selective) for the compound-trimer complex may bind to another molecule at less than about 90%, 85%, 80%, 75%, 70%, 65%, 60%, 55%, 50%, 45%, 40%, 35%, 30%, 25% or 20% the strength that it binds to the compound-trimer complex. The antibody may bind to the other molecule at less than about 20%, less than about 15%, less than about 10% or less than about 5%, less than about 2% or less than about 1% the strength that it binds to the compound-trimer complex. The antibody specifically (or selectively) binds to a compound-trimer complex compared with (i) the trimeric form of the TNF superfamily member in the absence of the compound and/or (ii) the compound in the absence of the TNF superfamily member trimer.

The rates at which an antibody binds to a compound-trimer complex is referred to herein as the "on" rate" $k_{on-ab}$ and the rate at which the antibody dissociates from the compound-trimer complex is referred to herein as the "off" rate or $k_{off-ab}$. As used herein, the symbol "$K_{D-ab}$" denotes the binding affinity (dissociation constant) of an antibody for a compound-trimer complex. $K_{D-ab}$ is defined as $k_{off-ab}/k_{on-ab}$. Antibodies may have slow "on" rates, which can be measured in minutes by mass spectral analysis of the compound-trimer complex and antibody peak intensities. $K_{D-ab}$ values for an antibody can be estimated by repeating this measurement at different antibody: compound-trimer complex ratios.

The $K_{D-ab}$ value of the antibody for binding to a compound-trimer complex may be at least about 1.5 times, 2 times, 3 times, 4 times, 5 times, 10 times, 20 times, 30 times, 40 times, 50 times, 60 times, 70 times, 80 times, 90 times, 100 times, 200 times, 300 times or 400 times lower, or lower, than the $K_{D-ab}$ value of the antibody for binding to the trimeric TNF superfamily member in the absence of the compound and/or the $K_{D-ab}$ value of the antibody for binding to the compound in the absence of the trimeric TNF superfamily member. The $K_{D-ab}$ value of the antibody for binding to a compound-trimer complex may be decreased at least about 10 times, at least about 100 times, at least about 200 times, at least about 300 times the $K_{D-ab}$ value of the TNF superfamily trimer binding to the TNF superfamily receptor in the absence of the test compound, i.e. the binding affinity of the antibody for the compound-trimer complex is typically increased at least about 10-fold, suitably at least about 100-fold, more suitably at least about 200-fold, most suitably at least about 300-fold compared to the binding affinity of the antibody to the trimeric TNF superfamily member in the absence of the compound and/or the binding affinity of the antibody to the compound in the absence of the trimeric TNF superfamily member.

The binding affinity may be given in terms of binding affinities ($K_{D-ab}$) and may be given in any appropriate units, such as µM, nM or pM. The smaller the $K_{D-ab}$ value, the larger the binding affinity of the antibody to the compound-trimer complex.

The $K_{D-ab}$ value of the antibody for binding to the compound-trimer complex may be at least about 1.5 times, 2 times, 3 times, 4 times, 5 times, 10 times, 20 times, 30 times, 40 times, 50 times, 60 times, 70 times, 80 times, 90 times, 100 times lower, or even lower than the $K_{D-ab}$ value of the antibody for binding to the trimeric TNF superfamily member in the absence of the compound and/or the $K_{D-ab}$ value of the antibody for binding to the compound in the absence of the trimeric TNF superfamily member.

The decrease in the $K_{D-ab}$ value of the antibody for binding to the compound-trimer complex compared to the $K_{D-ab}$ value of the antibody binding to the trimeric TNF superfamily member in the absence of the compound and/or the $K_{D-ab}$ value of the antibody for binding to the compound in the absence of the trimeric TNF superfamily member may result from an increase in the on rate ($k_{on-ab}$) of the antibody binding to the compound-trimer complex compared to the antibody binding to the trimeric TNF superfamily member in the absence of the compound and/or the antibody binding to the compound in the absence of the trimeric TNF superfamily member; and/or a decrease in the off rate ($k_{off-ab}$) compared to the antibody binding to the trimeric TNF superfamily member in the absence of the compound and/or the antibody binding to the compound in the absence of the trimeric TNF superfamily member.

The on rate ($k_{on-ab}$) of the antibody binding to the compound-trimer complex is generally increased compared to the on rate of the antibody binding to the trimeric TNF superfamily member in the absence of the compound and/or the antibody binding to the compound in the absence of the trimeric TNF superfamily member. The off rate ($k_{off-ab}$) of the antibody binding to the compound-trimer complex is generally decreased compared to the off rate of the antibody binding to the trimeric TNF superfamily member in the absence of the compound and/or the antibody binding to the compound in the absence of the trimeric TNF superfamily member. Most typically, the on rate ($k_{on-ab}$) of the antibody binding to the compound-trimer complex is increased, and the off-rate ($k_{off-ab}$) of the antibody binding to the compound-trimer complex is decreased, compared to the antibody binding to the trimeric TNF superfamily member in the absence of the compound and/or the antibody binding to the compound in the absence of the trimeric TNF superfamily member.

The $k_{on-ab}$ value of the antibody binding to the compound-trimer complex may be increased by at least about 1.5-fold or at least two-fold and typically at least about three fold compared to the $k_{on-ab}$ value of the antibody binding to the trimeric TNF superfamily member in the absence of the compound and/or the antibody binding to the compound in the absence of the trimeric TNF superfamily member and/or the $k_{off-ab}$ value of the antibody binding to the compound-trimer complex may be decreased by at least about two-fold, at least about 10-fold, at least about 20-fold, at least about 30-fold, at least about 40-fold, at least about 50-fold, at least about 60-fold, at least about 70-fold, at least about 80-fold more suitably at least about 90-fold compared to the $k_{off-ab}$ value of the antibody binding to the trimeric TNF superfamily member in the absence of the compound and/or the antibody binding to the compound in the absence of the trimeric TNF superfamily member.

The $k_{on-ab}$, $k_{off-ab}$, and $K_{D-ab}$ values may be determined using any appropriate technique, for example surface plasmon resonance, mass spectrometry and isothermal calorimetry.

The $K_{D-ab}$ value of the antibody binding to a compound-trimer complex may be 1 nM, 900 pM, 700 pM, 500 pM, 100 pM, 10 pM or less (typically down to about 1 pM). Antibodies of the invention will desirably bind to the compound-trimer complexes of the invention with high affinity, for example in the picomolar range. The $K_{D-ab}$ value of the antibody binding to a compound-trimer complex may be 1 nM or less, 900 pM or less, 700 pM or less, 500 pM or less, 400 pM or less, 300 pM or less, 200 pM or less, 100 pM or less, 90 pM or less, 80 pM or less, 70 pM or less, 60 pM or less, 50 pM or less, 40 pM or less, 30 pM or less, 20 pM or less, 10 pM or less (again, down to about 1 pM).

Once a suitable antibody has been identified and selected, the amino acid sequence of the antibody may be identified by methods known in the art. The genes encoding the antibody can be cloned using degenerate primers. The antibody may be recombinantly produced by routine methods.

Antibodies of the invention may compete for binding to TNFα with, or bind to the same epitope as, those defined above in terms of H-chain/L-chain, HCVR/LCVR or CDR sequences. In particular, an antibody may compete for binding to TNFα with, or bind to the same epitope as, an antibody which comprises a HCDR1/HCDR2/HCDR3/LCDR1/LCDR2/LCDR3 sequence combination of SEQ ID NOs: 4/5/6/1/2/3 or SEQ ID NOs: 19/20/21/1/17/18. An antibody may compete for binding to TNFα with, or bind to the same epitope as, an antibody which comprises a HCVR and LCVR sequence pair of SEQ ID NOs: 8/7 or SEQ ID NOs: 23/22.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

One can easily determine whether an antibody binds to the same epitope as, or competes for binding with, a reference antibody by using routine methods known in the art. For example, to determine if a test antibody binds to the same epitope as a reference antibody of the invention, the reference antibody is allowed to bind to a protein or peptide under saturating conditions. Next, the ability of a test antibody to bind to the protein or peptide is assessed. If the test antibody is able to bind to the protein or peptide following saturation binding with the reference antibody, it can be concluded that the test antibody binds to a different epitope than the reference antibody. On the other hand, if the test antibody is not able to bind to protein or peptide following saturation binding with the reference antibody, then the test antibody may bind to the same epitope as the epitope bound by the reference antibody of the invention.

To determine if an antibody competes for binding with a reference antibody, the above-described binding methodology is performed in two orientations. In a first orientation, the reference antibody is allowed to bind to a protein/peptide under saturating conditions followed by assessment of binding of the test antibody to the protein/peptide molecule. In a second orientation, the test antibody is allowed to bind to the protein/peptide under saturating conditions followed by assessment of binding of the reference antibody to the protein/peptide. If, in both orientations, only the first (saturating) antibody is capable of binding to the protein/peptide, then it is concluded that the test antibody and the reference antibody compete for binding to the protein/peptide. As will be appreciated by the skilled person, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50%, 75%, 90% or even 99% as measured in a competitive binding assay (see, e.g., Junghans et al., Cancer Res, 1990: 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

The antibodies of the invention may be used to identify compounds of the invention as described herein. The antibodies of the invention may also be used as target engagement biomarkers. A target engagement biomarker can be used to detect the engagement, i.e. the binding of a ligand to a target of interest. In the present case, the antibodies of the invention only bind to the complexes of compounds of the invention with trimeric forms of TNF superfamily members. Therefore, if an antibody of the invention is able to bind to a compound-trimer complex, this is evidence that the ligand (compound) has bound to the target of interest (TNF superfamily member trimer). Antibodies of the invention can be modified to add a detectable marker as described herein. Therefore, engagement of a compound of the invention with a target TNF superfamily member may be detected using such an antibody.

The use of antibodies of the invention as target engagement biomarkers is potentially useful in a clinical or pre-clinical environment, where a sample may be taken from a subject being treated according to the present invention. The sample obtained from the subject may be treated with an antibody of the invention in order to determine whether the compound used to treat the subject has bound to the target TNF superfamily member. The sample obtained from the subject may be any appropriate tissue or fluid, such as blood, plasma or urine. The subject may be mammalian, typically human.

Accordingly, the invention provides the use of an antibody of the invention as a target engagement biomarker for the detection of a compound-trimer complex comprising a trimeric protein that is a TNF superfamily member and a compound that is capable of binding to a trimeric protein that is a TNF superfamily member, whereby the compound-trimer complex binds to the requisite TNF superfamily receptor and modulates the signalling induced by the trimer through the receptor in a sample obtained from a subject. The superfamily member is suitably TNFα and/or the modulation is antagonism of TNFR1 signalling.

Similarly, the present invention provides a method of detecting target engagement of a compound to a trimeric TNF superfamily member, whereby the compound-trimer complex binds to the requisite receptor and modulates the signalling induced by the trimer through the receptor, said method comprising:

(a) obtaining a sample from a subject administered said compound;

(b) contacting an antibody of the invention to said sample and a control sample, wherein said antibody is detectable;

(c) determining the amount of binding of said detectable antibody to said sample and said control sample, wherein binding of said detectable antibody to said sample greater than binding of said detectable antibody to said control sample indicates target engagement of said compound to said trimeric TNF superfamily member.

Methods of detecting antibodies, and measuring the amount of binding of an antibody to a target, are well known in the art. Typically, antibodies can be labelled. Such labels include enzymes, biotin/streptavidin, fluorescent proteins and fluorescent dyes.

Binding of an antibody to a target may be measured, for example, by an immunoassay method. Immunoassays include Western Blotting, ELISA, immunofluorescence, immunohistochemistry and flow cytometry. Any appropriate technique may be used to measure binding of the antibody to the TNF superfamily member.

In the method described above, binding of the detectable antibody to the sample from a subject who has been administered the compound is compared with binding of the antibody to a control sample. The control sample may be any appropriate sample. The control sample is typically a "negative control" which is representative of binding of the antibody to the TNF superfamily member in the absence of the compound. For example, the sample may be obtained from the patient prior to administration of the compound. The control may also be based on previously determined measurements e.g. from a number of samples from different subjects in the absence of compound. Measurements from about 5, 10, 20, 50 or 100 subjects may be used in determining the control value. The control may be an average value, or a range of all the values obtained.

The experimental conditions e.g. methods of detection are the same for the sample from a subject administered the compound, and for the control sample. The antibody is also the same in both cases.

Greater binding (increased binding) of the detectable antibody to the sample from the patient administered the compound compared with binding of the antibody to the control sample is indicative of target engagement of the compound to the trimeic TNF superfamily member. In other words, equivalent or lower binding (decreased binding) for the sample from the patient administered the compound relative to the control indicates that there is no target engagement of said compound. In other words, no significant difference in the two amounts indicates that there is no target engagement.

The skilled person can readily determine when there is increased binding relative to the control. For example when the control is a range of data, target engagement may be determined based on the spread of the data, the difference between the control data and the detected binding of the antibody in the sample in question, and calculated confidence levels. It is also possible to identify target engagement when the detected binding for the sample in question is higher than the maximum amount of binding detected in any negative control.

Target engagement may be detected if binding of the antibody is increased by about 30% or more relative to the highest amount in the control range. Target engagement may also be detected if binding of the antibody is increased by about 40% or more, or about 50% or more relative to the control range. The same applies when the control is an average value, or a single value based on a sample from the patient prior to administration of the compound. There is of course no upper limit to the percentage increase relative to the control.

An antibody of the invention may be used to screen for a compound that elicits a conformational change in a trimeric TNF superfamily member, wherein said conformational change modulates the signalling of the requisite TNF superfamily receptor on binding of the trimeric TNF superfamily member. The superfamily member is typically TNFα and/or the modulation is antagonism of TNFR1 signalling.

The antibodies of the present invention may be used in the treatment and/or prophylaxis of a pathological condition. Accordingly, provided is an antibody of the invention for use in a method of therapy practiced on the human or animal body. The invention also provides a method of therapy comprising the administration of an antibody of the invention to a subject. The antibody of the invention may be used in any therapeutic indication and/or pharmaceutical composition described herein.

Antibody Assays

As described herein, the present invention provides antibodies that selectively bind to at least one compound-trimer complex described herein relative to their binding to the compound alone or to the TNF superfamily member in the absence of the compound. These antibodies may be used to identify further compounds or classes of compounds having the same properties.

Monoclonal antibodies may be generated against a TNF superfamily member using the standard techniques described herein. These anti-TNF superfamily member antibodies can then be screened for antibodies that bind to compound-trimer complexes of the invention, or for monoclonal antibodies for which binding to the TNF superfamily member is inhibited by compounds as described herein.

Alternatively, monoclonal antibodies can be generated against particular TNF superfamily member trimer-compound complexes. These antibodies can then be screened for monoclonal antibodies that selectively bind to the TNF superfamily member in the presence of the compound relative to their binding to the TNF superfamily member in the absence of the compound.

Once an antibody that selectively binds to at least one compound-trimer complex of the invention relative to its binding to the compound alone or to the TNF superfamily member in the absence of the compound has been generated, it can be used to screen for other compounds possessing the same activity as the test compounds.

Accordingly, the invention provides an assay for identifying a compound of the invention comprising the steps of:
a) performing a binding assay to measure the binding affinity of a test compound-trimer complex to an antibody of the invention;
b) comparing the binding affinity as measured in step (a) with the binding affinity of a different compound-trimer complex known to bind with high affinity to the antibody referred to in step (a); and
c) selecting the compound present in the compound-trimer complex of step (a) if its measured binding affinity is acceptable when considered in the light of the comparison referred to in step (b).

As will be appreciated, the "different" compound-trimer complex referred to in step (b) above will generally be a complex containing the same trimer as the compound-trimer complex of step (a), but a different compound. The compound may be any of compounds (1)-(6).

By "acceptable" in step (c) is meant that the binding affinity of the compound-trimer complex referred to in step (a) and the binding affinity of the different compound-trimer complex referred to in step (b) are approximately comparable. Selective binding of said antibody to said complex is typically measured relative to the binding of said antibody to the TNF superfamily member in the absence of the compound or to the compound in the absence of the TNF superfamily member.

The binding affinity of the compound-trimer complex referred to in step (a) will generally be superior to the binding affinity of the different compound-trimer complex referred to in step (b). Suitably, the difference in the binding affinity of the compound-trimer complex referred to in step (a) relative to the binding affinity of the different compound-trimer complex referred to in step (b) will be within limits of 10-fold, 20-fold, 50-fold, 100-fold, 200-fold or 500-fold.

Libraries of compounds can be assayed using the antibodies of the invention. The library compounds can be incubated with said antibody in the presence and absence of a TNF superfamily member. A compound that forms part of a compound-trimer complex that binds to an antibody of the invention only in the presence of both the TNF superfamily member and the compound is a likely candidate to have the same activity as the compounds described herein. The assays disclosed herein may then be used to verify whether the test compound is a compound as described herein.

One or more of the antibodies of the invention may be used in the assay. A generic antibody that is capable of binding to complexes of any compound of the invention with a particular TNF superfamily member may be used in the antibody assay of the invention.

A panel of multiple antibodies of the present invention that are specific for different compound-trimer complexes may be used in the antibody assay of the invention. The panel of antibodies may include at least 5, at least 10, at least 15, at least 20, at least 30, at least 40 or at least 50 antibodies (for example up to 75 antibodies).

The antibody assay of the present invention may be a high throughput assay that is capable of screening a large number of test compounds over a short space of time to identify compounds of the present invention.

The TNF superfamily members and their receptors may be purified or present in mixtures, such as in cultured cells, tissue samples, body fluids or culture medium. Assays may be developed that are qualitative or quantitative, with the latter being useful for determining the binding parameters (affinity constants and kinetics) of the test compound to trimeric forms of TNF superfamily members, and also of the binding parameters of the compound-trimer complex to the requisite TNF receptor.

The sample comprising the TNF superfamily member and the compound may further comprise a destabilising agent. Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent may be DMSO, typically at a concentration of 5%, 10% or higher.

The test compounds may have any/all of the properties discussed above.

TNF Superfamily and their Receptors

There are 22 TNF superfamily members currently known: TNFα (TNFSF1A), TNFβ (TNFSF1B), CD40L (TNFSF5), BAFF (TNFSF13B/BlyS), APRIL (TNFSF13), OX40L (TNFSF4), RANKL (TNFSF11/TRANCE), TWEAK (TNFSF12), TRAIL (TNFSF10), TL1A (TNFSF15), LIGHT (TNFSF14), Lymphotoxin, Lymphotoxin β (TNFSF3), 4-1BBL (TNFSF9), CD27L (TNFSF7), CD30L (TNFSF8), EDA (Ectodysplasin), EDA-A1 (Ectodysplasin A1), EDA-A2 (Ectodysplasin A2), FASL (TNFSF6), NGF and GITRL (TNFSF18).

The TNF superfamily member is typically TNFα. TNFα exists in both a soluble ($TNF\alpha_s$) and membrane-bound form ($TNF\alpha_m$). When TNFα is referred to herein this encompasses both the $TNF\alpha_s$ and $TNF\alpha_m$ forms. TNFα is most suitably in the $TNF\alpha_s$ form. The $TNF\alpha_s$ may comprise the sequence of SEQ ID NO: 35 or SEQ ID NO: 36, or a variant thereof (as described above).

The assays of the invention may be used to identify modulators of at least one of any TNF superfamily members, including the 22 known TNF superfamily members. Specifically, the assays of the invention may be used to identify compounds that bind to any TNF superfamily member, particularly to trimeric forms of TNF superfamily members, and that stabilise these trimers in a conformation that is capable of binding to the requisite TNF receptor, and which modulate signalling through said receptor. The assay of the invention is, in particular, used to identify modulators of TNFα or CD40L, especially TNFα, or even $TNF\alpha_s$.

The compound described herein may be a modulator of at least one of any TNF superfamily members, including the 22 known TNF superfamily members. In particular, the TNF superfamily member is TNFα or CD40L, especially TNFα or even $TNF\alpha_s$.

The compound-trimer complex of the invention may include the trimeric form of any TNF superfamily member, including the 22 known TNF superfamily members. The TNF superfamily member is typically TNFα or CD40L. The TNF superfamily member may be TNFα, most suitably $TNF\alpha_s$.

Members of the TNF superfamily bind to, and initiate signalling through TNF receptors. There are currently 34 known TNF receptors: 4-1BB (TNFRSF9/CD137), NGF R (TNFRSF16), BAFF R (TNFRSF13C), Osteoprotegerin (TNFRSF11B), BCMA (TNFRSF17), OX40 (TNFRSF4), CD27 (TNFRSF7), RANK (TNFRSF11A), CD30 (TNFRSF8), RELT (TNFRSF19L), CD40 (TNFRSF5), TACI (TNFRSF13B), DcR3 (TNFRSF6B), TNFRH3 (TNFRSF26), DcTRAIL R1 (TNFRSF23), DcTRAIL R2 (TNFRSF22), TNF-R1 (TNFRSF1A), TNF-R2 (TNFRSF1B), DR3 (TNFRSF25), TRAIL R1 (TNFRSF10A), DR6 (TNFRSF21), TRAIL R2 (TNFRSF10B), EDAR, TRAIL R3 (TNFRSF10C), Fas (TNFRSF6/CD95), TRAIL R4 (TNFRSF10D), GITR (TNFRSF18), TROY (TNFRSF19), HVEM (TNFRSF14), TWEAK R (TNFRSF12A), TRAMP (TNFRSF25), Lymphotoxin β R (TNFRSF3) and XEDAR.

The TNF receptor is suitably TNF-R1 (TNFR1) or TNF-R2 (TNFR2). When TNF-R is referred to herein this encompasses both TNF-R1 and TNF-R2, including the extracellular domain (ECD) of TNF-R1 and TNF-R2. The assays of the invention may be used to identify compounds that modulate the signalling of TNF superfamily members through any requisite TNF superfamily receptor. The assays of the invention may be used to identify compounds that modulate the signalling of TNF superfamily members through TNF-R1, TNF-R2 or CD40. The TNF superfamily member may be TNFα and the TNF receptor may be TNF-R1 or TNF-R2. In particular, the TNF superfamily member may be TNFα and the TNF receptor may be TNF-R1. More particularly, the TNF superfamily member may be $TNF\alpha_s$ and the TNF receptor may be TNF-R1. The assays of the invention may be used to identify compounds which act by specifically modulate the signalling of TNF superfamily members through TNF-R1. In particular, the compounds may act by modulating the signalling of TNF superfamily members through TNF-R1, but have no effect on signalling of TNF superfamily members through TNF-R2.

The compound-trimer complex of the invention may modulate TNF superfamily members signalling through at least one TNF receptor, including the 34 known TNF receptors. The TNF receptor is typically TNF-R1, TNF-R2 or CD40L.

In particular, the TNF superfamily member is TNFα and the TNF receptor is TNF-R1 or TNF-R2. The TNF superfamily member is more suitably TNFα and the TNF receptor is TNF-R1. Most suitably, the TNF superfamily member is $TNF\alpha_s$ and the TNF receptor is TNF-R1.

Therapeutic Indications

TNFα is the archetypal member of the TNF superfamily. TNFα is a pleiotropic cytokine that mediates immune regulation and inflammatory responses. In vivo, TNFα is also known to be involved in responses to bacterial, parasitic and viral infections. In particular, TNFα is known to have a role in rheumatoid arthritis (RA), inflammatory bowel diseases (including Crohn's disease), psoriasis, Alzheimer's disease (AD), Parkinson's disease (PD), pain, epilepsy, osteoporosis, asthma, sepsis, fever, Systemic lupus erythematosus (SLE) and Multiple Sclerosis (MS) and cancer. TNFα is also known to have a role in Amyotrophic Lateral Sclerosis (ALS), ischemic stroke, immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AKI), obstructive uropathy, kidney allograft rejection, cisplatin-induced AKI and obstructive uropathy.

Other members of the TNF superfamily are known to be involved in autoimmune disease and immune deficiencies. In particular, members of the TNF superfamily are known to be involved in RA, SLE, cancer, MS, asthma, rhinitis, osteoporosis and multiple myeloma (MM). TL1A is known to play a role in organ transplant rejection.

A compound described herein may be used to treat, prevent or ameliorate any condition that that can be treated, prevented or ameliorated by a conventional TNF superfamily member modulator. The compound may be used alone or in combination with a conventional TNF superfamily member modulator. Any condition that results, partially or wholly, from pathogenic signalling through a TNF receptor by a TNF superfamily member or from a deficiency in signalling through a TNF receptor by a TNF superfamily member may in principle be treated, prevented or ameliorated according to the present invention. Pathogenic signalling through a TNF receptor by a TNF superfamily member includes increased signalling through a TNF receptor over and above the normal physiological level of signalling, signalling through a TNF receptor which is initiated normally, but which fails to stop in response to normal physiological signals and signalling through a TNF receptor that is within the normal physiological range of magnitude, but which is initiated by non-physiological means. In a preferred embodiment, the invention relates to the treatment, prevention or amelioration of conditions mediated or influenced by TNFα or CD40L.

The compounds that interact with TNFα are accordingly beneficial in the treatment and/or prevention of various human ailments. These include autoimmune and inflammatory disorders; neurological and neurodegenerative disorders; pain and nociceptive disorders; and cardiovascular disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis, spontaneous infertility, osteoporosis, asthma and muscular dystrophy (including Duchenne muscular dystrophy).

Neurological and neurodegenerative disorders include Alzheimer's disease, Parkinson's disease, Huntington's disease, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction).

In particular, a compound may be used to treat or prevent inflammatory disorders, CNS disorders, immune disorders and autoimmune diseases, pain, osteoporosis, fever and organ transplant rejection. A compound may be used to treat or prevent rheumatoid arthritis, inflammatory bowel diseases (including Crohn's disease), psoriasis, Alzheimer's disease, Parkinson's disease, epilepsy, asthma, sepsis, systemic lupus erythematosus, multiple sclerosis, asthma, rhinitis, cancer and osteoporosis. A compound may be used to treat or prevent rheumatoid arthritis (RA), non specific inflammatory arthritis, erosive bone disease, chondritis, cartilage degeneration and/or destruction, juvenile inflammatory arthritis, Still's Disease (juvenile and/or adult onset), juvenile idiopathic arthritis, juvenile idiopathic arthritis (both oligoarticular and polyarticular forms), inflammatory bowel diseases (including Crohn's disease, ulcerative colitis, indeterminate colitis, pouchitis), psoriasis, psoriatic arthopathy, ankylosing spondylitis, Sjogren's Disease, Alzheimer's disease (AD), Behcet's Disease, Parkinson's disease (PD), amyotrophic lateral sclerosis (ALS), ischemic stroke, pain, epilepsy, osteoporosis, osteopenia, anaemia of chronic disease, cachexia, diabetes, dyslipidemia, metabolic syndrome, asthma, chronic obstructive airways (or pulmonary) disease, sepsis, fever, respiratory distress syndrome, systemic lupus erythematosus (SLE), multiple sclerosis (MS) immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AKI), obstructive uropathy, kidney allograft rejection, cisplatin-induced AKI and obstructive uropathy, eye diseases (including diabetic retinopathy, diabetic macular oedema, retinopathy of prematurity, age related macular degeneration, macular oedema, proliferative and/or non proliferative retinopathy, corneal vascularisation including neovascularization, retinal vein occlusion, various forms of uveitis and keratitis), thyroiditis, fibrosing disorders including various forms of hepatic fibrosis, various forms of pulmonary fibrosis, systemic sclerosis, scleroderma, cancer and cancer associated complications (including skeletal complications, cachexia and anaemia).

As discussed above, antibodies of the present invention may be used as target engagement biomarkers to assess the effectiveness of treatment with a compound or complex as described herein. In one embodiment, a sample taken from a subject treated with a compound or complex described herein may be contacted with an antibody of the invention. The antibody may then be used to determine the amount of TNF superfamily member-compound complex present within the sample. The amount of complex determined using the antibody may be related to the effectiveness of the treatment. For example, the more complex detected by the antibody of the invention, the more effective the treatment. The amount of complex determined using the antibody is directly proportional to the effectiveness of the treatment. For example, doubling the amount of complex determined using the antibody may be indicative of a doubling of the effectiveness of the treatment.

An antibody of the invention may be used to determine the amount of compound-trimer complex using any appropriate technique. Standard techniques are known in the art and are disclosed herein. For example, ELISA and Western blotting with an antibody of the invention may be used to determine the amount of compound-trimer complex.

The amount of the compound-trimer complex may be determined by measuring the mass of the compound-trimer complex, the concentration of the compound-trimer complex, and the molarity of the compound-trimer complex. This amount may be given in any appropriate units. For example, the concentration of the compound-trimer complex may be given in pg/ml, ng/ml or µg/ml. The mass of the compound-trimer complex may be given in pg, ng or µg.

The amount of the compound-trimer complex in a sample of interest may be compared with the level of the compound-trimer complex in another sample, such as a control sample, as described herein. In such a method, the actual amount of the compound-trimer complex, such as the mass, molar amount, concentration or molarity of the compound-trimer complex in the samples may be assessed. The amount of the compound-trimer complex may be compared with that in another sample without quantifying the mass, molar amount, concentration or molarity of the compound-trimer complex. Thus, the amount of the compound-trimer complex in a sample according to the invention may be assessed as a relative amount, such as a relative mass, relative molar amount, relative concentration or relative molarity of the compound-trimer complex based on a comparison between two or more samples.

Pharmaceutical Compositions, Dosages and Dosage Regimes

An antibody, compound or complex of the invention may be provided in a pharmaceutical composition. The pharmaceutical composition that will normally be sterile and will typically include a pharmaceutically acceptable carrier and/or adjuvant. A pharmaceutical composition of the present invention may additionally comprise a pharmaceutically acceptable adjuvant and/or carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. The carrier may be suitable for oral administration. Depending on the route of administration, the modulator may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be desirable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients.

Also within the scope of the present invention are kits comprising antibodies, compounds and/or complexes of the invention and instructions for use. The kit may further contain one or more additional reagents, such as an additional therapeutic or prophylactic agent as discussed above.

The compounds identified by the methods and/or antibodies of the invention and the antibodies of the present invention or formulations or compositions thereof may be administered for prophylactic and/or therapeutic treatments.

In therapeutic applicationscompounds are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is typical.

A compound or pharmaceutical composition of the invention may be administered via one or more routes of administration using one or more of a variety of methods known in the art. As will be appreciated by the skilled artisan, the route and/or mode of administration will vary depending upon the desired results. Examples of routes of administration for compounds or pharmaceutical compositions of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, compound or pharmaceutical composition of the invention can be administered via a non-parenteral route, such as a topical, epidermal or mucosal route of administration. The compound or pharmaceutical composition of the invention may be for oral administration.

A suitable dosage of a compound or pharmaceutical composition of the invention may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the antagonist in the patient and the duration of treatment desired.

As mentioned above, compounds or pharmaceutical composition of the invention may be co-administered with one or other more other therapeutic agents. For example, the other agent may be an analgesic, anaesthetic, immunosuppressant or anti-inflammatory agent.

Combined administration of two or more agents may be achieved in a number of different ways. Both may be administered together in a single composition, or they may be administered in separate compositions as part of a combined therapy. For example, the one may be administered before, after or concurrently with the other.

The following Examples illustrate the invention.

EXAMPLES

Example 1—Synthesis of Compounds

Synthesis of compound (1) is disclosed in WO 2013/186229 (Example 44).
Synthesis of compound (2) is disclosed in WO 2013/186229 (Example 89).
Synthesis of compound (3) is disclosed in WO 2014/009295 (Example 129).
Synthesis of compound (4) is disclosed in WO 2014/009295 (Example 173).
Synthesis of compound (5) is disclosed in WO 2014/009295 (Example 319).
Synthesis of compound (6) is disclosed in WO 2013/186229 (Example 490).

Example 2—Antibody Derivation

Following the immunisation of 5 Sprague Dawley rats with human TNFα in complex with the benzimidazole compound (1), immune B cells were cultured in 96-well plates to induce clonal expansion and antibody secretion (Tickle, S. et al., High throughput screening for high affinity antibodies Journal of Laboratory Automation 2009 14: 303-307). Culture supernatants were screened for IgG antibodies preferentially binding to human TNFα in complex with compound (1) (at a 50 fold molar excess), compared to apo human TNFα, in a homogeneous bead-based FMAT assay. Human TNFα (+/−compound (1)) was presented on bead surfaces (superavidin-coated Bangs Beads, catalogue number CP01N) by a capture system using a human TNF-Receptor I-Fc fusion protein (R&D Systems catalogue number 372-R1-050), bound with biotinylated anti-human Fc (Jackson catalogue number 109-066-098).

Antibodies which demonstrated preferential binding to the TNFα-compound (1) complex were termed 'conformation-selective' and were taken forward for cloning. The Fluorescent Foci method (U.S. Pat. No. 7,993,864/Europe EP1570267B1) was used to identify and isolate antigen-specific B cells from positive wells, and specific antibody variable region genes were recovered from single cells by reverse transcription (RT)-PCR.

The amino acid sequences of two representative antibodies, CA185_01974 and CA185_01979, which demonstrated conformation-selective binding to both human and mouse TNFα+compound are shown below:

```
CA185_01974.0 (VR0001837)
Light chain variable region (LCVR)
(CDRs underlined)
                                       SEQ ID NO: 7
DIQMTQSPASLPASPEEIVTITCQASQDIGNWLSWYQQKPGKSPQLLIYG

ATSLADGVPSRFSASRSGTQYSLKISRLQVEDFGIFYCLQGQSTPYTFGA

GTKLELK

Heavy chain variable region (HCVR)
(CDRs underlined)
                                       SEQ ID NO: 8
DVQLVESGGGLVQPGRSLKLSCAASGFTFSAYYMAWVRQAPTKGLEWVAS

INYDGANTFYRDSVKGRFTVSRDNARSSLYLQMDSLRSEDTATYYCTTEA

YGYNSNWFGYWGQGTLVTVSS

CA185_01979.0 (VR0001842)
Light chain variable region (LCVR)
(CDRs underlined)
                                       SEQ ID NO: 22
DIQMTQSPASLSASLEEIVTITCQASQDIGNWLSWYQQKPGKSPHLLIYG

TTSLADGVPSRFSGSRSGTQYSLKISGLQVADIGIYVCLQAYSTPFTFGS

GTKLEIK

Heavy chain variable region (HCVR)
(CDRs underlined)
                                       SEQ ID NO: 23
EVHLVESGPGLVKPSQSLSLTCSVTGYSITNSYWDWIRKFPGNKMEWMGY

INYSGSTGYNPSLKSRISISRDTSNNQFFLQLNSITTEDTATYYCARGTY

GYNAYHFDYWGRGVMVTVSS
```

Example 3—Potential Epitope of the Derived Antibodies

Given the ability of the rat-derived antibodies to bind to both human and mouse TNFα in the presence of compounds, detailed analysis of rat, mouse and human amino acid sequences, together with X-ray crystal structures of TNFα, was undertaken to see if a likely epitope could be determined.

```
Rat UniProt P16599
                                              (SEQ ID NO: 32)
         10         20         30         40
MSTESMIRDV ELAEEALPKK MGGLQNSRRC LCLSLFSFLL 50         60         70         80
VAGATTLFCL LNFGVIGPNK EEKFPNGLPL ISSMAQTLTL 90        100        110        120
RSSSQNSSDK PVAHVVANHQ AEEQLEWLSQ RANALLANGM 130        140        150        160
DLKDNQLVVP ADGLYLIYSQ VLFKGQGCPD YVLLTHTVSR 170        180        190        200
FAISYQEKVS LLSAIKSPCP KDTPEGAELK PWYEPMYLGG 210        220        230
VFQLEKGDLL SAEVNLPKYL DITESGQVYF GVIAL Mouse UniProt P06804
                                              (SEQ ID NO: 33)
         10         20         30         40
MSTESMIRDV ELAEEALPQK MGGFQNSRRC LCLSLFSFLL 50         60         70         80
VAGATTLFCL LNFGVIGPQR DEKFPNGLPL ISSMAQTLTL 90        100        110        120
RSSSQNSSDK PVAHVVANHQ VEEQLEWLSQ RANALLANGM 130        140        150        160
DLKDNQLVVP ADGLYLVYSQ VLFKGQGCPD YVLLTHTVSR 170        180        190        200
FAISYQEKVN LLSAVKSPCP KDTPEGAELK PWYEPIYLGG 210        220        230
VFQLEKGDQL SAEVNLPKYL DFAESGQVYF GVIAL Human UniProt P01375
                                              (SEQ ID NO: 34)
         10         20         30         40
MSTESMIRDV ELAEEALPKK TGGPQGSRRC LFLSLFSFLI 50         60         70         80
VAGATTLFCL LHFGVIGPQR EEFPRDLSLI SPLAQAVRSS 90        100        110        120
SRTPSDKPVA HVVANPQAEG QLQWLNRRAN ALLANGVELR 130        140        150        160
DNQLVVPSEG LYLIYSQVLF KGQGCPSTHV LLTHTISRIA 170        180        190        200
VSYQTKVNLL SAIKSPCQRE TPEGAEAKPW YEPIYLGGVF 210        220        230
QLEKGDRLSA EINRPDYLDF AESGQVYFGI IAL
```

From alignments and comparison of the rat, mouse and human TNFα UniProt sequences, examples of where the rat amino acid sequence differs from the human, and where the human and mouse sequences are identical in the mature, cleaved product include N168, I194, F220 and A221 (residues and numbering from the human sequence).

These residues are highlighted on the crystal structure of human TNFα (1TNF) (FIG. 1). It is possible that any of these amino acids are included in the epitope targeted by the antibodies CA185_01974 and CA185_01979.

Following cloning of the antibody variable regions into mouse IgG and mouse Fab (no-hinge) vectors, the conformation-selective nature of the binding of antibodies CA185_01974 and CA185_01979 was confirmed, using a variety of test compounds bound to TNFα, in HPLC, BIAcore, ELISA and cell-based assays.

Figure 2:
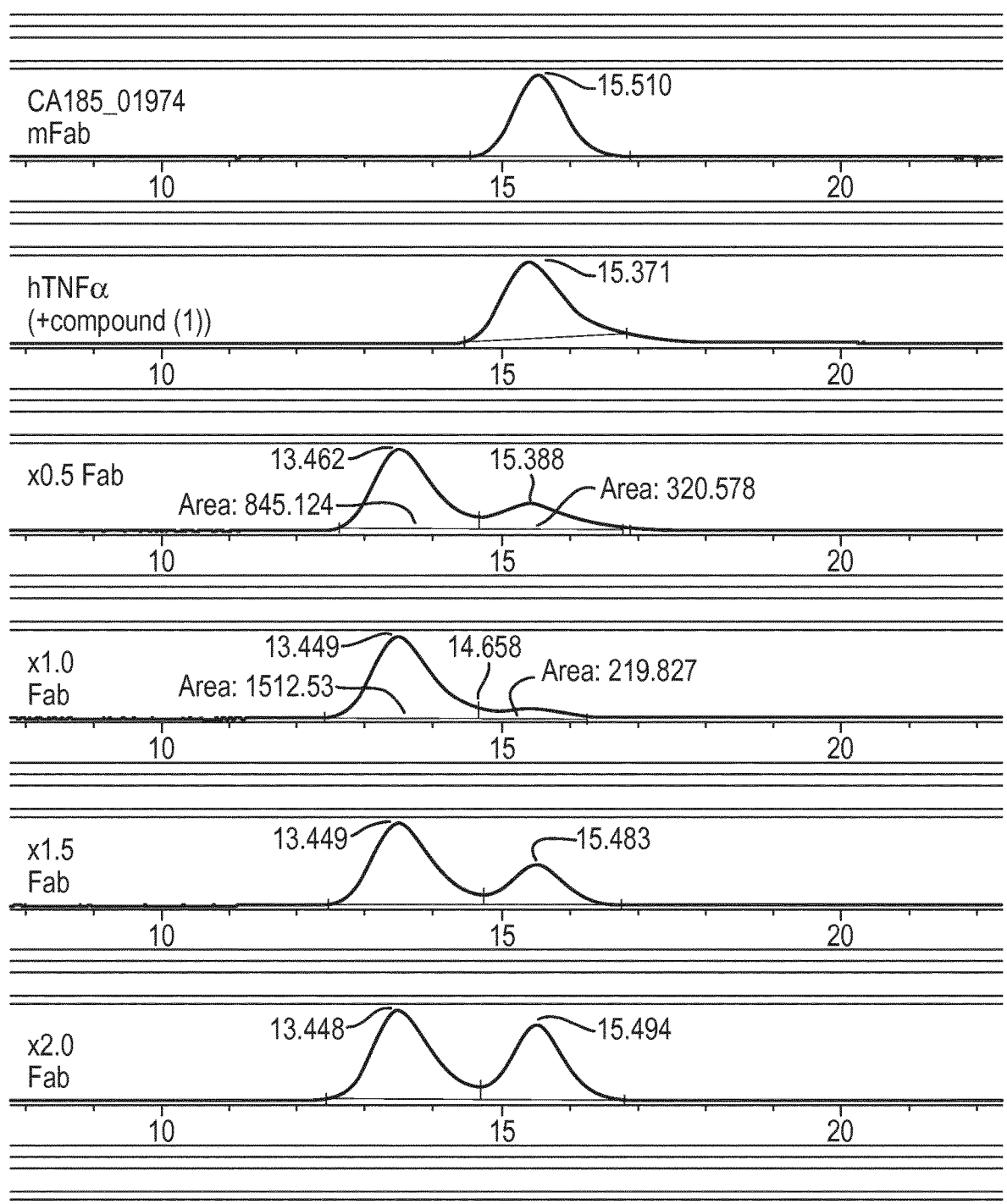

Example 4—High Performance Liquid Chromatography (HPLC) to Determine Antibody Characteristics Specific binding of mouse Fab fragments was demonstrated by complex formation between CA185_01974 and human TNFα complexed with compound (1) using size exclusion chromatography. Results are shown in FIG. 2. As shown in this Figure, with a 0.5× molar excess of Fab the predominant peak corresponds to bound Fab and trimer-compound complex (although there is a small peak showing the presence of some trimer-compound complex not bound to Fab). At a 1.0× molar excess of Fab there is single higher molecular weight peak corresponding to Fab bound to trimer-compound complex. At 1.5× and 2× molar excesses of Fab, there is a growing lower molecular peak corresponding to unbound Fab.

The stoichiometry was therefore determined to be 1 Fab:1 TNFα trimer, with excess Fab appearing at 1.5× and 2× molar excess.

Figure 3:
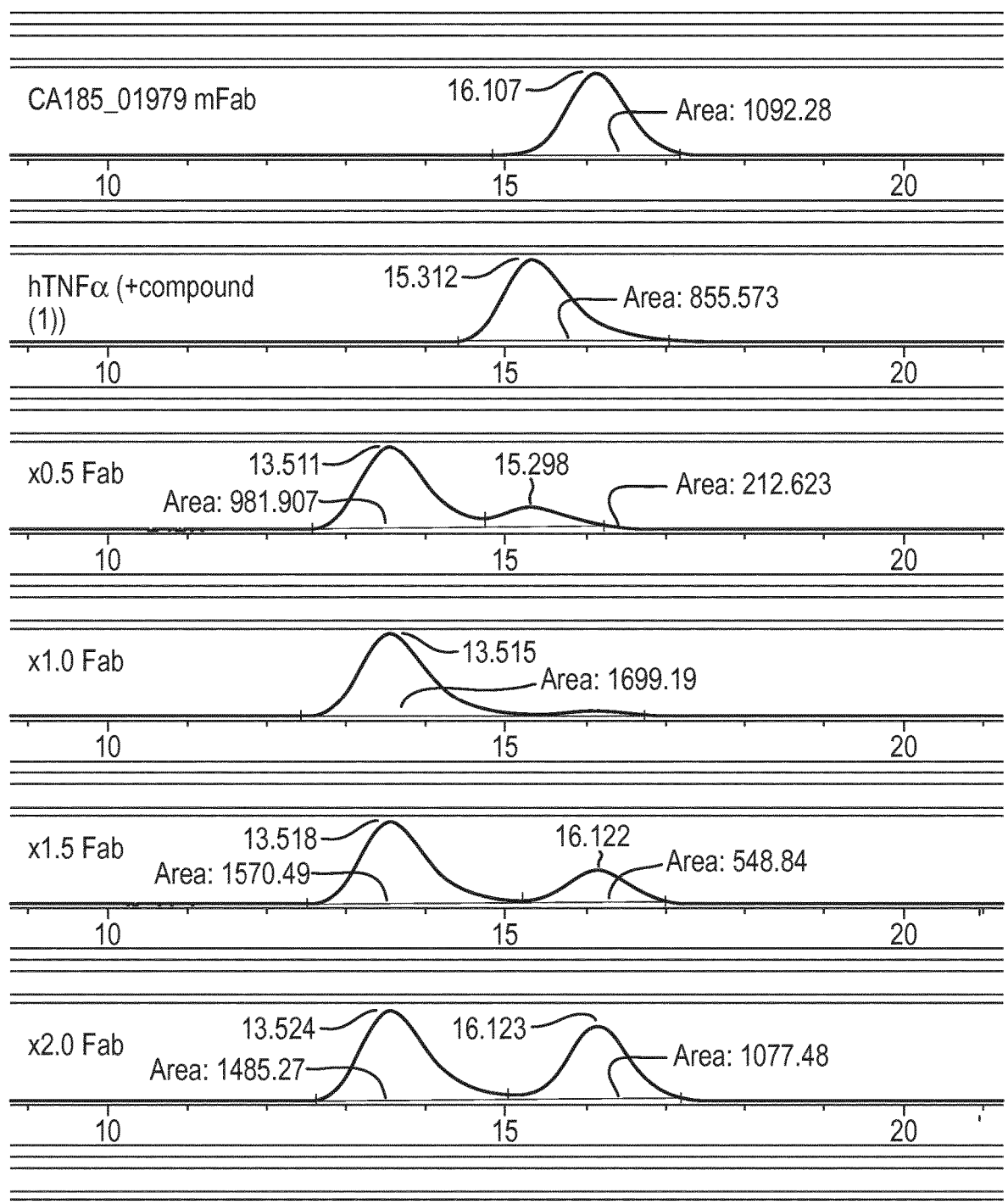

Binding of CA185_01979 to human TNFα complexed with compound (1) was also investigated using size exclusion chromatography. Results are shown in FIG. 3. As for CA185_01974, the stoichiometry was determined to be 1 Fab:1 TNFα trimer, with excess Fab appearing at 1.5× and 2× molar excess.

Example 5—BIAcore Assays to Determine Antibody Characteristics

Surface plasmon resonance was performed at 25° C. using a BIAcore T200 (GE Healthcare). Anti-Mouse Fc (Jackson 115-006-071) was immobilised on a CM5 Sensor Chip (GE Healthcare) via amine coupling chemistry to a capture level of ~6000 response units. HBS-EP buffer (10 mM HEPES pH 7.4, 0.15 M NaCl, 3 mM EDTA, 0.05% (v/v) surfactant P20—GE Healthcare)+1% DMSO was used as the running buffer. A 10 μl injection of each IgG at 1 μg/ml was used for capture by the immobilised anti-mouse Fc to create the TNFα-binding surface. Human or mouse TNFα (in-house) at 50 nM was pre-incubated with 2 μM compound in HBS-EP+ (1% DMSO) for 5 hours.

A 3 minute injection of human or mouse TNFα+/−test compound was passed over each captured IgG at a flow rate of 30 μl/min. The surface was regenerated at a flow-rate of 10 μl/min by a 60 s injection of 40 mM HCl×2 and a 30 s 5 mM NaOH. Double referenced background subtracted binding curves were analysed using the T200 Evaluation software (version 1.0) following standard procedures. Kinetic parameters were determined from the fitting algorithm.

The kinetic binding data for human and mouse TNFα in the presence and absence of test compounds from two chemical series are shown in Tables 1 and 2 below.

TABLE 1

| BIAcore data with human TNFα | | | | |
|---|---|---|---|---|
| Antibody | Human TNFα | ka (M$^{-1}$s$^{-1}$) | kd (s$^{-1}$) | KD (M) |
| CA185_01974 | +compound (2) | $4.2 \times 10^5$ | $3.9 \times 10^{-5}$ | $9.4 \times 10^{-11}$ |
| CA185_01974 | +compound 1 | $3.2 \times 10^5$ | $3.8 \times 10^{-5}$ | $1.2 \times 10^{-10}$ |

TABLE 1-continued

BIAcore data with human TNFα

| Antibody | Human TNFα | ka (M$^{-1}$s$^{-1}$) | kd (s$^{-1}$) | KD (M) |
|---|---|---|---|---|
| CA185_01974 | apo | 6.6 × 10$^4$ | 1.3 × 10$^{-3}$ | 1.9 × 10$^{-8}$ |
| CA185_01979 | +compound (2) | 5.7 × 10$^5$ | 3.3 × 10$^{-5}$ | 5.8 × 10$^{-11}$ |
| CA185_01979 | +compound (1) | 4.7 × 10$^5$ | 1.6 × 10$^{-5}$ | 3.4 × 10$^{-11}$ |
| CA185_01979 | apo | 1.1 × 10$^5$ | 7.1 × 10$^{-4}$ | 6.7 × 10$^{-9}$ |

Both CA185_01974 and CA185_01979 demonstrated >2 log selective binding for compound-distorted human TNFα, with representative test compounds from two chemical series.

TABLE 2

BIAcore data with mouse TNFα

| Antibody | Mouse TNFα | ka (M$^{-1}$s$^{-1}$) | kd (s$^{-1}$) | KD (M) |
|---|---|---|---|---|
| CA185_01974 | +compound (2) | 6.7 × 10$^4$ | 4.8 × 10$^{-5}$ | 7.1 × 10$^{-10}$ |
| CA185_01974 | +compound (1) | 5.8 × 10$^4$ | 8.8 × 10$^{-5}$ | 1.5 × 10$^{-9}$ |
| CA185_01974 | apo | 4.2 × 10$^4$ | 4.9 × 10$^{-3}$ | 1.2 × 10$^{-7}$ |
| CA185_01979 | +compound (2) | 1.9 × 10$^5$ | 3.5 × 10$^{-5}$ | 1.9 × 10$^{-10}$ |
| CA185_01979 | +compound (1) | 1.6 × 10$^5$ | 6.3 × 10$^{-5}$ | 3.8 × 10$^{-10}$ |
| CA185_01979 | apo | 7.2 × 10$^4$ | 2.0 × 10$^{-3}$ | 2.7 × 10$^{-8}$ |

Both CA185_01974 and CA185_01979 demonstrated >1.5 and >2 log selective binding for compound-distorted mouse TNFα, with representative test compounds from two chemical series.

Example 6—ELISAs to Determine Antibody Characteristics

A sandwich ELISA was developed to measure the concentration of TNFα bound to compounds of the invention, using antibody CA185_01974.0 that specifically detects the conformation of TNFα when in complex with these compounds. Briefly, a microtitre plate was coated with CA185_01974.0 to immobilise TNFα in complex with a test compound. TNFα was incubated overnight at 28° C. with a 50× molar excess of the test compound. Following this overnight incubation, TNFα was serially diluted in neat human plasma depleted of endogenous TNFα, in the presence of heterophilic antibody blockers, and added to the coated plate. Curves were generated with a concentration range of 0.78 pg/ml-50 pg/ml TNFα. A biotinylated polyclonal anti TNFα antibody was used to detect bound TNFα, with streptavidin-peroxidase and TMB substrate to give a colorimetric signal. Sensitivity of the assay was increased with the use of tyramide signal amplification, using the ELAST kit from Perkin Elmer, as an additional step between streptavidin-peroxidase and the substrate.

An ELISA was also developed to measure total TNFα (free TNFα+TNFα in complex with a test compound) in parallel. For this assay the coating antibody was replaced with a commercial anti-TNFα polyclonal antibody (Invitrogen AHC3812). The sample incubation time was also increased to 3 hours. All other steps were identical to the conformation-specific assay. This enables the amount of TNFα in complex with a test compound to be calculated as a proportion of total TNFα.

Figure 4:
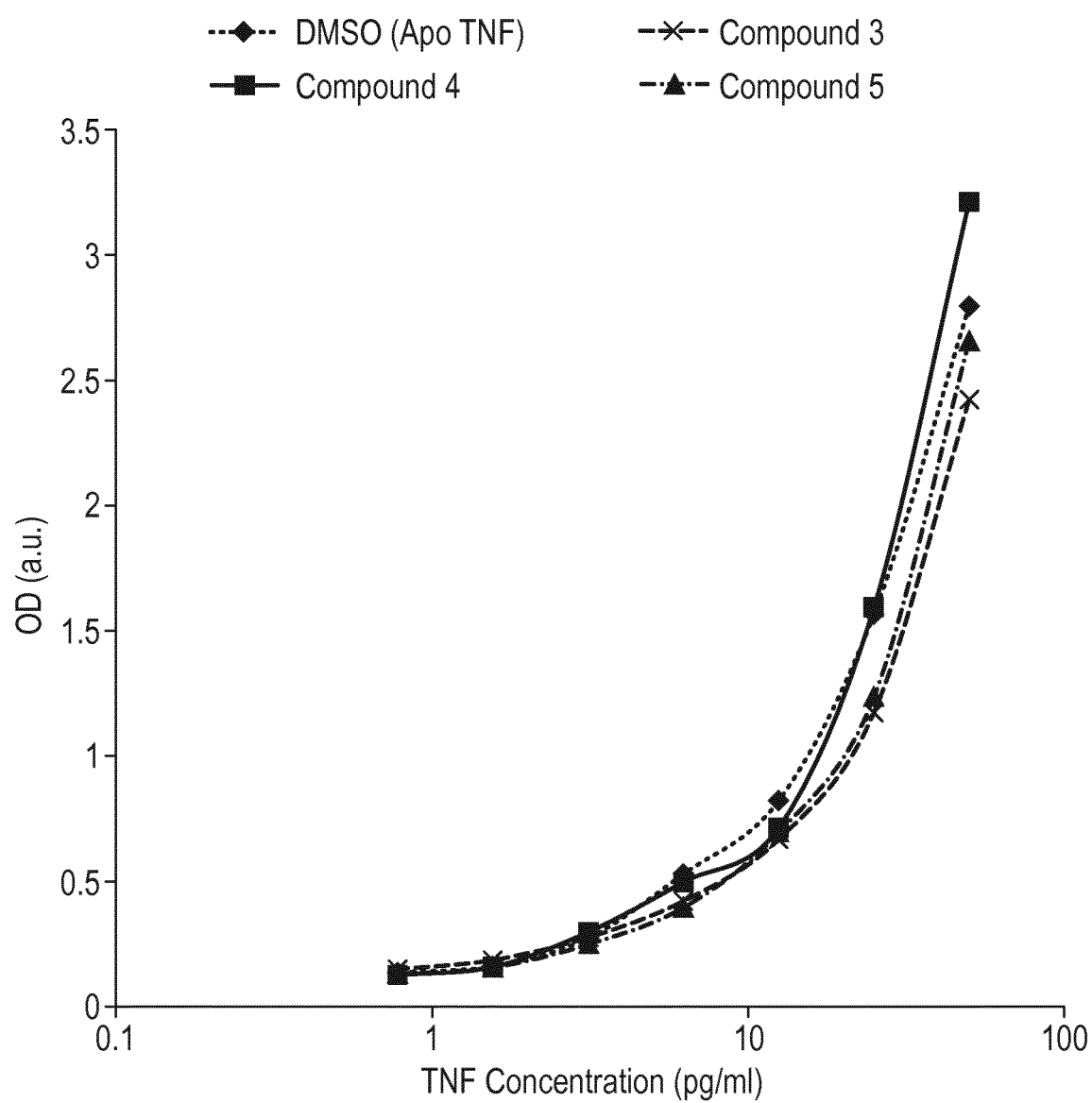

Results for the total TNFα ELISA with compounds (3), (4) and (5) are shown in FIG. 4.

Figure 5:
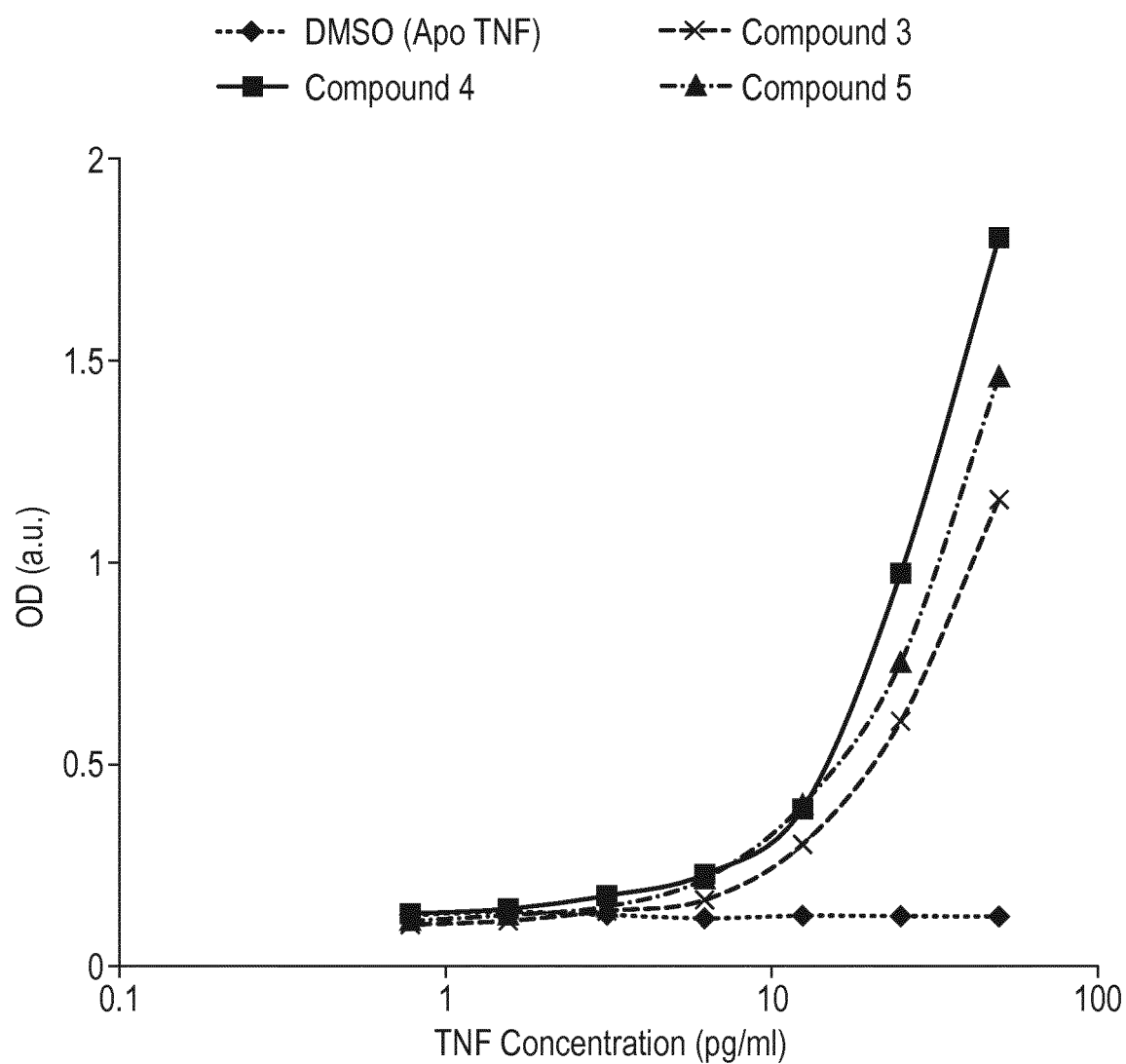

Results of the conformation specific TNFα ELISA with CA185_01974.0 and compounds (3), (4) and (5) are shown in FIG. 5. Apo TNFα gave no signal in this assay, demonstrating the specific nature of the binding of antibody CA185_01974 to compound-bound TNFα. The antibody was able to recognise TNFα bound by a variety of test compounds from different chemical series.

Example 7—Cell-based Assays to Determine Antibody Characteristics

Recombinant antibodies were also tested for binding to compound-distorted TNFα in a FACS assay using human embryonic kidney (HEK) JumpIn cells, which overexpress TNF-RI after induction with doxycycline at 1 µg/ml for 2.5 hours. HEK cells were trypsinised and incubated for 2 h in medium to allow recovery of digested TNFRI levels. Human TNFα at 2 µg/mL was pre-incubated with 40 µM compound (1) or 0.4% DMSO for 1 h at 37° C. The preincubation mix was added to the cells for 1 h on ice (dilution 1:4, final concentrations: 0.5 µg/mL human-TNFα+/−10 µM compound (1) or 0.1% DMSO). Cells were washed, fixed (1.5% PFA) and stained with 1 or 10 µg/mL antibody for 1 h on ice. (Secondary antibody: anti-mouse-Alexa488), before analysis for receptor-bound TNFα.

Figure 6:
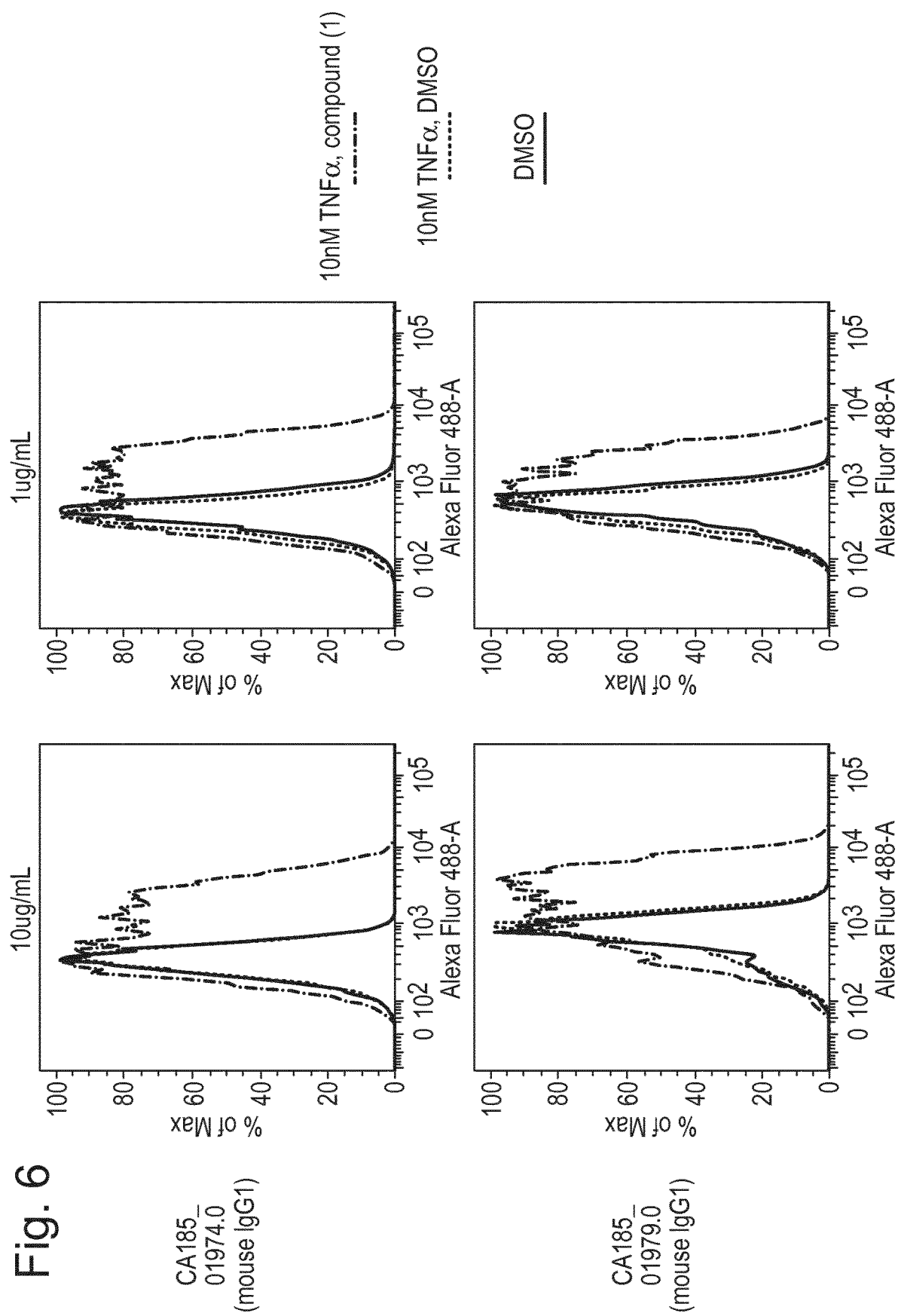

As shown in FIG. 6, FACS histogram plots of staining with CA185_01974 and CA185_01979 at 1 and 10 µg/ml demonstrate that the antibodies only recognise TNFα which has been pre-incubated with compound (1). There is no staining with the DMSO control.

In addition, specific binding of CA185_01974 and CA185-01979 Fab fragments was demonstrated with compound-distorted membrane-bound TNFα. An engineered NS0 cell line, which overexpresses membrane TNFα, due to knock-out of the TACE cleavage site was incubated with 0.001-10 µM compound (1) or 0.1% DMSO for 1 h at 37° C. Cells were washed, fixed and stained with antibody Fab fragments at 0.01 or 0.1 µg/ml for 1 hour on ice. (Secondary antibody was anti-mouse Fab-DyeLight488 from Jackson ImmunoResearch).

Figure 7:
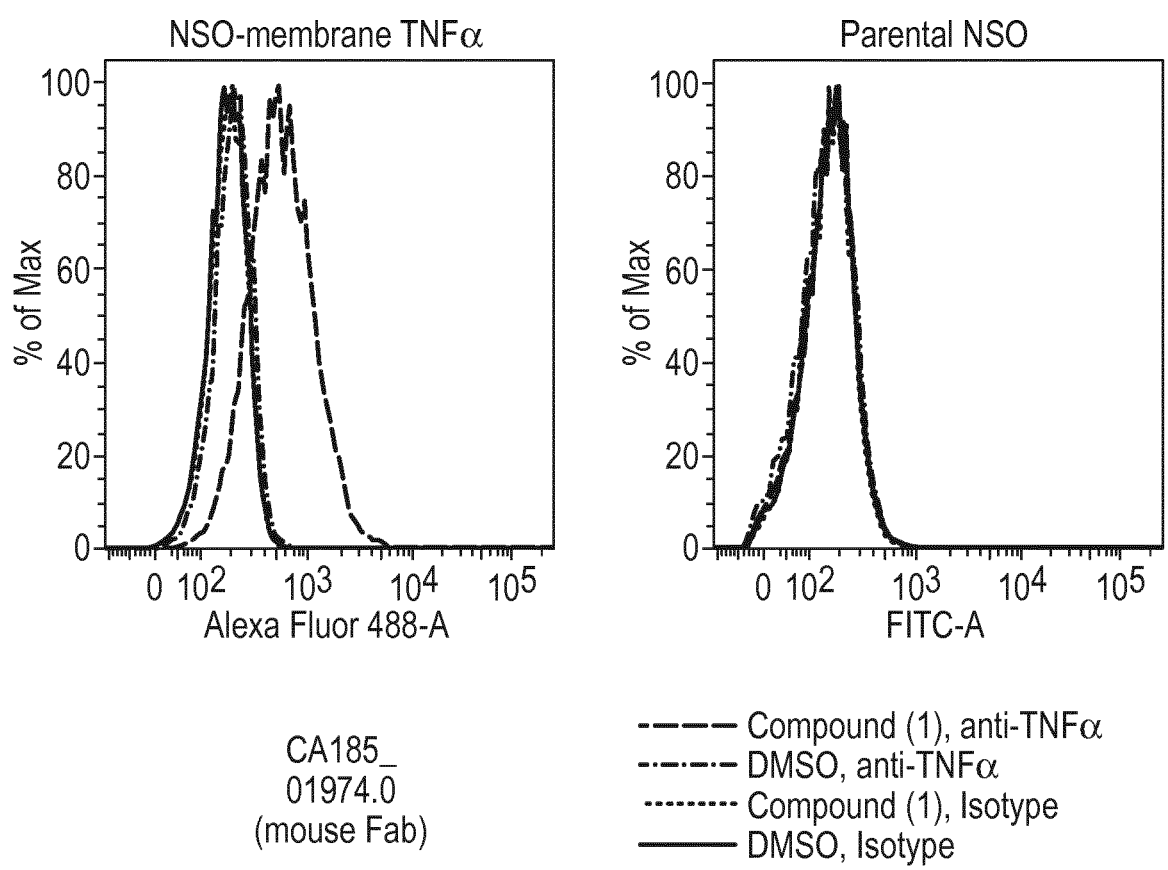

FACS histogram plots of staining with CA185_01974 (FIG. 7) and CA185_01979 Fab fragments demonstrate that the antibodies only recognise TNF which has been pre-incubated with compound (1). There is no staining with the DMSO controls.

Example 8—Antibody CA185_01974, Shows a 300-Fold Selectivity for Human TNF-Compound (4) Complex Compound (4) was incubated with human and cynomolgus TNF and titrated over mouse full length antibody CA185_01974 to determine an accurate affinity value. The experiment included the following controls: (i) human or cynomolgus TNF+DMSO over 1974; (ii) human or cynomolgus TNF+DMSO over no antibody; and (iii) human or cynomolgus TNF+compound (4) over no antibody. Each sample and control was carried out in duplicate and used four concentrations in each replicate.

As shown in FIGS. 8 and 9, background binding of hTNF+compound (4) and cTNF+compound (4) increased by 5-10RU over the course of the assay. This is seen in the higher response of h/cTNF+compound (4) binding to CA185_01974 in the second duplicate. Binding of hTNF and cTNF in the absence of compound (4) was consistently very low.

Kinetics of hTNF+DMSO binding mouse full length IgG CA185_1974_P8 was very similar in this assay to previous single concentration analysis. Affinity of cynomolgus TNF for mouse full length IgG CA185_1974_P8 is similar, however the kinetics differ.

Table 3 gives the kinetics of each analyte binding to CA185_1974_P8. Table 4 gives the average values and the fold difference+/−compound (4) of TNF kinetics for CA185_1974_p8. FIG. 8 gives the sensograms of both duplicates of cTNF+/−compound (4). FIG. 9 gives the sensograms of both duplicates of hTNF+/−compound (4).

domain2 of TNFR1 in its interaction with the external surface of TNFβ. The C87 compound from Ma et al. and the BIO08898 compound from Silvian et al. (2011) ACS Chemical Biology 6:636-647 were tested by the present inventors.

Summary of Findings

The Biacore observations described in Ma et al. for C87 could not be repeated.

TABLE 3

Binding kinetics of hTNF and cTNF +/− compound (4) to the CA185_1974_P8 antibody

| Duplicate | Antibody | Analyte | ka (1/Ms) | kd (1/s) | KD (M) | KD (pM) |
|---|---|---|---|---|---|---|
| 1 | CA185_1974_P8 | cyno TNF | 1.03E+05 | 1.87E−03 | 1.83E−08 | 18270 |
| 2 | CA185_1974_P8 | cyno TNF | 1.25E+05 | 1.92E−03 | 1.54E−08 | 15350 |
| 1 | CA185_1974_P8 | cyno TNF + compound (4) | 1.84E+05 | 1.46E−05 | 7.91E−11 | 79.1 |
| 2 | CA185_1974_P8 | cyno TNF + compound (4) | 2.01E+05 | 2.06E−05 | 1.03E−10 | 103 |
| 1 | CA185_1974_P8 | human TNF | 8.02E+04 | 1.77E−03 | 2.21E−08 | 22100 |
| 2 | CA185_1974_P8 | human TNF | 1.05E+05 | 1.67E−03 | 1.59E−08 | 15900 |
| 1 | CA185_1974_P8 | human TNF + compound (4) | 3.06E+05 | 1.00E−05 | 3.27E−11 | 32.7 |
| 2 | CA185_1974_P8 | human TNF + compound (4) | 3.07E+05 | 2.73E−05 | 8.88E−11 | 88.8 |

TABLE 4

Average values and fold differences +/− compound (4) of hTNF and cTNF kinetics for CA185_1974_p8.

| Average of duplicates | ka (1/Ms) | kd (1/s) | KD (M) | KD (pM) |
|---|---|---|---|---|
| cyno TNF | 1.14E+05 | 1.90E−03 | 1.68E−08 | 16810 |
| cyno TNF + compound (4) | 1.93E+05 | 1.76E−05 | 9.09E−11 | 90.92 |
| Fold difference | 1.69 | 107.81 | 184.89 | 184.89 |
| human TNF | 9.27E+04 | 1.72E−03 | 1.90E−08 | 19000 |
| human TNF + compound (4) | 3.06E+05 | 1.86E−05 | 6.08E−11 | 60.76 |
| Fold difference | 3.31 | 92.43 | 312.70 | 312.70 |

Conclusions

The antibodies CA185_01974 and CA185_01989 have been demonstrated specifically to bind to a compound-distorted state of TNFα, and will be useful target-engagement biomarkers for compounds of the invention.

The antibodies have been shown to bind to a conformation of TNFα, which is specifically stabilised by compounds from different chemical series. It is envisaged that these antibodies will become standards in defining this, and closely related, biologically relevant conformations, of the TNFα trimer, which are stabilised by a wider range of chemical series than are described here. Based on the data shown, the human TNFα trimer could be considered to be stabilised in the defined, biologically relevant conformation described if either CA185_01974 or CA185_01989 antibody binds with a $K_D$ better than 1 nM in the BIAcore assay format described above.

Example 9—Compounds and Complexes of Ma et al (2014) and Silvian et al (2011) have Different Characteristics to Those of the Present Invention As described on page 12458 of Ma et al. (2014) JBC 289:12457-12466, C87 was discovered through virtual screening by attempting to find molecules which fit the space occupied by a 7 amino-acid peptide from loop2/

No evidence of TNF specific inhibition in cells was observed.

Additionally C87 was not observed to bind by mass spectrometry, which is sensitive to millimolar affinities.

Extensive crystallography trials only produced apo-TNF (TNF without compound).

In the fluorescence polarisation (FP) assay, C87 showed no significant inhibition above the interference level of the compound with the fluorescent read-out.

Thermofluor, which measures stabilisation of the thermal melting temperature of TNFα, did show a small stabilisation for C87.

In summary, no evidence was found that C87 binds in the centre of the trimer. The overwhelming majority of the data suggested no direct interaction with TNFα. BIO8898 was also found not to bind to TNFα.

Cells—TNF induced HEK NFKB reporter gene assay

C87 was preincubated with TNFα for 1 hour prior to the addition to HEK-293 cells stably transfected with SEAP under the control of NFκB. An appropriate counter-screen was also tested in order to detect non-TNF related (off target) activity. The assay was incubated overnight before inhibition was measured compared to 100% blocking by a control compound. The maximum C87 concentration was 10,000 nM, with a 3-fold serial dilution.

No inhibitory effect could be detected that could not be attributed to off-target activity.

Biacore

TNF was immobilised using an avi-tag linker and C87 was passed over the chip. In one experiment, a dose response of C87 from a highest concentration of 10 μM was performed. No binding was observed.

In a second experiment, the flow rate of C87 passing over the chip was reduced. A small shift was observed but overall binding was negligible.

The binding of C87 to TNF described in Ma et al was likely to be super-stoichiometric based on the RU value on the Y-axis. At standard TNF density on the chip this value was in the region of thirty times higher than expected for simple 1:1 binding.

In another experiment, BIO08898 was tested against the immobilised soluble form of CD40L and the soluble form of TNFα by SPR on a Biacore 4000 machine. A geomean IC50 of 17 μM was determined for binding against CD40L whereas no binding was detected at a concentration of up to 100 μM for TNFα in this assay.

Mass Spectrometry

There was no evidence of C87 binding to human TNFα (20 μM) at a concentration of 400 μM. A species of lower molecular weight (~473 Da appears to bind at less than 5% occupancy). C87 has a molecular weight of 503 Da. Based on the occupancy at a concentration of 400 μM, an affinity of the low molecular weight species in excess of 1 mM is predicted.

Crystallography

Overall a large effort was put into crystallising C87 with TNFα, including testing conditions that routinely work with compounds described in the present application. This comprised setting up a large number of crystallization trials at different ligand concentrations, different protein concentrations, and different soaking times. A few crystals were observed that, on analysis, proved to be salt or TNF with no compound.

Fluorescent Polarization (FP)

C87 was preincubated with TNFα for 1 hour prior to assay against the fluorescent compound (probe). Competition with the fluorescent compound either directly (binding at the same site) or indirectly (disrupting TNF) is detected by a reduction in FP.

Extrapolation of the inhibition curve produced an IC50 of about 100 μM. Fluorescence quenching was, however, observed at the highest concentrations of inhibitor which, when subtracted, resulted in negligible inhibition of C87 in this assay.

Thermofluor

Thermofluor measures the change of melting temperature (Tm) of TNFα due to compound either stabilising or disrupting the protein. A stabilization effect of 3.8° C. was observed at a concentration of 500 μM C87, suggesting the possibility of weak binding, which may not be specific.

| Sequence listing |
| --- |
| SEQ ID NO: 1 (LCDR1 of 1974)<br>QASQDIGN |
| SEQ ID NO: 2 (LCDR2 of 1974)<br>GATSLAD |
| SEQ ID NO: 3 (LCDR3 of 1974)<br>LQGQSTPYT |
| SEQ ID NO: 4 (HCDR1 of 1974)<br>AYYMA |
| SEQ ID NO: 5 (HCDR2 of 1974)<br>ASINYDGANTFYRDSVKG |
| SEQ ID NO: 6 (HCDR3 of 1974)<br>EAYGYNSNWFGY |
| SEQ ID NO: 7 (LCVR of 1974)<br>DIQMTQSPASLPASPEEIVTITCQASQDIGNWLSWYQQKPGKSPQLLIYG<br>ATSLADGVPSRFSASRSGTQYSLKISRLQVEDFGIFYCLQGQSTPYTFGA<br>GTKLELK |
| SEQ ID NO: 8 (HCVR of 1974)<br>DVQLVESGGGLVQPGRSLKLSCAASGFTFSAYYMAWVRQAPTKGLEWVAS<br>INYDGANTFYRDSVKGRFTVSRDNARSSLYLQMDSLRSEDTATYYCTTEA<br>YGYNSNWFGYWGQGTLVTVSS |

| Sequence listing |
| --- |
| SEQ ID NO: 9 (LCVR DNA of 1974)<br>GACATCCAGATGACCCAGTCTCCTGCCTCCCTGCCTGCATCCCCGGAAGA<br>AATTGTCACCATCACATGCCAGGCAAGCCAGGACATTGGTAATTGGTTAT<br>CATGGTATCAGCAGAAACCAGGGAAATCGCCTCAGCTCCTGATCTATGGT<br>GCAACCAGCTTGGCAGATGGGGTCCCATCAAGGTTCAGCGCCAGTAGATC<br>TGGCACACAGTACTCTCTTAAGATCAGCAGACTGCAGGTTGAAGATTTTG<br>GAATCTTTTACTGTCTACAGGGTCAAAGTACTCCGTACACGTTTGGAGCT<br>GGGACCAAGCTGGAACTGAAA |
| SEQ ID NO: 10 (HCVR DNA of 1974)<br>GACGTGCAGCTGGTGGAATCTGGAGGAGGCTTAGTGCAGCCTGGAAGGTC<br>CCTGAAACTCTCCTGTGCAGCCTCAGGATTCACTTTCAGTGCCTATTACA<br>TGGCCTGGGTCCGCCAGGCTCCAACGAAGGGTCTGGAGTGGGTCGCATCC<br>ATTAATTATGATGGTGCTAACACTTTCTATCGCGACTCCGTGAAGGGCCG<br>ATTCACTGTCTCCAGAGATAATGCAAGAAGCAGCCTATACCTACAAATGG<br>ACAGTCTGAGGTCTGAGGACACGGCCACTTATTACTGTACAACAGAGGCT<br>TACGGATATAACTCAAATTGGTTTGGTTACTGGGGCCAAGGCACTCTGGT<br>CACTGTCTCGAGC |
| SEQ ID NO: 11 (1974 LC kappa full)<br>DIQMTQSPASLPASPEEIVTITCQASQDIGNWLSWYQQKPGKSPQLLIYG<br>ATSLADGVPSRFSASRSGTQYSLKISRLQVEDFGIFYCLQGQSTPYTFGA<br>GTKLELKRTDAAPTVSIFPPSSEQLTSGGASVVCFLNNFYPKDINVKWKI<br>DGSERQNGVLNSWTDQDSKDSTYSMSSTLTLTKDEYERHNSYTCEATHKT<br>STSPIVKSFNRNEC |
| SEQ ID NO: 12 (1974 HC mIgG1 full)<br>DVQLVESGGGLVQPGRSLKLSCAASGFTFSAYYMAWVRQAPTKGLEWVAS<br>INYDGANTFYRDSVKGRFTVSRDNARSSLYLQMDSLRSEDTATYYCTTEA<br>YGYNSNWFGYWGQGTLVTVSSAKTTPPSVYPLAPGSAAQTNSMVTLGCLV<br>KGYFPEPVTVTWNSGSLSSGVHTFPAVLQSDLYTLSSSVTVPSSTWPSET<br>VTCNVAHPASSTKVDKKIVPRDCGCKPCICTVPEVSSVFIFPPKPKDVLT<br>ITLTPKVTCVVVDISKDDPEVQFSWFVDDVEVHTAQTQPREEQFNSTFRS<br>VSELPIMHQDWLNGKEFKCRVNSAAFPAPIEKTISKTKGRPKAPQVYTIP<br>PPKEQMAKDKVSLTCMITDFFPEDITVEWQWNGQPAENYKNTQPIMDTDG<br>SYFVYSKLNVQKSNWEAGNTFTCSVLHEGLHNHHTEKSLSHSPGK |
| SEQ ID NO: 13 (1974 HC mFabno hinge full)<br>DVQLVESGGGLVQPGRSLKLSCAASGFTFSAYYMAWVRQAPTKGLEWVAS<br>INYDGANTFYRDSVKGRFTVSRDNARSSLYLQMDSLRSEDTATYYCTTEA<br>YGYNSNWFGYWGQGTLVTVSSAKTTPPSVYPLAPGSAAQTNSMVTLGCLV<br>KGYFPEPVTVTWNSGSLSSGVHTFPAVLQSDLYTLSSSVTVPSSTWPSET<br>VTCNVAHPASSTKVDKKIVPRDC |
| SEQ ID NO: 14 (1974 LC DNA kappa full)<br>GACATCCAGATGACCCAGTCTCCTGCCTCCCTGCCTGCATCCCCGGAAGA<br>AATTGTCACCATCACATGCCAGGCAAGCCAGGACATTGGTAATTGGTTAT<br>CATGGTATCAGCAGAAACCAGGGAAATCGCCTCAGCTCCTGATCTATGGT<br>GCAACCAGCTTGGCAGATGGGGTCCCATCAAGGTTCAGCGCCAGTAGATC<br>TGGCACACAGTACTCTCTTAAGATCAGCAGACTGCAGGTTGAAGATTTTG<br>GAATCTTTTACTGTCTACAGGGTCAAAGTACTCCGTACACGTTTGGAGCT<br>GGGACCAAGCTGGAACTGAAACGTACGGATGCTGCACCAACTGTATCCAT<br>CTTCCCACCATCCAGTGAGCAGTTAACATCTGGAGGTGCCTCAGTCGTGT<br>GCTTCTTGAACAACTTCTACCCCAAAGACATCAATGTCAAGTGGAAGATT<br>GATGGCAGTGAACGACAAAATGGCGTCCTGAACAGTTGGACTGATCAGGA<br>CAGCAAAGACAGCACCTACAGCATGAGCAGCACCCTCACGTTGACCAAGG<br>ACGAGTATGAACGACATAACAGCTATACCTGTGAGGCCACTCACAAGACA<br>TCAACTTCACCCATTGTCAAGAGCTTCAACAGGAATGAGTGT |
| SEQ ID NO: 15 (1974 HC DNA mIgG1 full)<br>GACGTGCAGCTGGTGGAATCTGGAGGAGGCTTAGTGCAGCCTGGAAGGTC<br>CCTGAAACTCTCCTGTGCAGCCTCAGGATTCACTTTCAGTGCCTATTACA<br>TGGCCTGGGTCCGCCAGGCTCCAACGAAGGGTCTGGAGTGGGTCGCATCC<br>ATTAATTATGATGGTGCTAACACTTTCTATCGCGACTCCGTGAAGGGCCG<br>ATTCACTGTCTCCAGAGATAATGCAAGAAGCAGCCTATACCTACAAATGG<br>ACAGTCTGAGGTCTGAGGACACGGCCACTTATTACTGTACAACAGAGGCT<br>TACGGATATAACTCAAATTGGTTTGGTTACTGGGGCCAAGGCACTCTGGT<br>CACTGTCTCGAGTGCCAAAACGACACCCCCATCTGTCTATCCACTGGCCC<br>CTGGATCTGCTGCCCAAACTAACTCCATGGTGACCCTGGGATGCCTGGTC<br>AAGGGCTATTTCCCTGAGCCAGTGACAGTGACCTGGAACTCTGGATCCCT<br>GTCCAGCGGTGTGCACACCTTCCCAGCTGTCCTGCAGTCTGACCTCTACA<br>CTCTGAGCAGCTCAGTGACTGTCCCCTCCAGCACCTGGCCCAGCGAGACC<br>GTCACCTGCAACGTTGCCCACCCGGCCAGCAGCACCAAGGTGGACAAGAA<br>AATTGTGCCCAGGGATTGTGGTTGTAAGCCTTGCATATGTACAGTCCCAG<br>AAGTATCATCTGTCTTCATCTTCCCCCCAAAGCCCAAGGATGTGCTCACC<br>ATTACTCTGACTCCTAAGGTCACGTGTGTTGTGGTAGACATCAGCAAGGA<br>TGATCCCGAGGTCCAGTTCAGCTGGTTTGTAGATGATGTGGAGGTGCACA |

```
CAGCTCAGACGCAACCCCGGGAGGAGCAGTTCAACAGCACTTTCCGCTCA
GTCAGTGAACTTCCCATCATGCACCAGGACTGGCTCAATGGCAAGGAGTT
CAAATGCAGGGTCAACAGTGCAGCTTTCCCTGCCCCCATCGAGAAAACCA
TCTCCAAAACCAAAGGCAGACCGAAGGCTCCACAGGTGTACACCATTCCA
CCTCCCAAGGAGCAGATGGCCAAGGATAAAGTCAGTCTGACCTGCATGAT
AACAGACTTCTTCCCTGAAGACATTACTGTGGAGTGGCAGTGGAATGGGC
AGCCAGCGGAGAACTACAAGAACACTCAGCCCATCATGGACACAGATGGG
TCTTACTTCGTCTACAGCAAGCTCAATGTGCAGAAGAGCAACTGGGAGGC
AGGAAATACTTTCACCTGCTCTGTGTTACATGAGGGCCTGCACAACCACC
ATACTGAGAAGAGCCTCTCCCACTCTCCTGGTAAA

SEQ ID NO: 16 (1974 HC DNA mFabno hinge full)
GACGTGCAGCTGGTGGAATCTGGAGGAGGCTTAGTGCAGCCTGGAAGGTC
CCTGAAACTCTCCTGTGCAGCCTCAGGATTCACTTTCAGTGCCTATTACA
TGGCCTGGGTCCGCCAGGCTCCAACGAAGGGTCTGGAGTGGGTCGCATCC
ATTAATTATGATGGTGCTAACACTTTCTATCGCGACTCCGTGAAGGGCCG
ATTCACTGTCTCCAGAGATAATGCAAGAAGCAGCCTATACCTACAAATGG
ACAGTCTGAGGTCTGAGGACACGGCCACTTATTACTGTACAACAGAGGCT
TACGGATATAACTCAAATTGGTTTGGTTACTGGGGCCAAGGCACTCTGGT
CACTGTCTCGAGTGCCCAAACGACACCCCCATCTGTCTATCCACTGGCCC
CTGGATCTGCTGCCCAAACTAACTCCATGGTGACCCTGGGATGCCTGGTC
AAGGGCTATTTCCCTGAGCCAGTGACAGTGACCTGGAACTCTGGATCCCT
GTCCAGCGGTGTGCACACCTTCCCGGCTGTCCTGCAATCTGACCTCTACA
CTCTGAGCAGCTCAGTGACTGTCCCCTCCAGCACCTGGCCCAGCGAGACC
GTCACCTGCAACGTTGCCCACCCGGCCAGCAGCACCAAGGTGGACAAGAA
AATTGTGCCCAGGGATTGT SEQ ID NO: 17 (LCDR2 of 1979)
GTTSLAD SEQ ID NO: 18 (LCDR3 of 1979)
LQAYSTPFTF SEQ ID NO: 19 (HCDR1 of 1979)
NSYWD SEQ ID NO: 20 (HCDR2 of 1979)
YINYSGSTGYNPSLKS SEQ ID NO: 21 (HCDR3 of 1979)
GTYGYNAYHFDY SEQ ID NO: 22 (LCVR of 1979)
DIQMTQSPASLSASLEEIVTITCQASQDIGNWLSWYQQKPGKSPHLLIYG
TTSLADGVPSRFSGSRSGTQYSLKISGLQVADIGIYVCLQAYSTPFTFGS
GTKLEIK SEQ ID NO: 23 (HCVR of 1979)
EVHLVESGPGLVKPSQSLSLTCSVTGYSITNSYWDWIRKFPGNKMEWMGY
INYSGSTGYNPSLKSRISISRDTSNNQFFLQLNSITTEDTATYYCARGTY
GYNAYHFDYWGRGVMVTVSS SEQ ID NO: 24 (LCVR DNA of 1979)
GACATCCAAATGACACAGTCTCCTGCCTCCCTGTCTGCATCTCTGGAAGA
AATTGTCACCATTACATGCCAGGCAAGCCAGGACATTGGTAATTGGTTAT
CATGGTATCAGCAGAAACCAGGGAAATCTCCTCACCTCCTGATCTATGGT
ACCACCAGCTTGGCAGATGGGGTCCCATCAAGGTTCAGCGGCAGTAGATC
TGGTACACAGTATTCTCTTAAGATCAGCGGACTACAGGTTGCAGATATTG
GAATCTATGTCTGTCTACAGGCTTATAGTACTCCATTCACGTTCGGCTCA
GGGACAAAGCTGGAAATAAAA SEQ ID NO: 25 (HCVR DNA of 1979)
GAGGTGCACCTGGTGGAGTCTGGACCTGGCCTTGTGAAACCCTCACAGTC
ACTCTCCCTCACCTGTTCTGTCACTGGTTACTCCATCACTAATAGTTACT
GGGACTGGATCCGGAAGTTCCCAGGAAATAAAATGGAGTGGATGGGATAC
ATAAACTACAGTGGTAGCACTGGCTACAACCCATCTCTCAAAAGTCGAAT
CTCCATTAGTAGAGACACATCGAACAATCAGTTCTTCCTGCAGCTGAACT
CTATAACTACTGAGGACACAGCCACATATTACTGTGCACGAGGGACCTAT
GGGTATAACGCCTACCACTTTGATTACTGGGGCCGAGGAGTCATGGTCAC
AGTCTCGAGC SEQ ID NO: 26 (1979 LC Kappa full)
DIQMTQSPASLSASLEEIVTITCQASQDIGNWLSWYQQKPGKSPHLLIYG
TTSLADGVPSRFSGSRSGTQYSLKISGLQVADIGIYVCLQAYSTPFTFGS
GTKLEIKRTDAAPTVSIFPPSSEQLTSGGASVVCFLNNFYPKDINVKWKI
DGSERQNGVLNSWTDQDSKDSTYSMSSTLTLTKDEYERHNSYTCEATHKT
STSPIVKSFNRNEC SEQ ID NO: 27 (1979 HC mIgG1 full)
EVHLVESGPGLVKPSQSLSLTCSVTGYSITNSYWDWIRKFPGNKMEWMGY
INYSGSTGYNPSLKSRISISRDTSNNQFFLQLNSITTEDTATYYCARGTY
GYNAYHFDYWGRGVMVTVSSAKTTPPSVYPLAPGSAAQTNSMVTLGCLVK
GYFPEPVTVTWNSGSLSSGVHTFPAVLQSDLYTLSSSVTVPSSTWPSETV
TCNVAHPASSTKVDKKIVPRDCGCKPCICTVPEVSSVFIFPPKPKDVLTI
TLTPKVTCVVVDISKDDPEVQFSWFVDDVEVHTAQTQPREEQFNSTFRSV
SELPIMHQDWLNGKEFKCRVNSAAFPAPIEKTISKTKGRPKAPQVYTIPP
PKEQMAKDKVSLTCMITDFFPEDITVEWQWNGQPAENYKNTQPIMDTDGS
YFVYSKLNVQKSNWEAGNTFTCSVLHEGLHNHHTEKSLSHSPGK SEQ ID NO: 28 (1979 HC mFabno hinge full)
EVHLVESGPGLVKPSQSLSLTCSVTGYSITNSYWDWIRKFPGNKMEWMGY
INYSGSTGYNPSLKSRISISRDTSNNQFFLQLNSITTEDTATYYCARGTY
GYNAYHFDYWGRGVMVTVSSAKTTPPSVYPLAPGSAAQTNSMVTLGCLVK
GYFPEPVTVTWNSGSLSSGVHTFPAVLQSDLYTLSSSVTVPSSTWPSETV
TCNVAHPASSTKVDKKIVPRDC SEQ ID NO: 29 (1979 LC DNA Kappa full)
GACATCCAAATGACACAGTCTCCTGCCTCCCTGTCTGCATCTCTGGAAGA
AATTGTCACCATTACATGCCAGGCAAGCCAGGACATTGGTAATTGGTTAT
CATGGTATCAGCAGAAACCAGGGAAATCTCCTCACCTCCTGATCTATGGT
ACCACCAGCTTGGCAGATGGGGTCCCATCAAGGTTCAGCGGCAGTAGATC
TGGTACACAGTATTCTCTTAAGATCAGCGGACTACAGGTTGCAGATATTG
GAATCTATGTCTGTCTACAGGCTTATAGTACTCCATTCACGTTCGGCTCA
GGGACAAAGCTGGAAATAAAACGTACGGATGCTGCACCAACTGTATCCAT
CTTCCCACCATCCAGTGAGCAGTTAACATCTGGAGGTGCCTCAGTCGTGT
GCTTCTTGAACAACTTCTACCCCAAAGACATCAATGTCAAGTGGAAGATT
GATGGCAGTGAACGACAAAATGGCGTCCTGAACAGTTGGACTGATCAGGA
CAGCAAGGACAGCACCTACAGCATGAGCAGCACCCTCACGTTGACCAAGG
ACGAGTATGAACGACATAACAGCTATACCTGTGAGGCCACTCACAAGACA
TCAACTTCACCCATTGTCAAGAGCTTCAACAGGAATGAGTGT SEQ ID NO: 30 (1979 HC DNA mIgG1 full)
GAGGTGCACCTGGTGGAGTCTGGACCTGGCCTTGTGAAACCCTCACAGTC
ACTCTCCCTCACCTGTTCTGTCACTGGTTACTCCATCACTAATAGTTACT
GGGACTGGATCCGGAAGTTCCCAGGAAATAAAATGGAGTGGATGGGATAC
ATAAACTACAGTGGTAGCACTGGCTACAACCCATCTCTCAAAAGTCGAAT
CTCCATTAGTAGAGACACATCGAACAATCAGTTCTTCCTGCAGCTGAACT
CTATAACTACTGAGGACACAGCCACATATTACTGTGCACGAGGGACCTAT
GGGTATAACGCCTACCACTTTGATTACTGGGGCCGAGGAGTCATGGTCAC
AGTCTCGAGTGCCAAAACGACACCCCCATCTGTCTATCCACTGGCCCCTG
GATCTGCTGCCCAAACTAACTCCATGGTGACCCTGGGATGCCTGGTCAAG
GGCTATTTCCCTGAGCCAGTGACAGTGACCTGGAACTCTGGATCCCTGTC
CAGCGGTGTGCACACCTTCCCGGCTGTCCTGCAATCTGACCTCTACACTC
TGAGCAGCTCAGTGACTGTCCCCTCCAGCACCTGGCCCAGCGAGACCGTC
ACCTGCAACGTTGCCCACCCGGCCAGCAGCACCAAGGTGGACAAGAAAAT
TGTGCCCAGGGATTGTGGTTGTAAGCCTTGCATATGTACAGTCCCAGAAG
TATCATCTGTCTTCATCTTCCCCCCAAAGCCCAAGGATGTGCTCACCATT
ACTCTGACTCCTAAGGTCACGTGTGTTGTGGTAGACATCAGCAAGGATGA
TCCCGAGGTCCAGTTCAGCTGGTTTGTAGATGATGTGGAGGTGCACACAG
CTCAGACGCAACCCCGGGAGGAGCAGTTCAACAGCACTTTCCGCTCAGTC
AGTGAACTTCCCATCATGCACCAGGACTGGCTCAATGGCAAGGAGTTCAA
ATGCAGGGTCAACAGTGCAGCTTTCCCTGCCCCCATCGAGAAAACCATCT
CCAAAACCAAAGGCAGACCGAAGGCTCCACAGGTGTACACCATTCCACCT
CCCAAGGAGCAGATGGCCAAGGATAAAGTCAGTCTGACCTGCATGATAAC
AGACTTCTTCCCTGAAGACATTACTGTGGAGTGGCAGTGGAATGGGCAGC
CAGCGGAGAACTACAAGAACACTCAGCCCATCATGGACACAGATGGCTCT
TACTTCGTCTACAGCAAGCTCAATGTGCAGAAGAGCAACTGGGAGGCAGG
AAATACTTTCACCTGCTCTGTGTTACATGAGGGCCTGCACAACCACCATA
CTGAGAAGAGCCTCTCCCACTCTCCTGGTAA SEQ ID NO: 31 (1979 HC DNA mFabno hinge full)
GAGGTGCACCTGGTGGAGTCTGGACCTGGCCTTGTGAAACCCTCACAGTC
ACTCTCCCTCACCTGTTCTGTCACTGGTTACTCCATCACTAATAGTTACT
GGGACTGGATCCGGAAGTTCCCAGGAAATAAAATGGAGTGGATGGGATAC
ATAAACTACAGTGGTAGCACTGGCTACAACCCATCTCTCAAAAGTCGAAT
CTCCATTAGTAGAGACACATCGAACAATCAGTTCTTCCTGCAGCTGAACT
CTATAACTACTGAGGACACAGCCACATATTACTGTGCACGAGGGACCTAT
GGGTATAACGCCTACCACTTTGATTACTGGGGCCGAGGAGTCATGGTCAC
AGTCTCGAGTGCCAAAACGACACCCCCATCTGTCTATCCACTGGCCCCTG
GATCTGCTGCCCAAACTAACTCCATGGTGACCCTGGGATGCCTGGTCAAG
GGCTATTTCCCTGAGCCAGTGACAGTGACCTGGAACTCTGGATCCCTGTC
CAGCGGTGTGCACACCTTCCCGGCTGTCCTGCAATCTGACCTCTACACTC
TGAGCAGCTCAGTGACTGTCCCCTCCAGCACCTGGCCCAGCGAGACCGTC
ACCTGCAACGTTGCCCACCCGGCCAGCAGCACCAAGGTGGACAAGAAAAT
TGTGCCCAGGGATTGT
```

```
Sequence listing
```

SEQ ID NO: 32-Rat TNFα
MSTESMIRDVELAEEEALPKKMGGLQNSRRCLCLSLFSFLLVAGATTLFCL
LNFGVIGPNKEEKFPNGLPLISSMAQTLTLRSSSQNSSDKPVAHVVANHQ
AEEQLEWLSQRANALLANGMDLKDNQLVVPADGLYLIYSQVLFKGQGCPD
YVLLTHTVSRFAISYQEKVSLLSAIKSPCPKDTPEGAELKPWYEPMYLGG
VFQLEKGDLLSAEVNLPKYLDITESGQVYFGVIAL

SEQ ID NO: 33-Mouse TNFα
MSTESMIRDVELAEEEALPQKMGGFQNSRRCLCLSLFSFLLVAGATTLFCL
LNFGVIGPQRDEKFPNGLPLISSMAQTLTLRSSSQNSSDKPVAHVVANHQ
VEEQLEWLSQRANALLANGMDLKDNQLVVPADGLYLVYSQVLFKGQGCPD
YVLLTHTVSRFAISYQEKVNLLSAVKSPCPKDTPEGAELKPWYEPIYLGG
VFQLEKGDQLSAEVNLPKYLDFAESGQVYFGVIAL SEQ ID NO: 34-Human TNFα
MSTESMIRDVELAEEEALPKKTGGPQGSRRCLFLSLFSFLIVAGATTLFCL
LHFGVIGPQREEFPRDLSLISPLAQAVRSSSRTPSDKPVAHVVANPQAEG
QLQWLNRRANALLANGVELRDNQLVVPSEGLYLIYSQVLFKGQGCPSTHV
LLTHTISRIAVSYQTKVNLLSAIKSPCQRETPEGAEAKPWYEPIYLGGVF
QLEKGDRLSAEINRPDYLDFAESGQVYFGIIAL SEQ ID NO: 35-Soluble form of human TNFα
SVRSSSRTPSDKPVAHVVANPQAEGQLQWLNRRANALLANGVELRDNQLV
VPSEGLYLIYSQVLFKGQGCPSTHVLLTHTISRIAVSYQTKVNLLSAIKS
PCQRETPEGAEAKPWYEPIYLGGVFQLEKGDRLSAEINRPDYLDFAESGQ
VYFGIIAL SEQ ID NO: 36-Soluble form of human TNFα, but
lacking the "S" cloning artefact of SEQ ID NO: 35
VRSSSRTPSDKPVAHVVANPQAEGQLQWLNRRANALLANGVELRDNQLVV
PSEGLYLIYSQVLFKGQGCPSTHVLLTHTISRIAVSYQTKVNLLSAIKSP
CQRETPEGAEAKPWYEPIYLGGVFQLEKGDRLSAEINRPDYLDFAESGQV
YFGIIAL

The invention claimed is:
1. A complex comprising (i) an antibody, (ii) a trimeric protein that is a tumor necrosis factor (TNF) superfamily member, and (iii) a compound that is capable of binding to a trimeric protein that is a TNF superfamily member, wherein the antibody comprises
   (a) a HCDR1/HCDR2/HCDR3 sequence combination selected from SEQ ID NOs: 4/5/6 and SEQ ID NOs: 19/20/21, and a LCDR1/LCDR2/LCDR3 sequence combination selected from SEQ ID NOs: 1/2/3 and SEQ ID NOs: 1/17/18; or
   (b) a HCDR1/HCDR2/HCDR3/LCDR1/LCDR2/LCDR3 sequence combination of SEQ ID NOs: 4/5/6/1/2/3 or SEQ ID NOs: 19/20/21/1/17/18, wherein:
      (a) the compound antagonizes the signalling induced by the trimer through the receptor;
      (b) the compound increases the thermal transition midpoint ($T_m$) of the trimeric form of the TNF superfamily member compared to the $T_m$ of the trimeric form of the TNF superfamily member in the absence of the compound;
      (c) the compound increases the binding affinity of the TNF superfamily member to the requisite receptor compared to the binding affinity of the TNF superfamily member to its receptor in the absence of the compound; and
      (d) the compound has an $IC_{50}$ value of 500 nM or less.
2. The complex of claim 1, wherein:
   (a) the $T_m$ increases by at least 1° C.;
   (b) the $T_m$ increases by at least 10° C.; or
   (c) the $T_m$ increases by between 10° C. and 20° C.
3. The complex of claim 1, wherein:
   (a) the compound increases the binding affinity of the TNF superfamily member to the requisite receptor by increasing the on rate ($k_{on-r}$) and/or decreasing the off rate ($k_{off-r}$) compared to the $k_{on-r}$ and $k_{off-r}$ values for binding of the TNF superfamily member to its receptor in the absence of the compound;
   (b) the compound increases the binding affinity of the TNF superfamily member to the requisite receptor by increasing the on rate ($k_{on-r}$) compared to the $k_{on-r}$ value for binding of the TNF superfamily member to its receptor in the absence of the compound;
   (c) the compound decreases the $K_{D-r}$ of the TNF superfamily member to the requisite receptor compared to the $K_{D-r}$ of the TNF superfamily member to its receptor in the absence of the compound, wherein:
      (i) the compound decreases the $K_{D-r}$ of the TNF superfamily member to the requisite receptor by at least 10 times compared to the $K_{D-r}$ of the TNF superfamily member to its receptor in the absence of the compound;
      (ii) the $K_{D-r}$ value of the TNF superfamily member for binding to the requisite receptor in the presence of the compound is less than 10 nM; or
   (d) the compound decreases the $K_{D-r}$ of the TNF superfamily member to the requisite receptor compared to the $K_{D-r}$ of the TNF superfamily member to its receptor in the absence of the compound, wherein:
      a) the compound decreases the $K_{D-r}$ of the TNF superfamily member to the requisite receptor by at least 4 times compared to the $K_{D-r}$ of the TNF superfamily member to its receptor in the absence of the compound;
      b) the $K_{D-r}$ value of the TNF superfamily member for binding to the requisite receptor in the presence of the compound is less than 600 pM, or is less than 200 pM.
4. The complex of claim 1, wherein—the compound is selected from the group consisting of compounds (1)-(6), or salts or solvates thereof:

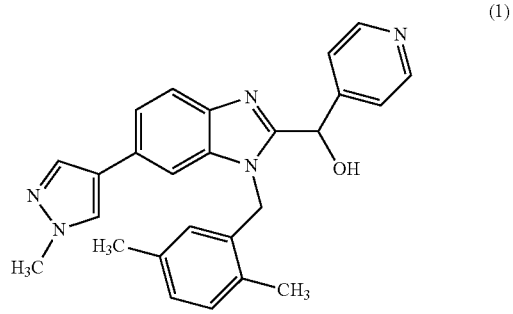
(1)

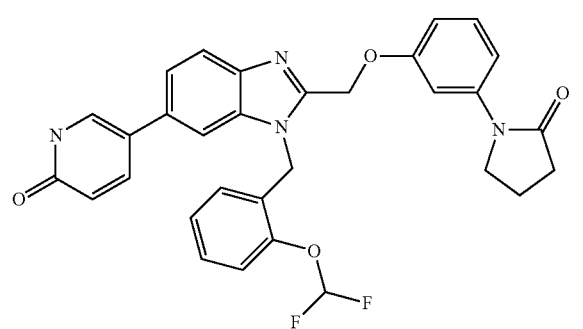
(2)

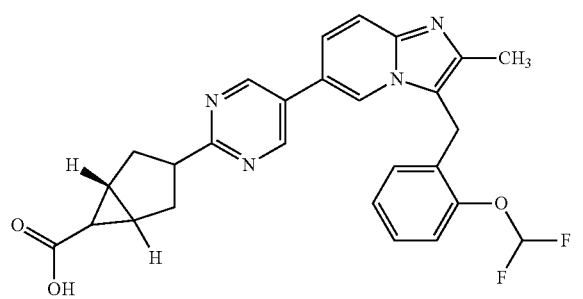
(3)

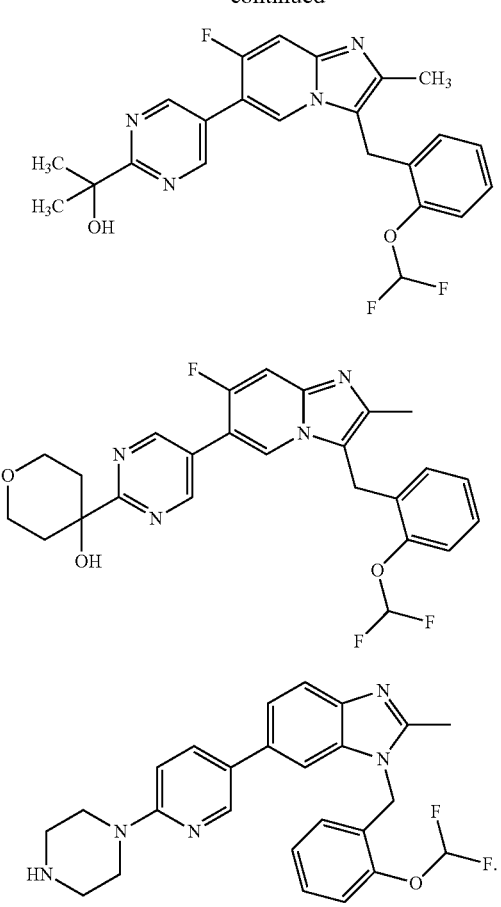

5. The complex of claim 1, wherein the antibody binds to a trimer-compound complex with a $K_{D\text{-}ab}$ that is at least 100 times lower, or at least 200 times lower, than the $K_{D\text{-}ab}$ for binding to the trimeric TNF superfamily member in the absence of compound and/or for binding to the compound in the absence of the TNF superfamily member.

6. The complex of claim 1, wherein:
(a) the TNF superfamily member is TNFα and the receptor is the TNF receptor; or
(b) the TNF superfamily member is TNFα and the receptor is TNFR1.

7. The complex of claim 6, wherein:
(a) the TNFα is TNFαs;
(b) the TNFα is TNFαs and the TNFαs comprises the sequence of SEQ ID NO: 35 or SEQ ID NO: 36, or a variant thereof; or
(c) the TNFα is trimeric.

8. The complex of claim 6, wherein:
(a) the antibody binds selectively to a TNFα-compound complex compared with binding to the compound in the absence of the TNFα and/or binding to the TNFα in the absence of the compound; or
(b) the antibody binds selectively to the TNFα-compound complex compared with binding to the compound in the absence of the TNFα and/or binding to the TNFα in the absence of the compound and the antibody binds to the TNFα-compound complex with a $K_{D\text{-}ab}$ that is at least 100 times lower, or at least 200 times lower, than the $K_{D\text{-}ab}$ for binding to the TNFα in the absence of compound and/or for binding to the compound in the absence of the TNFα.

9. The complex of claim 1, wherein the antibody comprises:
a heavy and light chain pair of SEQ ID NOs: 12/11, 13/11, 27/26 or 28/26, or sequences which are at least 95% identical thereto and wherein the sequences that are at least 95% identical thereto comprise:
(i) HCDR1/HCDR2/HCDR3/LCDR1/LCDR2/LCDR3 sequences consisting of SEQ ID NOs: 4/5/6/1/2/3 and the remainder of the heavy and light chains comprise at least 95% identity to SEQ ID NOs: 12 and 11 respectively;
(ii) HCDR1/HCDR2/HCDR3/LCDR1/LCDR2/LCDR3 sequences consisting of SEQ ID NOs: 4/5/6/1/2/3 and the remainder of the heavy and light chains comprise at least 95% identity to SEQ ID NOs: 13 and 11 respectively;
(iii) HCDR1/HCDR2/HCDR3/LCDR1/LCDR2/LCDR3 sequences consisting of SEQ ID NOs: 19/20/21/1/17/18 and the remainder of the heavy and light chains comprise at least 95% identity to SEQ ID NOs: 27 and 26 respectively; or
(iv) HCDR1/HCDR2/HCDR3/LCDR1/LCDR2/LCDR3 sequences consisting of SEQ ID NOs: 19/20/21/1/17/18 and the remainder of the heavy and light chains comprise at least 95% identity to SEQ ID NOs: 28 and 26 respectively.

10. The complex according to claim 1, wherein the antibody is:
(a) a humanised antibody; or
(b) a Fab, modified Fab, Fab', modified Fab', F(ab')$_2$, Fv, single domain antibody or an scFv.

11. An isolated polynucleotide encoding the antibody of claim 1.

* * * * *